US009096681B2

(12) United States Patent
Munshi et al.

(10) Patent No.: US 9,096,681 B2
(45) Date of Patent: Aug. 4, 2015

(54) XBP1, CD138, AND CS1 PEPTIDES

(75) Inventors: Nikhil C. Munshi, Needham, MA (US);
Kenneth C. Anderson, Wellesley, MA (US); Jooeun Bae, West Roxbury, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 580 days.

(21) Appl. No.: 12/995,661

(22) PCT Filed: Jun. 1, 2009

(86) PCT No.: PCT/US2009/045866
§ 371 (c)(1),
(2), (4) Date: Mar. 4, 2011

(87) PCT Pub. No.: WO2009/149021
PCT Pub. Date: Dec. 10, 2009

(65) Prior Publication Data
US 2011/0159021 A1 Jun. 30, 2011

Related U.S. Application Data

(60) Provisional application No. 61/058,180, filed on Jun. 2, 2008.

(51) Int. Cl.
| A61K 38/04 | (2006.01) |
| A61K 38/08 | (2006.01) |
| A61K 35/74 | (2006.01) |
| A61K 39/39 | (2006.01) |
| C07K 14/47 | (2006.01) |
| C07K 14/705 | (2006.01) |
| A61K 35/16 | (2006.01) |
| A61K 38/00 | (2006.01) |

(52) U.S. Cl.
CPC ........ *C07K 14/4702* (2013.01); *C07K 14/70507* (2013.01); *A61K 38/00* (2013.01)

(58) Field of Classification Search
None
See application file for complete search history.

(56) References Cited

U.S. PATENT DOCUMENTS

2003/0113332 A1    6/2003    Mathew et al.

FOREIGN PATENT DOCUMENTS

| JP | 2007-503465 | 2/2007 |
| JP | 2007-530675 | 11/2007 |
| WO | WO 0168848 A2 * | 9/2001 |
| WO | WO2008-019376 A2 | 2/2008 |
| WO | WO 2008/019378 A1 | 2/2008 |
| WO | WO2009/149021 A2 | 12/2009 |
| WO | WO2014/071402 A1 | 5/2014 |

OTHER PUBLICATIONS

Horiguchi et al (Clin. Canc. Res. 2002, 8: 3885-3882).*
Cerny et al (J. Clin. Invest. 1995, 95: 921-530).*
A_Geneseq Acc No. AAU29119, 2007.*
Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
XBP-1 a Selective and Specific Target for Immunotherapy in Myeloma, Bae, et al., Blood, (ASH Annual Meeting Abstracts) 2005 106: Abstract 1594.
Development of Novel CD138 Antigen-Specific Peptide Capable of Eliciting Myeloma-Specific Cytotoxic T Lymphocytes Response, Bae et al., Blood (ASH Annual Meeting Abstracts) 2006 106 Abstract 3465.
Identification of CS1 Peptides for Induction of Antigen-Specific CTLs in Multiple Myeloma, Song et al., Blood (ASH Annual Meeting Abstracts) 2007 110: Abstract 1611.
Bouchon et al., *Cutting Edge: Activation of NK Cell-Mediated Cytotoxicity by a SAP-Independent Receptor of the CD2 Family*, J. Immunol., 167(10):5517-5521 (2001).
JPO Office Action issued in corresponding Japanese Patent Application No. 2011-512566, issued Jan. 30, 2014 (with English Translation).
JPO Office Action dated Jun. 20, 2014, in JP Application No. 2011-512566.
International Search Report and Written Opinion dated Mar. 11, 2014, in International Application No. PCT/US2013/068582.
Bae et al., "Induction of T Cell Immunity Using a Multipeptide Cocktail Containing XBP1, CD138 and CS1 Peptides in Smoldering Multiple Myeloma", Blood, 120(21):5039 (Nov. 2012).
Bae et al., "Myeloma-Specific Multiple Peptides Able to Generate Cytotoxic T Lymphocytes: A Potential Therapeutic Application in Multiple Myeloma and Other Plasma Cell Disorders", Clin. Cancer Res., 18(17):4850-4860 (Sep. 2012).
Celis et al., "Induction of Anti-Tumor Cytotoxic T. Lymphocytes in Normal Humans Using Primary Cultures and Synthetic Peptide Epitopes", Proceedings of Natl Academy of Sciences, 91:2105-2109 (Mar. 1994).
Kawashima et al., "The Multi-Epitope Approach for Immunotherapy for Cancer: Identification of Several CTL Epitopes from Various tumor-Associated Antigens Expressed on Solid Epithelial Tumors" Human Immunol., 59(1):1-14 (Jan. 1998).
Appendix, Trial record I of I for: PVX-410, Phase 112a Study of Cancer Vaccine to Treat Smoldering Multiple Myeloma, Jul. 2013.
Bae et al., *Identification of CD19 and CD20 Peptides for Induction of Antigen-Specific CTLs against B-Cell Malignancies*, Clin. Cancer Res., Amer. Assoc. Cancer Res., 11:1629-1638 (Feb. 15, 2005).
Bae et al., *Identification of novel myeloma-specific XBP1 peptides able to generate cytotoxic T lymphocytes: a potential therapeutic application in multiple myeloma*, Leukemia, (2011), p. 1610-1619 vol. 25.

(Continued)

*Primary Examiner* — Gerald R Ewoldt
*Assistant Examiner* — Marianne Dibrino
(74) *Attorney, Agent, or Firm* — Fish & Richardson P.C.

(57) ABSTRACT

The disclosure features, inter alia, immunogenic XBP1-, CD138-, and CS1-derived peptides (and pharmaceutical compositions thereof). The peptides can be used in a variety of methods such as methods for inducing an immune response, methods for producing an antibody, and methods for treating a cancer (e.g., a plasma cell disorder such as multiple myeloma or Waldenstrom's macroglobulinemia). The peptides can also be included in MHC molecule multimer compositions and used in, e.g., methods for detecting a T cell in a population of cells.

11 Claims, 24 Drawing Sheets

(56) References Cited

OTHER PUBLICATIONS

Diefenbach et al., *Safety and Immunogenicity Study of NY-ESO-1b Peptide and Montanide ISA-51 Vacination of Patients with Epithelial Ovarian Cancer in High-Risk First Remission*, Clin Cancer Res;14:2740-2748 (2008).

Hundemer et al., *Identification of a new HLA-A2-restricted T-cell epitope within HM1.24 as immunotherapy target for multiple myeloma*, Experimental Hematology, 34(4):486-496 (Apr. 1, 2006).

Jain et al., *Synthetic Tumor-Specific Breakpoint Peptide Vaccine in Patients With Chronic Myeloid Leukemia and Minimal Residual Disease*, Cancer, 3924-3934, (Sep. 1, 2009), vol. 115.

Jalili, *Induction of HM1.24 peptide-specific cytotoxic T lymphocytes by using peripheral-blood stem-cell harvests in patients with multiple myeloma*, Blood, 106(10): 3538-3545 (Nov. 15, 2005).

Keilholz et al., *A clinical and immunologic phase 2 trial of Wilms tumor gene product 1 (WT1) peptide vaccination in patients with AML and MDS*, Blood, 113(26):6541-6548 (Jun. 25, 2009).

Kirkwood et al., *Immunogenicity and Antitumor Effects of Vaccination with Peptide Vaccine +/− Granulocyte-Monocyte Colony-Stimulating Factor and/or IFN-α2b in Advanced Metastatic Melanoma: Eastern Cooperative Oncology Group Phase II Trial E1696*, Clin Cancer Res, 15:1443-1451 (2009).

Klebanoff et al., *Therapeutic cancer vaccines: are we there yet?*, Immunol Rev., 239(1): 27-44 (Jan. 2011).

Lotz et al., *Targeting positive 1-3,6-9 regulatory domain I-binding factor 1 and X box-binding protein 1 transcription factors by multiple myeloma-reactive CTL*, J. Immunol., 175(2):1301-1309 (Jul. 1, 2005).

Maslak et al., *Vaccination with synthetic analog peptides derived from WT1 oncoprotein induces T-cell responses in patients with complete remission from acute myeloid leukemia*, Blood, 116(2):171-179, Jul. 15, 2010.

Perez et al., *A New Era in Anticancer Peptide Vaccines*, Cancer, 2071-2080 (May 1, 2010).

Tsuruma et al., *Clinical and immunological evaluation of anti-apoptosis protein, survivin-derived peptide vaccine in phase I clinical study for patients with advanced or recurrent breast cancer*, J Translational Medicine, 6(24):1-11, (2008).

Vacchelli et al., *Trial watch—Peptide vaccines in cancer therapy*, OncoImmunology 1(9):1557-1576 (Dec. 2012).

Supplementary European Search Report dated Sep. 17, 2011 for EP Application No. 09 75 9182.

International Search Report and Written Opinion for PCT/US09/45866, dated May 25, 2010 (12 pages).

Lotz. Tolerance and Immunity to Human Tumor-Associated Antigens. Dissertation Johannes Gutenberg-Universitat in Mainz Dec. 16, 2003 [Online] [Retrieved from the Internet on Jan. 21, 2010: < http://ubm.opus.hbz-nrw.de/volltexte/2004/479/pdf/diss.pdf>); p. 40 table 2 and 4-6 para 2, p. 43 para 2 (100 pages).

Parker et al., Scheme for ranking potential HLA-A2 binding peptides based on independent binding of individual peptide side-chains, J. Immunol 152(1):163-175 (1994).

\* cited by examiner

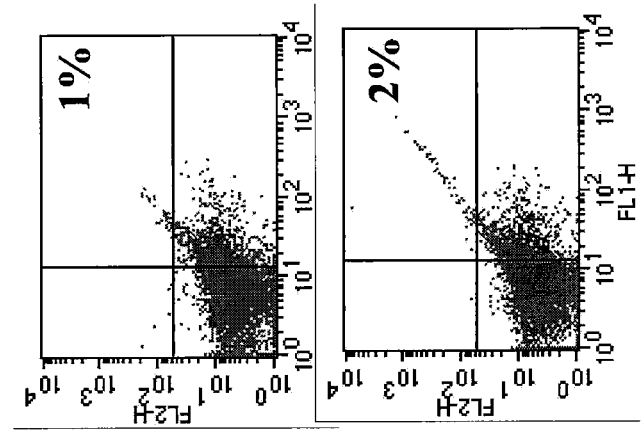
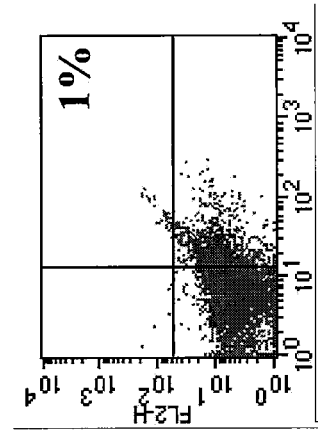
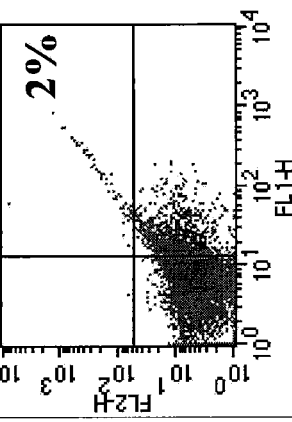
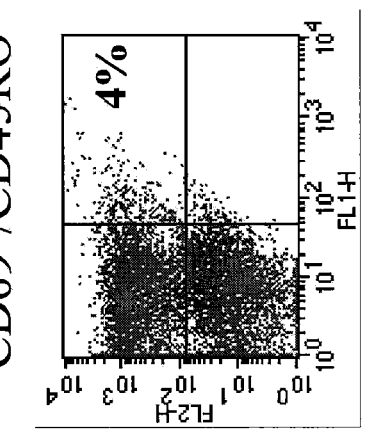
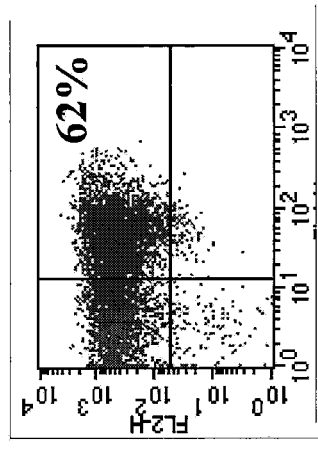
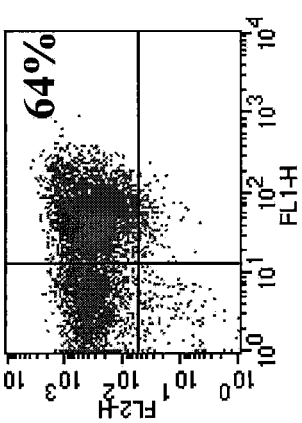
Fig. 6

XBP1-2M-CTL

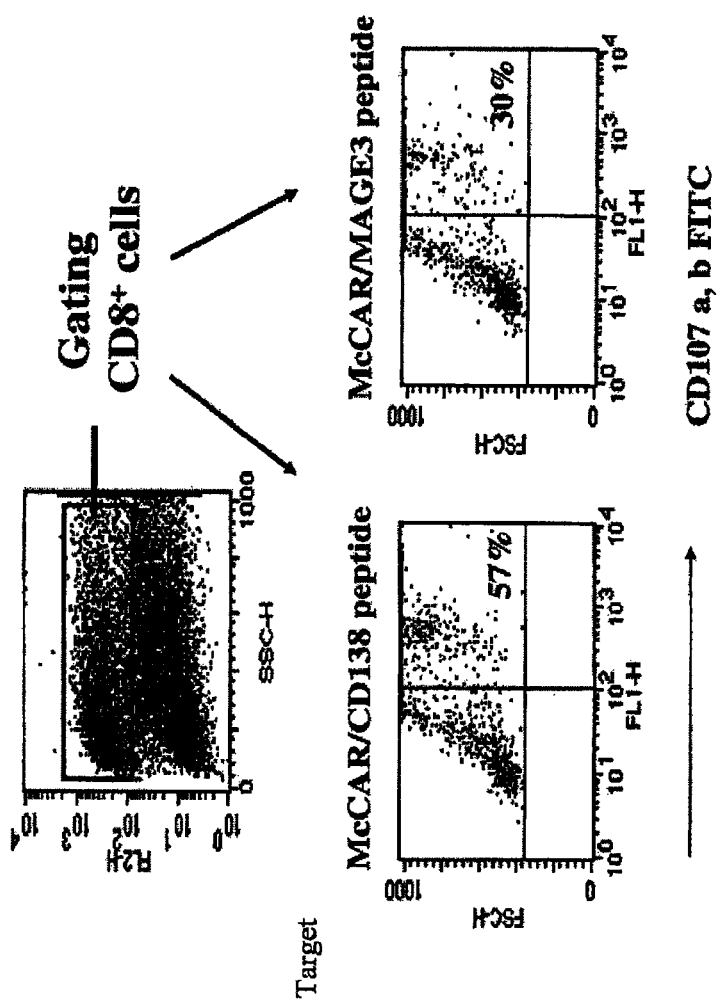

```
SEQUENCE LISTING

<160> NUMBER OF SEQ ID NOS: 28

<210> SEQ ID NO 1
<211> LENGTH: 9
<212> TYPE: PRT
<213> ORGANISM: Homo sapiens

<400> SEQUENCE: 1

Leu Leu Arg Glu Lys Thr His Gly Leu
1               5

<210> SEQ ID NO 2
<211> LENGTH: 9
<212> TYPE: PRT
<213> ORGANISM: Homo sapiens

<400> SEQUENCE: 2

Asn Ile Ser Pro Trp Ile Leu Ala Val
1               5

<210> SEQ ID NO 3
<211> LENGTH: 9
<212> TYPE: PRT
<213> ORGANISM: Homo sapiens

<400> SEQUENCE: 3

Ile Leu Ala Val Leu Thr Leu Gln Ile
1               5

<210> SEQ ID NO 4
<211> LENGTH: 9
<212> TYPE: PRT
<213> ORGANISM: Homo sapiens

<400> SEQUENCE: 4

Ile Leu Ala Val Leu Thr Leu Gln Ile
1               5

<210> SEQ ID NO 5
<211> LENGTH: 9
<212> TYPE: PRT
<213> ORGANISM: Homo sapiens

<400> SEQUENCE: 5

Lys Leu Leu Leu Glu Asn Gln Leu Leu
1               5
```

```
<210> SEQ ID NO 6
<211> LENGTH: 9
<212> TYPE: PRT
<213> ORGANISM: Homo sapiens

<400> SEQUENCE: 6

Tyr Ile Ser Pro Trp Ile Leu Ala Val
1               5

<210> SEQ ID NO 7
<211> LENGTH: 9
<212> TYPE: PRT
<213> ORGANISM: Homo sapiens

<400> SEQUENCE: 7

Gly Ile Leu Asp Asn Leu Asp Pro Val
1               5

<210> SEQ ID NO 8
<211> LENGTH: 9
<212> TYPE: PRT
<213> ORGANISM: Homo sapiens

<400> SEQUENCE: 8

Ile Leu Leu Gly Ile Leu Asp Asn Leu
1               5

<210> SEQ ID NO 9
<211> LENGTH: 9
<212> TYPE: PRT
<213> ORGANISM: Homo sapiens

<400> SEQUENCE: 9

Glu Leu Phe Pro Gln Leu Ile Ser Val
1               5

<210> SEQ ID NO 10
<211> LENGTH: 9
<212> TYPE: PRT
<213> ORGANISM: Homo sapiens

<400> SEQUENCE: 10

Tyr Leu Phe Pro Gln Leu Ile Ser Val
1               5

<210> SEQ ID NO 11
<211> LENGTH: 9
<212> TYPE: PRT
<213> ORGANISM: Homo sapiens

<400> SEQUENCE: 11

Val Ile Ala Gly Gly Leu Val Gly Leu
1               5

<210> SEQ ID NO 12
<211> LENGTH: 9
<212> TYPE: PRT
<213> ORGANISM: Homo sapiens

<400> SEQUENCE: 12

Gly Leu Val Gly Leu Ile Phe Ala Val
1               5

<210> SEQ ID NO 13
<211> LENGTH: 9
```

-continued

<212> TYPE: PRT
<213> ORGANISM: Homo sapiens

<400> SEQUENCE: 13

Ala Leu Trp Leu Trp Leu Cys Ala Leu
 1               5

<210> SEQ ID NO 14
<211> LENGTH: 9
<212> TYPE: PRT
<213> ORGANISM: Homo sapiens

<400> SEQUENCE: 14

Trp Leu Trp Leu Cys Ala Leu Ala Leu
 1               5

<210> SEQ ID NO 15
<211> LENGTH: 10
<212> TYPE: PRT
<213> ORGANISM: Homo sapiens

<400> SEQUENCE: 15

Leu Leu Leu Ser Leu Phe Val Leu Gly Leu
 1               5                  10

<210> SEQ ID NO 16
<211> LENGTH: 9
<212> TYPE: PRT
<213> ORGANISM: Homo sapiens

<400> SEQUENCE: 16

Ser Leu Phe Val Leu Gly Leu Phe Leu
 1               5

<210> SEQ ID NO 17
<211> LENGTH: 9
<212> TYPE: PRT
<213> ORGANISM: Homo sapiens

<400> SEQUENCE: 17

Leu Leu Val Pro Leu Leu Leu Ser Leu
 1               5

<210> SEQ ID NO 18
<211> LENGTH: 9
<212> TYPE: PRT
<213> ORGANISM: Homo sapiens

<400> SEQUENCE: 18

Thr Leu Ile Tyr Ile Leu Trp Gln Leu
 1               5

<210> SEQ ID NO 19
<211> LENGTH: 261
<212> TYPE: PRT
<213> ORGANISM: Homo sapiens

<400> SEQUENCE: 19

Met Val Val Val Ala Ala Pro Asn Pro Asp Gly Thr Pro Lys
 1               5                  10                  15

Val Leu Leu Leu Ser Gly Gln Pro Ala Ser Ala Ala Gly Ala Pro Ala
                 20                  25                  30

Gly Gln Ala Leu Pro Leu Met Val Pro Ala Gln Arg Gly Ala Ser Pro
             35                  40                  45

Glu Ala Ala Ser Gly Gly Leu Pro Gln Ala Arg Lys Arg Gln Arg Leu
        50                  55                  60

Thr His Leu Ser Pro Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                    85                  90                  95

Glu Leu Glu Gln Gln Val Val Asp Leu Glu Glu Glu Asn Gln Lys Leu
                100                 105                 110

Leu Leu Glu Asn Gln Leu Leu Arg Glu Lys Thr His Gly Leu Val Val
                115                 120                 125

Glu Asn Gln Glu Leu Arg Gln Arg Leu Gly Met Asp Ala Leu Val Ala
            130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
                180                 185                 190

Val Leu Thr Leu Gln Ile Gln Ser Leu Ile Ser Cys Trp Ala Phe Trp
            195                 200                 205

Thr Thr Trp Thr Gln Ser Cys Ser Ser Asn Ala Leu Pro Gln Ser Leu
210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260

<210> SEQ ID NO 20
<211> LENGTH: 376
<212> TYPE: PRT
<213> ORGANISM: Homo sapiens

<400> SEQUENCE: 20

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
                20                  25                  30

Gly Gln Ala Leu Pro Leu Met Val Pro Ala Gln Arg Gly Ala Ser Pro
            35                  40                  45

Glu Ala Ala Ser Gly Gly Leu Pro Gln Ala Arg Lys Arg Gln Arg Leu
        50                  55                  60

Thr His Leu Ser Pro Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                    85                  90                  95

Glu Leu Glu Gln Gln Val Val Asp Leu Glu Glu Glu Asn Gln Lys Leu
                100                 105                 110

Leu Leu Glu Asn Gln Leu Leu Arg Glu Lys Thr His Gly Leu Val Val
                115                 120                 125

Glu Asn Gln Glu Leu Arg Gln Arg Leu Gly Met Asp Ala Leu Val Ala
            130                 135                 140

Glu Glu Glu Ala Glu Ala Lys Gly Asn Glu Val Arg Pro Val Ala Gly

```
                145                 150                 155                 160
Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
                180                 185                 190

Asp Ile Leu Leu Gly Ile Leu Asp Asn Leu Asp Pro Val Met Phe Phe
                195                 200                 205

Lys Cys Pro Ser Pro Glu Pro Ala Ser Leu Glu Glu Leu Pro Glu Val
                210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
                260                 265                 270

Glu Ser Gln Ala Asn Val Val Val Lys Ile Glu Glu Ala Pro Leu Ser
                275                 280                 285

Pro Ser Glu Asn Asp His Pro Glu Phe Ile Val Ser Val Lys Glu Glu
                290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
                340                 345                 350

Ser Leu Leu Gly Val Asn His Ser Trp Glu Asp Thr Phe Ala Asn Glu
                355                 360                 365

Leu Phe Pro Gln Leu Ile Ser Val
                370                 375

<210> SEQ ID NO 21
<211> LENGTH: 310
<212> TYPE: PRT
<213> ORGANISM: Homo sapiens

<400> SEQUENCE: 21

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
                35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
                100                 105                 110

Gly Leu Thr Ala Arg Glu Gln Glu Ala Thr Pro Arg Pro Arg Glu Thr
                115                 120                 125

Thr Gln Leu Pro Thr Thr His Gln Ala Ser Thr Thr Thr Ala Thr Thr
                130                 135                 140
```

-continued

```
Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
            165                 170                 175

Thr Pro His Thr Glu Asp Gly Gly Pro Ser Ala Thr Glu Arg Ala Ala
        180                 185                 190

Glu Asp Gly Ala Ser Ser Gln Leu Pro Ala Ala Glu Gly Ser Gly Glu
    195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
            245                 250                 255

Ile Ala Gly Gly Leu Val Gly Leu Ile Phe Ala Val Cys Leu Val Gly
        260                 265                 270

Phe Met Leu Tyr Arg Met Lys Lys Lys Asp Glu Gly Ser Tyr Ser Leu
    275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 22
<211> LENGTH: 335
<212> TYPE: PRT
<213> ORGANISM: Homo sapiens

<400> SEQUENCE: 22

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205
```

-continued

Ile Leu Ala Arg Lys Leu Cys Glu Gly Ala Ala Asp Asp Pro Asp Ser
    210                 215                 220

Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 23
<211> LENGTH: 4
<212> TYPE: PRT
<213> ORGANISM: Homo sapiens

<400> SEQUENCE: 23

Lys Asp Glu Leu
1

<210> SEQ ID NO 24
<211> LENGTH: 9
<212> TYPE: PRT
<213> ORGANISM: Influenza virus

<400> SEQUENCE: 24

Gly Ile Leu Gly Phe Val Phe Thr Leu
1               5

<210> SEQ ID NO 25
<211> LENGTH: 9
<212> TYPE: PRT
<213> ORGANISM: Influenza virus

<400> SEQUENCE: 25

Gly Ile Leu Gly Phe Val Phe Thr Leu
1               5

<210> SEQ ID NO 26
<211> LENGTH: 9
<212> TYPE: PRT
<213> ORGANISM: Homo sapiens

<400> SEQUENCE: 26

Phe Leu Trp Gly Pro Arg Ala Leu Val
1               5

<210> SEQ ID NO 27
<211> LENGTH: 9
<212> TYPE: PRT
<213> ORGANISM: Homo sapiens

<400> SEQUENCE: 27

Arg Met Ser Glu Leu Glu Gln Gln Val
1               5

```
<210> SEQ ID NO 28
<211> LENGTH: 9
<212> TYPE: PRT
<213> ORGANISM: Influenza virus

<400> SEQUENCE: 28

Tyr Ile Leu Asp Asn Leu Asp Pro Val
1               5
```

XBP1, CD138, AND CS1 PEPTIDES

CROSS REFERENCE TO RELATED APPLICATIONS

This application is a U.S. National Phase filing under 35 U.S.C. 371 of International Application No. PCT/US2009/045866, filed Jun. 1, 2009, which claims priority of U.S. Provisional Application No. 61/058,180 filed Jun. 2, 2008. The disclosures of International Application No. PCT/US2009/045866 and U.S. Provisional Application No. 61/058,180 are incorporated herein by reference in their entirety.

STATEMENT REGARDING FEDERALLY SPONSORED RESEARCH OR DEVELOPMENT

The research described in this application was supported by grant nos. P50-100707, PO1-78378, and RO1-50947, each awarded from the National Institutes of Health. Thus, the government has certain rights in the invention.

BACKGROUND

Multiple myeloma and Waldenstrom's macroglobulinemia are two hematological cancers that affect approximately 45,000 and 1,500 people, respectively, in United States each year. Although both disorders are often treated using, e.g., chemotherapy alone or in combination with a bone marrow transplant, the prognosis for patients afflicted with one of these disorders is generally poor. Efficacious therapies and/or prophylactic regimens are therefore urgently needed.

SUMMARY

The present disclosure relates to immunogenic X-Box Protein 1 (XBP1)-, CD138-, and CD2 Subset 1 (CS1)-derived peptides and methods of using the peptides. The peptides were discovered to possess a number of properties including, e.g., elevated affinity for HLA-A2 molecules, elevated stability within the peptide binding cleft of HLA-A2, and the ability, when expressed on the surface of cell (e.g., a cancer cell) in the context of an MHC molecule, to induce the activation and proliferation of T cells.

It will be evident from the following description that the peptides (and pharmaceutical compositions thereof) can be used in a variety of applications such as methods for inducing an immune response, methods for activating a T cell, methods for producing an antibody, and methods for treating, e.g., a cancer (e.g., a plasma cell cancer such as multiple myeloma or Waldenstrom's macroglobulinemia). Moreover, the peptides can be included in MHC molecule multimer compositions, which can be used to, e.g., detect a peptide-specific T cell in a population of cells.

In one aspect, the disclosure features an isolated peptide consisting of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-18. The peptide can bind to a major histocompatibility complex (MHC) molecule such as an MHC class I or class II molecule.

In another aspect, the disclosure features an isolated peptide consisting of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-18. The peptide can, in association with a major histocompatibility complex (MHC) molecule, be recognized by an antigen specific T cell receptor on a T cell.

In another aspect, the disclosure features an isolated peptide comprising: a first amino acid sequence consisting of a peptide that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-18; and a second amino acid sequence that is heterologous to the first amino acid sequence.

In another aspect, the disclosure features an isolated peptide consisting of an amino acid sequence of any one of SEQ ID NOS:1-18, but with not more than four substitutions. The not more than four substitutions can be conservative or non-conservative.

In yet another aspect, the disclosure features an isolated peptide comprising: a first amino acid sequence consisting of any one of SEQ ID NOS:1-18, but with not more than four substitutions; and a second amino acid sequence that is heterologous to the first amino acid sequence. The not more than four substitutions can be conservative or non-conservative.

In some embodiments, any of the isolated peptides described herein can bind to a major histocompatibility complex (MHC) molecule (e.g., an MHC class I or class II molecule). The MHC molecule can be, e.g., an HLA-A2 molecule. The MHC molecule can be, e.g., a human MHC molecule.

In some embodiments, any of the isolated peptides described herein can, in association with a major histocompatibility complex (MHC) molecule, be recognized by an antigen specific T cell receptor on a T cell.

In some embodiments of any of the isolated peptides described herein, the second amino acid sequence can comprise, or be, a targeting polypeptide, an immune stimulatory molecule, an immunoglobulin or antigen-binding fragment thereof, an Fc receptor-binding region of an immunoglobulin molecule, or a carrier polypeptide. The targeting polypeptide can be, e.g., one that targets the isolated peptide to an antigen presenting cell (e.g., a dendritic cell, a macrophage, a monocyte, or a B cell). The immune stimulatory molecule can be, e.g., a cytokine or a T helper epitope. The immunoglobulin can be, e.g., a single chain Fv immunoglobulin fragment or an entire immunoglobulin molecule. The carrier peptide can comprise, or be, a KLH (keyhole limpet hemocyanin) polypeptide.

In some embodiments, any of the isolated peptides described herein can contain a linker sequence. The linker sequence can connect a first amino acid sequence to a second amino acid sequence. The linker sequence can comprise, or consist of, at least one (e.g., one, two, three, four, five, six, seven, eight, nine, or 10 or more) protease cleavage site.

In some embodiments of any of the isolated peptides described herein, the second amino acid sequence can be amino terminal or carboxy terminal to the first amino acid sequence.

In some embodiments, any of the isolated peptides described herein can be detectably labeled.

In yet another aspect, the disclosure features: (i) an isolated nucleic acid encoding any of the isolated peptides described herein; (ii) a vector comprising the isolated nucleic acid of (i); or (iii) a cultured cell comprising the vector of (ii). The vector can be operably linked to an expression control sequence. The cultured cell can be a prokaryotic cell or eukaryotic cell. The cultured cell can be, e.g., a fungal cell, a plant cell, or an animal cell (e.g., a nematode cell, an insect cell, a bird cell, a fish cell, or a mammalian cell (e.g., a human cell)). The cultured cell can be an immune cell such as any of the immune cells described herein.

In another aspect, the disclosure features a method of producing a peptide. The method involves the step of culturing any of the cultured cells described herein under conditions that permit the expression of the peptide. The method can also include the step of isolating the peptide from the cell or from the medium in which the cell was cultured.

In another aspect, the disclosure features a pharmaceutical composition comprising one or more of any of the isolated peptides described herein and a pharmaceutically acceptable carrier. The composition can also include, e.g., one or more therapeutic agents, diagnostic agents, or prophylactic agents, or immune stimulating agents. Immune stimulating agents include, but are not limited to, e.g., a T helper epitope, an altered peptide ligand, an adjuvant, or any other immune stimulating agent described herein. The T helper epitope can be, e.g., a PADRE sequence or a universal Tetanus Toxoid T helper (TT Th) epitope. The adjuvant can be selected from the group consisting of Freund's complete adjuvant, Freund's incomplete adjuvant, alum, a ligand for a Toll receptor, QS21, RIBI, cholera toxin (CT), E. coli heat labile toxin (LT), mutant CT (MCT), and mutant E. coli heat labile toxin (MLT).

In yet another aspect, the disclosure features a kit comprising: (i) one or more of any of the isolated peptides described herein; and instructions for administering the peptide to a subject; and/or (ii) one or more of the isolated nucleic acids encoding the isolated peptides, one or more vectors containing the isolated nucleic acids, or one or more cultured cells containing the vectors, and instructions for producing the isolated peptides.

In some embodiments, the kits can also include, e.g., one or more pharmaceutically acceptable carriers, one or more immune stimulating agents, or one or more therapeutic agents, diagnostic agents, or prophylactic agents. The one or more immune stimulating agents can be selected from the group consisting of a T helper epitope, an altered peptide ligand, and an adjuvant.

In another aspect, the disclosure features an article of manufacture comprising: a container; and a composition contained within the container, wherein the composition comprises an active ingredient for inducing an immune response in a mammal, wherein the active ingredient comprises one or more of any of the isolated peptides described herein. The container can have a label indicating that the composition is for use in inducing an immune response in a mammal. The label can further indicate that the composition is to be administered to a mammal having, suspected of having, or at risk of developing, multiple myeloma or Waldenstrom's macroglobulinemia. The article of manufacture can also include instructions for administering the composition to the mammal. The composition can be, e.g., in solution, dried, or lyophilized.

In yet another aspect, the disclosure features a method for inducing an immune response in a subject, which method includes the step of delivering to a subject one or more (e.g., one, two, three, four, five, six, seven, eight, nine, 10, 11, 12, 13, 14, 15, 16, 17, or 18) of any of the isolated peptides described herein. The method can also include the step of, after delivering the one or more peptides to the subject, determining if an immune response occurred in the subject. The one or more peptides can be delivered to the subject as a pharmaceutical composition. The subject can be, e.g., a mammal (e.g., a human) or any other subject described herein. The subject can have, be suspected of having, at risk of developing, or in remission from multiple myeloma or Waldenstrom's macroglobulinemia.

In some embodiments, the method can include determining whether one or more plasma cells of the subject's multiple myeloma or Waldenstrom's macroglobulinemia express XBP 1, CD138, or CS1.

In some embodiments, the method can include administering to the subject one or more chemotherapeutic agents, one or more forms of ionizing radiation, or one or more immunotherapy agents. The one or more forms of ionizing radiation can be, e.g., gamma-irradiation, X-irradiation, or beta-irradiation. The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, taxol, transplatinum, 5-fluorouracil, vincristin, vinblastin, methotrexate, and an analog of any of the aforementioned. The method can also include administering to the subject one or more immune stimulating agents.

In some embodiments, the delivering comprises administering to the subject the one or more peptides. In some embodiments, the delivering comprises administering to the subject one or more nucleic acids, each of which comprises a nucleotide sequence encoding the one or more peptides, the nucleotide sequence being operably-linked to a expression control sequence. The nucleic acid can be in a recombinant cell transfected with the nucleic acid and expressing the one or more peptides. The recombinant cell can be a transfected cell, or the progeny of a transfected cell, made by transfecting a cell obtained from the subject. The recombinant cell can be an antigen presenting cell such as, but not limited to, a dendritic cell, a macrophage, a monocyte, or a B cell.

In some embodiments of any of the above-described methods, the delivering includes: contacting the one or more peptides to a cell; and after contacting the one or more peptides to the cell, delivering the cell to the subject. The cell can be, e.g., an antigen presenting cell such as any of those described herein. The cell can be, e.g., a cell, or the progeny of a cell, obtained from the subject. In some embodiments, the cell can be a cell, or the progeny of a cell, obtained from another subject of the same species as the subject. The other subject can express at least one MHC molecule in common with the subject. The at least one MHC molecule can be, e.g., an MHC class I molecule such as an HLA-A2 molecule.

In some embodiments, the methods can also include, prior to administering the one or more peptides to the subject, obtaining a population of cells comprising one or more hematopoietic stem cells from the subject.

In another aspect, the disclosure features a method for treating multiple myeloma or Waldenstrom's macroglobulinemia. The method includes the step of administering to a subject one or more (e.g., one, two, three, four, five, six, seven, eight, nine, 10, 11, 12, 13, 14, 15, 16, 17, or 18) of any of the peptides described herein, wherein the subject has, or is at risk of developing, multiple myeloma or Waldenstrom's macroglobulinemia.

In another aspect, the disclosure features a method for selecting a treatment for a mammal in need thereof. The method includes the steps of: determining if one or more cancer cells of a cancer in a mammal express XBP1, wherein the cancer is multiple myeloma or Waldenstrom's macroglobulinemia; and if one or more of the cancer cells express XBP1, selecting as a therapeutic agent for the mammal one or more peptides selected from the group consisting of: (a) an isolated peptide consisting of an amino acid sequence that is at least 66% identical to any one of SEQ ID NOS:1-10; (b) an isolated peptide consisting of an amino acid sequence of any one of SEQ ID NOS:1-10 with not more than four substitutions; (c) an isolated peptide comprising: (i) a first amino acid sequence consisting of any one of SEQ ID NOS:1-10 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:1-10; and (ii) a second amino acid sequence that is heterologous to the first amino acid sequence. The method can also include the step of, after determining that one or more of the cells of the cancer express XBP1, delivering to the subject the selected one or more peptides.

In yet another aspect, the disclosure features a method for selecting a treatment for a mammal with cancer. The method includes the steps of: determining if one or more cancer cells of a cancer in a mammal express CD138, wherein the cancer is multiple myeloma or Waldenstrom's macroglobulinemia; and if one or more of the cancer cells express CD138, selecting as a therapeutic agent for the mammal one or more peptides selected from the group consisting of: (a) an isolated peptide consisting of an amino acid sequence that is at least 66% identical to any one of SEQ ID NOS:11-14; (b) an isolated peptide consisting of an amino acid sequence of any one of SEQ ID NOS:11-14 with not more than four substitutions; and (c) an isolated peptide comprising: (i) a first amino acid sequence consisting of any one of SEQ ID NOS:11-14 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:11-14; and (ii) a second amino acid sequence that is heterologous to the first amino acid sequence. The method can also include the step of, after determining that one or more of the cells of the cancer express CD138, delivering to the subject the one or more peptides.

In another aspect, the disclosure features a method for selecting a treatment for a mammal in need thereof. The method includes determining if one or more cancer cells of a cancer in a mammal express CS1, wherein the cancer is multiple myeloma or Waldenstrom's macroglobulinemia; and if one or more of the cancer cells express CS1, selecting as a therapeutic agent for the mammal one or more peptides selected from the group consisting of: (a) an isolated peptide consisting of an amino acid sequence that is at least 66% identical to any one of SEQ ID NOS:15-18; (b) an isolated peptide consisting of an amino acid sequence of any one of SEQ ID NOS:15-18 with not more than four substitutions; (c) an isolated peptide comprising: (i) a first amino acid sequence consisting of any one of SEQ ID NOS:15-18 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:15-18; and (ii) a second amino acid sequence that is heterologous to the first amino acid sequence. The method can also include the step of, after determining that one or more of the cells of the cancer express CS1, delivering to the subject the selected one or more peptides.

In yet another aspect, the disclosure features a method for selecting a therapeutic agent for a mammal with multiple myeloma or Waldenstrom's macroglobulinemia. The method includes the step of, if one or more cancer cells of a mammal's multiple myeloma or Waldenstrom's macroglobulinemia express XBP1, selecting as a therapeutic agent for the mammal one or more peptides selected from the group consisting of: (a) an isolated peptide consisting of an amino acid sequence that is at least 66% identical to any one of SEQ ID NOS:1-10; (b) an isolated peptide consisting of an amino acid sequence of any one of SEQ ID NOS:1-10 with not more than four substitutions; and (c) an isolated peptide comprising: (i) a first amino acid sequence consisting of any one of SEQ ID NOS:1-10 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:1-10; and (ii) a second amino acid sequence that is heterologous to the first amino acid sequence.

In yet another aspect, the disclosure features a method for selecting a therapeutic agent for a mammal with multiple myeloma or Waldenstrom's macroglobulinemia, which method includes the step of, if one or more cancer cells of a mammal's multiple myeloma or Waldenstrom's macroglobulinemia express CD138, selecting as a therapeutic agent for the mammal one or more peptides selected from the group consisting of: (a) an isolated peptide consisting of an amino acid sequence that is at least 66% identical to any one of SEQ ID NOS:11-14; (b) an isolated peptide consisting of an amino acid sequence of any one of SEQ ID NOS:11-14 with not more than four substitutions; and (c) an isolated peptide comprising: (i) a first amino acid sequence consisting of any one of SEQ ID NOS:11-14 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:11-14; and (ii) a second amino acid sequence that is heterologous to the first amino acid sequence.

In another aspect, the disclosure features a method for selecting a therapeutic agent for a mammal with multiple myeloma or Waldenstrom's macroglobulinemia, which method includes the step of, if one or more cancer cells of a mammal's multiple myeloma or Waldenstrom's macroglobulinemia express CS1, selecting as a therapeutic agent for the mammal one or more peptides selected from the group consisting of: (a) an isolated peptide consisting of an amino acid sequence that is at least 66% identical to any one of SEQ ID NOS:15-18; (b) an isolated peptide consisting of an amino acid sequence of any one of SEQ ID NOS:15-18 with not more than four substitutions; and (c) an isolated peptide comprising: (i) a first amino acid sequence consisting of any one of SEQ ID NOS:15-18 with not more than four substitutions; and (ii) a second amino acid sequence that is heterologous to the first amino acid sequence; and (d) an isolated peptide comprising: (i) a first amino acid sequence consisting of an amino acid sequence that is at least 66% identical to any one of SEQ ID NOS:15-18; and (ii) a second amino acid sequence that is heterologous to the first amino acid sequence.

In some embodiments of any of the above methods, the subject or mammal can be one who has received a therapy for multiple myeloma or Waldenstrom's macroglobulinemia and was non-responsive to the therapy.

In another aspect, the disclosure features a method for inducing an immune response in a mammal. The method includes the step of administering to a subject an immune cell, or a progeny of the immune cell, that has been contacted with one or more (e.g., one, two, three, four, five, six, seven, eight, nine, 10, 11, 12, 13, 14, 15, 16, 17, or 18) of any of the peptides described herein. The method can include contacting the immune cell with the one or more peptides. The immune cell can be, e.g., a T cell. The T cell can be contacted with the one or more peptides in the presence of an antigen presenting cell.

In some embodiments, the method can also include the step of, prior to the contacting, obtaining the immune cell. The immune cell can be obtain from the subject or from another subject of the same species as the subject.

In some embodiments (for example, in embodiments where the cell is obtained from another subject), the immune cell expresses at least one MHC molecule in common with the subject. The at least one MHC molecule can be, e.g., an MHC class I molecule such as an HLA-A2 molecule.

In yet another aspect, the disclosure features a composition comprising: (i) one or more of any of the peptides described herein and (ii) a major histocompatibility complex (MHC) molecule multimer, wherein the multimer comprises two or more (e.g., two, three, four, five, six, seven, eight, nine, or 10 or more) peptide-binding regions of an MHC molecule. In some embodiments, each peptide-binding region has (i) bound to it. In some embodiments, each peptide-binding region has (i) non-covalently or covalently bound to it. The MHC molecule multimer can comprise two or more (e.g., two, three, four, five, six, seven, eight, nine, or 10 or more) entire MHC molecules. The MHC molecule multimer can comprise a human MHC molecule. The MHC molecule multimer can comprise an MHC class I molecule such as an HLA-A2 molecule.

In some embodiments, the composition can comprise at least two or more (e.g., two, three, four, five, six, seven, eight, nine, or 10 or more) of the peptides.

In some embodiments, the two or more peptide-binding regions can be from the same MHC molecule. In some embodiments, the two or more peptide-binding regions are from different MHC molecules. In some embodiments, the two or more peptide-binding regions can be a mixture of at least two (e.g., two, three, four, five, six, seven, eight, nine, or 10 or more) regions from the same MHC molecule and at least one (e.g., one, two, three, four, five, six, seven, eight, nine, or 10 or more) regions from a different MHC molecule.

In some embodiments, the MHC molecule multimer is capable of binding to at least one of the one of more peptides.

In some embodiments, the composition can be detectably labeled. For example, one or more of the peptides and/or one or more of the peptide-binding regions can be detectably labeled. In some embodiments, at least one of the one or more MHC molecule multimers or at least one of the one or more peptides are detectably labeled.

In yet another aspect, the disclosure features a kit comprising a composition comprising: one or more major histocompatibility complex (MHC) molecule multimers, wherein each multimer comprises two or more peptide-binding regions of an MHC molecule; and one of more of any of the peptides described herein. The kit can also include: instructions for contacting the composition with a cell, instructions for detectably labeling one of the one or more MHC molecule multimers or one of the one or more peptides; one or more detectable labels; and/or instructions for detecting at least one of the one or more detectable labels. The one or more detectable labels can be selected from the group consisting of luminescent labels, fluorescent labels, radioactive labels, and enzymatic labels.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., methods for inducing an immune response in a subject, will be apparent from the following description, from the drawings and from the claims.

BRIEF DESCRIPTION OF THE DRAWINGS

FIG. 6 is a series of two-dimensional FFC histograms depicting the percentage of cells in a population of lymphocytes that are CD69$^+$/CD45RO$^+$ or CD45RA$^+$/CCR7$^+$ following stimulation with XBP1 peptides: XBP1 2M or XBP1 3M. The Y-axis of each dot plot indicates the fluorescence intensity of fluorescently-labeled specific antibodies bound to CD69 antigen (left column) or CD45RA antigens (right column) on the cells and the X-axis of each dot plot indicates the fluorescence intensity of fluorescently-labeled specific antibodies bound to CD45RO antigen (left column) or CCR7 antigens (right column) on the cells. The indicated percentages of the cells in the upper right hand quadrants of the dot plots are indicated.

FIGS. 18A and 18B are a series of two-dimensional FFC histograms depicting the CD138-CTL-dependent lysis of cancer cells as determined by CD 107 assay. The X-axis of each dot plot represents the fluorescence intensity of a FITC-conjugated antibody that specifically binds to CD107a and CD107b and the Y-axis represents the fluorescence intensity of a PE-conjugated antibody that specifically binds to CD8. FIG. 18A shows the lysis by CTL of T2 cells pulsed with CD138 peptide or irrelevant MAGE3 peptide pulsed T2 cells at different ratios (effector: target ratios) (5:1, 1:1, or 1:5). FIG. 18B demonstrates the lysis by CTL of CD138 peptide-pulsed McCAR cells or irrelevant MAGE3 peptide pulsed McCAR (CD138+/HLA$^-$A2$^+$) cells at a ratio (effector:target ratio) of CTL to McCAR cells of (1:1). The indicated percentages of the cells in the upper right hand quadrants of the dot plots are indicated.

DETAILED DESCRIPTION

Figure 1:
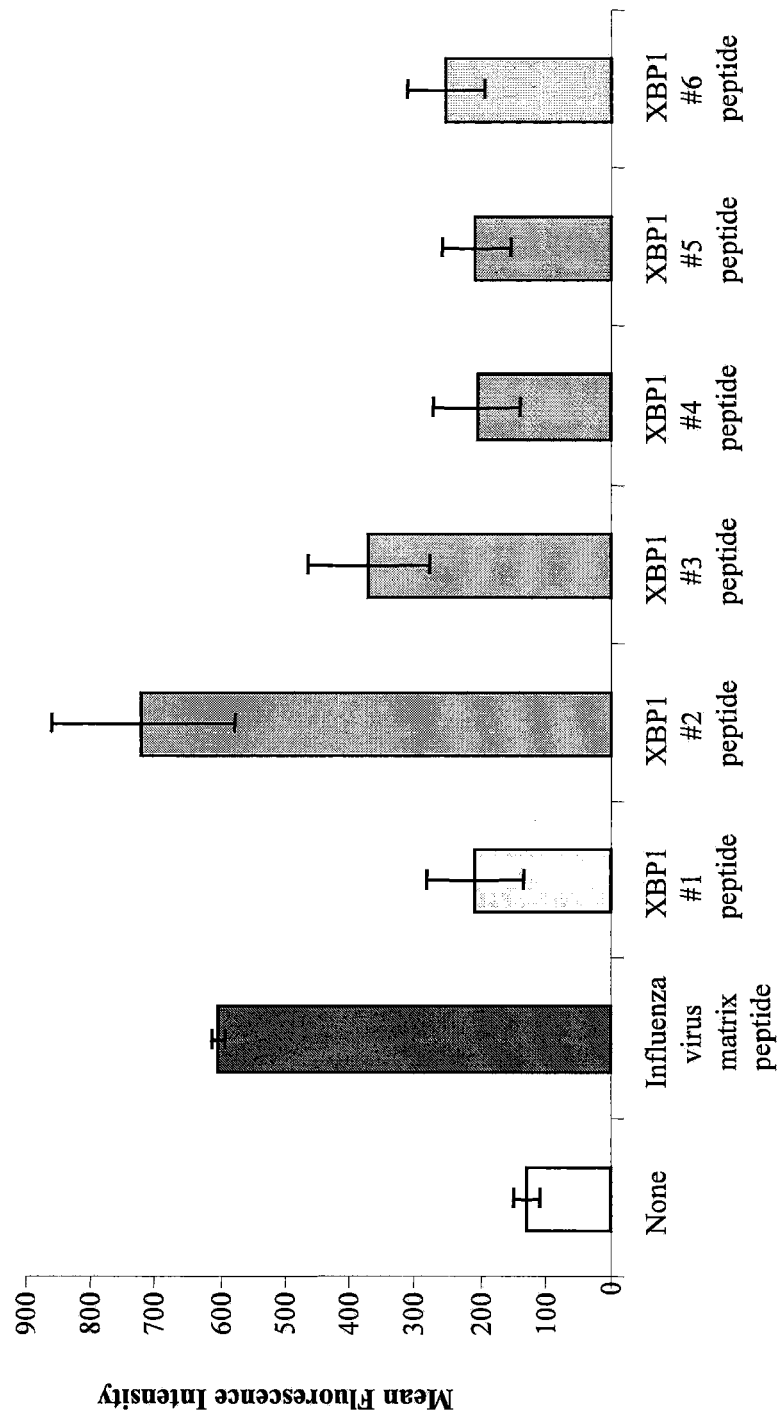
FIG. 1 is a bar graph depicting the affinity of fluorophore-labeled XBP1 peptides for HLA-A2 molecules on the surface of human T2 cells. The Y-axis represents the mean fluorescence intensity and the X-axis represents the various peptides screened in the assay: $XBP1_{117\text{-}125}$ (LLREKTHGL (SEQ ID NO:1); XBP1 #1 peptide), $XBP1_{184\text{-}192}$ (NISPWILAV (SEQ ID NO:2); XBP1 #2 peptide), $XBP1_{189\text{-}197}$ (ILAVLTLQI (SEQ ID NO:3); XBP1 #3 peptide), $XBP1_{192\text{-}200}$ (ILAVLTLQI (SEQ ID NO:4); XBP1 #4 peptide), $XBP1_{110\text{-}118}$ (KLLLENQLL (SEQ ID NO:5); XBP1 #5 peptide), and $XBP1_{93\text{-}101}$ (RMSELEQQV (SEQ ID NO:27); XBP 1 #6 peptide). The influenza virus protein matrix peptide$_{58\text{-}66}$ (GILGFVFTL (SEQ ID NO:24)) was also evaluated as a control.

The disclosure features immunogenic XBP1-, CD138-, and CS1-derived peptides (and pharmaceutical compositions thereof), which can be used to, e.g., induce an immune response (e.g., stimulate a CTL response), or stimulate the production of an antibody, in a subject. The peptides can be used in a variety of applications such as methods for inducing an immune response, methods for producing an antibody, and methods for treating a cancer (e.g., a plasma cell disorder such as multiple myeloma or Waldenstrom's macroglobulinemia). The peptides can also be included in MHC molecule multimer compositions and used in, e.g., methods for detecting a T cell in a population of cells.

A detailed description of the peptides as well as exemplary methods for making and using the peptides are set forth below.

Peptides

The disclosure features isolated peptides consisting of, or consisting essentially of, an amino acid sequence that is at least 66% (e.g., 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% or more) identical to any one of SEQ ID NOS:1-18 as depicted in Table 1.

TABLE 1

| Protein of Origin | Amino Acid Position | Amino Acid Sequence | SEQ ID NO: |
|---|---|---|---|
| XBP1, non-spliced | 117-125 | LLREKTHGL | 1 |
| XBP1, non-spliced | 184-192 | NISPWILAV | 2 |
| XBP1, non-spliced | 189-197 | ILAVLTLQI | 3 |
| XBP1, non-spliced | 192-200 | VLTLQIQSL | 4 |
| XBP1, non-spliced | 110-118 | KLLLENQLL | 5 |
| XBP1, non-spliced | 184-192 | YISPWILAV | 6 |
| XBP1, spliced | 196-204 | GILDNLDPV | 7 |
| XBP1, spliced | 193-201 | ILLGILDNL | 8 |
| XBP1, spliced | 367-375 | ELFPQLISV | 9 |
| XBP1, spliced | 367-375 | YLFPQLISV | 10 |
| CD138 | 256-264 | VIAGGLVGL | 11 |
| CD138 | 260-268 | GLVGLIFAV | 12 |
| CD138 | 5-13 | ALWLWLCAL | 13 |
| CD138 | 7-15 | WLWLCALAL | 14 |
| CS1 | 236-245 | LLLSLFVLGL | 15 |
| CS1 | 239-247 | SLFVLGLFL | 16 |
| CS1 | 232-240 | LLVPLLLSL | 17 |
| CS1 | 9-17 | TLIYILWQL | 18 |

Bolded residues indicate amino acid changes from the corresponding wild-type amino acid sequence.

The "XBP1, non-spliced" peptides depicted in Table 1 and referred to by amino acid position are fragments of XBP1 whose termini correspond to the relevant amino acid positions in the non-spliced form of human XBP1 protein having 261 amino acids and the following sequence:

MVVVAAAPNPADGTPKVLLLSGQPASAAGAPAGQALPLMVPAQRGASPEA

ASGGLPQARKRQRLTHLSPEEKALRRKLKNRVAAQTARDRKKARMSELEQ

QVVDLEEENQKLLLENQLLREKTHGLVVENQELRQRLGMDALVAEEEAEA

KGNEVRPVAGSAESAALRLRAPLQQVQAQLSPLQNISPWILAVLTLQIQS

LISCWAFWTTWTQSCSSNALPQSLPAWRSSQRSTQKDPVPYQPPFLCQWG

RHQPSWKPLMN
(SEQ ID NO: 19 Genbank Accession No. NP_005071).

The "XBP1, spliced" peptides depicted in Table 1 and referred to by amino acid position are fragments of XBP1 whose termini correspond to the relevant amino acid positions in the spliced form of human XBP1 (XBP1 spliced) protein having 376 amino acids and the following sequence:

MVVVAAAPNPADGTPKVLLLSGQPASAAGAPAGQALPLMVPAQRGASPEA

ASGGLPQARKRQRLTHLSPEEKALRRKLKNRVAAQTARDRKKARMSELEQ

QVVDLEEENQKLLLENQLLREKTHGLVVENQELRQRLGMDALVAEEEAEA

KGNEVRPVAGSAESAAGAGPVVTPPEHLPMDSGGIDSSDSESDILLGILD

NLDPVMFFKCPSPEPASLEELPEVYPEGPSSLPASLSLSVGTSSAKLEAI

NELIRFDHIYTKPLVLEIPSETESQANVVVKIEEAPLSPSENDHPEFIVS

VKEEPVEDDLVPELGISNLLSSSHCPKPSSCLLDAYSDCGYGGSLSPFSD

MSSLLGVNHSWEDTFANELFPQLISV
(SEQ ID NO: 20; Genbank Accession No. NP_001073007).

The "CD138" peptides depicted in Table 1 and referred to by amino acid position are fragments of CD138 whose termini correspond to the relevant amino acid positions within the human CD138 protein having 310 amino acids and the following sequence:

```
MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA
(SEQ ID NO: 21; Genbank Accession No.
NP_002988).
```

The "CS1" peptides depicted in Table 1 and referred to by amino acid position are fragments of CS1 whose termini correspond to the relevant amino acid positions within the human CS1 protein having 335 amino acids and the following sequence:

```
MAGSPTCLTLIYILWQLTGSAASGPVKELVGSVGGAVTFPLKSKVKQVDS

IVWTFNTTPLVTIQPEGGTIIVTQNRNRERVDFPDGGYSLKLSKLKKNDS

GIYYVGIYSSSLQQPSTQEYVLHVYEHLSKPKVTMGLQSNKNGTCVTNLT

CCMEHGEEDVIYTWKALGQAANESHNGSILPISWRWGESDMTFICVARNP

VSRNFSSPILARKLCEGAADDPDSSMVLLCLLLVPLLLSLFVLGLFLWFL

KRERQEEYIEEKKRVDICRETPNICPHSGENTEYDTIPHTNRTILKEDPA

NTVYSTVEIPKKMENPHSLLTMPDTPRLFAYENVI
(SEQ ID NO: 22; Genbank Accession No.
NP_067004).
```

The peptides described herein are often referred to herein using the residue number of the N and C terminal amino acids of the peptides (e.g., $XBP1_{117-125}$) as the relevant sequences occur in the wild-type, full length, mature human proteins having SEQ ID NOS: 19-22. These peptides will frequently have identical sequences to the corresponding segments of the wild-type, full-length, mature proteins having SEQ ID NOS: 19-22. It is understood, however, that the terms "XBP1, non-spliced peptides" (e.g., XBP1, non-spliced peptides having amino acid positions: 117-125, 184-192, 189-197, 192-200, or 110-118), "XBP1, spliced peptides" (e.g., XBP1, spliced peptides having amino acid positions: 196-204, 193-201, or 367-375), "CD138 peptides" (e.g., CD138 peptides having amino acid positions: 256-264, 260-268, 5-13, or 7-15), and CS1 peptides (e.g., CS1 peptides have amino acid positions 236-245, 239-247, 232-240, or 9-17) can be peptide fragments of the XBP1 nonspliced peptide, the XBP1 spliced peptide, the CD138, or CS1 polypeptide (respectively) of a species other than human. As will be appreciated by those skilled in the art, the numbers of the N and C terminal amino acids of peptide fragments of such non-human polypeptides are not necessarily the same as those in the corresponding peptide fragments of human polypeptides. Moreover, the lengths and/or amino acids of peptide fragments of non-human polypeptides will not necessarily be the same as those in the corresponding peptide fragments of human polypeptides. Those of skill in the art will know how to establish the N and C terminal amino acids, the lengths, and amino acid sequences of peptides derived from non-human XBP1 non-spliced, XBP1 spliced, CD138, and CS1 polypeptides. One useful method for doing this is sequence alignment and, in particular, maximum homology sequence alignment.

Percent identity between two peptide sequences (e.g., a peptide of SEQ ID NOS: 1-18 and another amino acid sequence that may be at least 66% identical to the peptide) can be determined using a variety of algorithms and computer programs including, but not limited to, Clustal W (The European Bioinformatics Institute (EMBL-EBI), BLAST-Protein (National Center for Biotechnology Information (NCBI), United States National Institutes of Health), and PSAlign (University of Texas A&M; Sze et al. (2006) Journal of Computational Biology 13:309-319).

Also disclosed herein are variants of the human and non-human peptides described above. Variants of the human and non-human peptides described herein can include forms of the peptides having: (i) not more than 4 (e.g., 3, 2, or 1) amino acid substitutions (e.g., conservative or non-conservative substitutions); (ii) terminal or internal deletions; or (iii) terminal or internal additions, all of which are elaborated on below.

The disclosure also features peptides consisting of, or consisting essentially of, an amino acid sequence of SEQ ID NO:1-18 (as depicted in Table 1), but with not more than four (e.g., not more than three, not more than two, or not more than 1) substitutions. The substitutions can be, e.g., conservative or non-conservative (as described above).

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

In some embodiments, one or more (e.g., one, two, three, four, or all five) of positions three, four, five, six, seven, and eight of any of the peptides are not substituted. In some embodiments, one or more of positions three, four, five, six, seven, and eight of any of the peptides are identical to the amino acids of the peptides in Table 1.

Also featured are peptides comprising: a first amino acid sequence consisting essentially, or consisting of, any one of SEQ ID NOS:1-18 as depicted in Table 1; and a second amino acid sequence that is heterologous to the first amino acid sequence. The first amino acid sequence can have, e.g., not more than four substitutions (conservative or non-conservative substitutions or can be at least about 66% 66% (e.g., 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% or more) identical to any one of SEQ ID NOS:1-18 as depicted in Table 1.

The second, heterologous amino acid sequence(s) of the peptide generally do not (and are selected such that do not) adversely affect the generation in the cell of an immunogenic peptide of SEQ ID NO:1-18. The cellular machinery is expected to remove any additional sequences in the peptide to yield an immunogenic peptide of SEQ ID NO:1-18, which peptide is presented by a class I or class II MHC molecule to stimulate an immune response against XBP1-, CD138-, or CS1-expressing cancer cells.

An amino acid sequence that is "heterologous" to a first amino acid sequence, or the term "heterologous amino acid sequence," is any amino acid sequence other than the amino acid sequence(s) flanking the first amino acid sequence as it occurs in nature. For example, two or more (e.g., two, three, four, five, six, seven, eight, nine, 10, 11, 12, 13, 14, 15, 16, 17, 18, 19, or or more) and/or less than 20 (e.g., 19, 18, 17, 16, 15, 14, 13, 12, 11, 10, nine, eight, seven, six, five, four, three, two, or one) carboxy- and/or amino-terminal amino acid(s) immediately flanking LLREKTHGL (SEQ ID NO:1) in a human XBP1 are not considered to be heterologous to SEQ ID NO:1. It is understood that a peptide containing a first amino acid sequence that is less than 100% identical to, or contains from one to four conservative substitutions in, an amino acid sequence of SEQ ID NOS:1-18, may not occur in nature at all.

In some embodiments, the second amino acid sequence can be a single amino acid. It is understood that an amino acid that is "heterologous" to a first amino acid sequence, or the term "heterologous amino acid," is any amino acid other than the amino acid(s) flanking the first amino acid sequence as it occurs in nature. For example, the two amino acid(s) immediately flanking LLREKTHGL (SEQ ID NO:1) in a human XBP1 are not considered to be heterologous to SEQ ID NO:1.

A heterologous sequence can be, for example, a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the peptide can contain a signal sequence from another protein such as a KDEL (SEQ ID NO:23) sequence or any other described herein. In some embodiments, the peptides can contain all or part of an immunoglobulin molecule (e.g., all or part of an immunoglobulin heavy chain constant region; see below). In some embodiments, the peptide can contain a therapeutic or immune-stimulating polypeptide (e.g., a T helper epitope (e.g., a PADRE epitope or a Tetanus Toxoid universal T helper cell epitope) or all or part of a cytokine or chemokine) and/or a carrier (e.g., KLH) useful, e.g., in eliciting an immune response (e.g., for antibody generation). In some embodiments, the peptide can contain one or more linker peptide sequences (see below). The peptide can also contain a targeting polypeptide. Heterologous sequences can be of varying length and in some cases can be longer sequences than the first amino acid sequences to which the heterologous amino acid sequences are attached. It is understood that a peptide containing a first amino acid sequence and a second amino acid sequence that is heterologous to the first does not correspond in sequence to a naturally occurring protein.

Targeting polypeptides, as used herein, are polypeptides that target the moiety (or moieties) they are attached to (e.g., the first amino acid sequence) to specific tissues (e.g., to a lymph node) or cells (e.g., to an antigen presenting cell or other immune cell), or where in vitro, specific isolated molecules or molecular complexes. Targeting polypeptides can be, e.g., an antibody (immunoglobulin) or antigen binding fragment thereof or a ligand for a cell surface receptor. An antibody (or antigen-binding fragment thereof) can be, e.g., a monoclonal antibody, a polyclonal antibody, a humanized antibody, a fully human antibody, a single chain antibody, a chimeric antibody, or an Fab fragment, an F(ab')$_2$ fragment, an Fab' fragment, an Fv fragment, or an scFv fragment of an antibody. Antibody fragments that include, or are, Fc regions (with or without antigen-binding regions) can also be used to target the reagents to Fc receptor-expressing cells (e.g., antigen presenting cells such as interdigitating dendritic cells, macrophages, monocytes, or B cells). A ligand for a cell surface receptor can be, e.g., a chemokine, a cytokine (e.g., interleukins 1, 2, 3, 4, 5, 6, 7, 8, 9, 10, 11, 12, 13, 14, 15, or 16), or a death receptor ligand (e.g., FasL or TNFα).

In some embodiments, the heterologous sequence can be, e.g., a "transportation sequence" that aids in the delivery of the peptide to the cell or to a specific compartment of a cell (e.g., the endoplasmic reticulum or Golgi apparatus). Transportation sequences can include, e.g., membrane translocating sequence, a transportan sequence, an antennapedia sequence, a cyclic integrin-binding peptide, and a Tat-mediated peptide, or modified versions thereof.

A linker peptide can connect the first amino acid sequence to one or more heterologous amino acid sequences. For example, a linker peptide can connect the first amino acid sequence to a second amino acid sequence. The linker peptide can, or contain, e.g., stretches of amino acids where at least four to six amino acids are glycine. (See, e.g., Mancebo et al. (1990) Mol. Cell. Biol. 10:2492-2502). A linker can also be, or contain, six or more (e.g., seven, eight, nine, 10, 11, or 12 or more) histidine residues. The linker peptide can contain, or be, at least one (e.g., one, two, three, four, five, six, seven, or eight or more) protease cleavage site(s). The protease sites can be, e.g., a trypsin, a chymotrypsin, or a factor Xa cleavage site. Such protease sites can be useful, e.g., to separate a first amino acid sequence from a heterologous sequence. For example, after expression and purification of a peptide containing a first amino acid sequence joined to a polyhistidine sequence (in this case used for purification) by a trypsin protease cleavage site, the polyhistidine sequence can be removed from first amino acid sequence by contacting the peptide with trypsin.

The first amino acid sequence and the second amino acid sequence can be associated with each other in a variety of ways. As used herein, "associated with" in the context of an interaction between two or more atoms or molecular units, includes any covalent or non-covalent bonding, or physical admixture, of two or more atoms or molecular units (e.g., a first amino acid sequence and a second amino acid sequence). The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). It is understood that the term "associated with" (e.g., in the context of a first amino acid sequence and a second amino acid sequence) is thus coextensive with the term "comprising."

In some embodiments, a peptide containing a first amino acid sequence and a second amino acid sequence can be a fusion protein. For example, the first amino acid sequence and second amino acid sequence can be encoded by (and expressed as fusion protein from) a single nucleic acid sequence. In some instances, the first amino acid sequence and second amino acid sequence can be encoded by two or more (e.g., three, four, five, or six or more) different nucleic acid sequences. For example, the first amino acid sequence can be encoded by a first nucleic acid sequence and the second amino acid sequence can be encoded by a second nucleic acid sequence (see below under "Nucleic Acids and Methods for Producing the Peptides").

When expressed or produced separately, a first amino acid sequence and a second amino acid sequence can be cross-linked together using any of a number of known chemical cross linkers. Examples of such chemical cross-linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable chemical cross-linker, 4-succinimidyloxycarbonyl-α-methyl-α(2-pyridyldithio)toluene (SMPT), forms such a linkage between the two amino acid sequences utilizing a terminal lysine on one of the amino acid sequences and a terminal cysteine on the other. Heterobifunctional reagents which cross-link by a different coupling moiety on each amino acid sequence. In this way, the resulting "dimers" will be heterodimers (peptides containing the first and second amino acid sequences) rather than either homodimers (e.g., two first amino acid sequences or two second amino acid sequences) or a mixture of homodimers and heterodimers. Thus, the coupling moiety on a first amino acid sequence could be a cysteine residue and on the other a lysine residue. Other useful cross-linkers include, without limitation, chemicals that link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-Maleimidobenzoyl-N-hydroxysuccinimide ester), an amino group and a carboxyl group (e.g., 4-[p-Azidosalicylamido]butylamine), and an amino group and a guanadium group that is present in the side chain of arginine (e.g., p-Azidophenyl glyoxal monohydrate).

The coupling moieties will preferably be at the termini (C or N) of each amino acid sequence. They can be, as indicated above, a cysteine residue on each amino acid sequence, or a cysteine on one and a lysine on the other. Where they are two cysteine residues, cross-linking can be effected by, for example, exposing amino acid sequences to oxidizing conditions.

A peptide can contain a first amino acid sequence and a second amino acid sequence or the peptide can contain more than one (e.g., two, three, four, five, six, seven, or eight or more) additional heterologous amino acid sequences. The additional heterologous amino acid sequences can flank, or be joined to, the amino terminus and/or the carboxy-terminus of the first amino acid sequence.

Where more than two amino acid sequences are to be joined, at least one of the amino acid sequences can have more than one cross-linking moiety. For example, a first amino acid sequence can have a cross-linking moiety at the amino-terminus and carboxy-terminus. Such multimers can be constructed "sequentially." Thus, each amino acid sequence is joined to the next such that the terminal amino acid sequences in the chain only have one residue involved in an inter-domain (or inter-agent) bond while the "internal" amino acid sequence(s) each have two moieties involved in inter-domain bonds. Alternatively, one amino acid sequence (such as the first amino acid sequence) could be linked to multiple (e.g., 2, 3, 4, or 5) other amino acid sequences.

Also featured are peptide compositions comprising: a first component and a second component, wherein the first component consists of, or consists essentially of, an amino acid sequence of SEQ ID NOS:1-18 as depicted in Table 1. The second component can be, e.g., a heterologous amino acid sequence (as described above), any other antigenic peptide (e.g., an XBP-1, CD138, or CS1 peptide other than those described herein, a detectable label (see below), a therapeutic agent, a diagnostic agent, or a prophylactic agent (see below). For example, a peptide composition can contain an amino acid sequence consisting of, or consisting essentially of, any one of SEQ ID NOS:1-18 and a detectable label such as a radionuclide.

It is understood that in some embodiments, a peptide of any one of SEQ ID NOS:1-18 can have at the amino-terminal end and/or carboxy-terminal end up to 200 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200) amino acids that are heterologous or are present in the native protein.

The peptides described herein can bind to a major histocompatibility complex (MHC) molecule (e.g., an MHC class I molecule or an MHC class II molecule). The "Major Histocompatibility Complex" or "MHC" is a cluster of genes that plays a role in control of the cellular interactions responsible for physiologic immune responses. In humans, the MHC is known as the HLA complex (see, e.g., Paul et al., FUNDAMENTAL IMMUNOLOGY, 3$^{rd}$ Edition, Raven Press, New York, (1993) and Stites, et al., IMMUNOLOGY, 8$^{th}$ Edition, Lange Publishing, Los Altos, Calif. (1994)).

An "HLA supertype or family," as used herein, refers to sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms. Types of HLA class I molecules include, e.g., HLA-A1, HLA-A2, HLA-A3, HLA-A24, HLA-B7, HLA-B27, HLA-B44, HLA-B58, or HLA-B62. Such HLA molecules are described in detail in U.S. Pat. No. 7,026,443, the entire disclosure of which is incorporated by reference in its entirety.

A peptide can bind to an MHC molecule with high affinity or intermediate affinity. As used herein, "high affinity" binding of a peptide to an HLA class I molecule is defined as a binding with a dissociation constant ($K_D$) of less than 50 (e.g., 45, 40, 35, 30, 25, 20, 15, 10, 5, 1, 0.5, 0.1, or less than 0.05) nM. "Intermediate affinity" is a binding of a peptide to an HLA class I molecule with a $K_D$ of between about 50 nM and about 500 nM (e.g., 55, 60, 65, 70, 75, 80, 85, 90, 95, 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nM). "High affinity" binding of a peptide to HLA class II molecules is defined as binding with a $K_D$ of less than 100 (e.g., 95, 90, 85, 80, 75, 70, 65, 60, 55, 50, 45, 40, 35, 30, 25, 20, 15, 10, 5, 1, 0.5, 0.1, or less than 0.05) nM. "Intermediate affinity" of a peptide for an HLA class II molecule is binding with a $K_D$ of between about 100 and about 1000 nM (e.g., 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nM). Methods for determining the binding affinity of a peptide and an MHC molecule are known in the art and set forth in the accompanying Examples. Suitable methods are also described in, e.g., U.S. Pat. No. 7,026,443.

The peptides described herein can also be, in association with an MHC molecule, recognized by an antigen specific T cell receptor on a T cell. A variety of suitable methods can be used to determine whether a peptide, in association with an MHC molecule, is recognized by a T cell receptor on a T cell. For example, peripheral blood lymphocytes (PBL) from normal subjects can be cultured with a test peptide in the presence of antigen presenting cells in vitro over a period of several weeks. T cells specific for the peptide become activated during this time and can be detected using, e.g., proliferation assays (carboxyfluoroscein succinimidyl ester (CFSE) assays of $^3$H-thymidine assays), limiting dilution assays, cytotoxicity assays (e.g., calcein-release assays), or cytokine- (e.g., IFNγ), lymphokine-, or $^{51}$Cr-release assays (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998, the disclosures of each of which are incorporated by reference in their entirety). A suitable in vivo method involves immunizating HLA transgenic mice, wherein peptides in adjuvant are administered subcutaneously to HLA transgenic mice and several weeks following immunization, splenocytes are removed and cultured in vitro in the presence of test peptide for approximately one week. peptide-specific T cells are detected using, e.g., a $^{51}$Cr-release assay (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997, the disclosures of each of which are incorporated by reference in their entirety). Suitable methods are also set forth in the accompanying Examples. For example, the activation of a T cell by a peptide (in the context of an MHC molecule) can be determined by a CD107 toxicity assay or calcein release assays (see, e.g., Examples 13 and 14).

Additionally, direct quantification of antigen-specific T cells can be performed by staining T cells with detectably-labeled MHC complexes such as any of the MHC molecule multimer compositions described herein (see below) or HLA-I tetramers (e.g., as described in Altman, J. D. et al., Proc. Natl. Acad. Sci. USA 90:10330, 1993 and Altman, J. D. et al., Science 274:94, 1996, the disclosures of each of which are incorporated by reference in their entirety).

In some embodiments, the peptides can be modified (e.g., amino acids of the peptides can be substituted) in order to modulate (e.g., increase or decrease) one of more properties of the peptides. For example, one or more (e.g., two, three, or four) amino acids of one of the peptides depicted in Table 1 can be substituted in order to increase the affinity of the peptide for an MHC molecule. In some embodiments, an amino acid of one of the peptides described herein (e.g., a T cell Receptor contacting amino acid residue of the peptide) can be modified in order to enhance a binding interaction between a T cell receptor and the peptide (in the context of an MHC molecule). Such modified peptides are often referred to as "altered peptide ligands." (See, e.g., Kalergis et al. (2000) J. Immunol. 165(1):280; Conlon et al. (2002) Science 1801; and International Publication No. WO02070003, the disclosure of each of which is incorporated by reference in their entirety).

Suitable methods for modifying the peptides as well as determining the effect of the modification are set forth in the accompanying Examples and are described in, e.g., Collins et al. (Immunlogical Reviews (1998) 163:151-160, the disclosure of which is incorporated by reference in its entirety).

Nucleic Acids and Methods for Producing the Peptides

The disclosure also features nucleic acid sequences (as well as nucleic acid vectors containing nucleic acid sequences) encoding, and methods for producing, one or more (e.g., one, two, three, four, five, six, seven, eight, nine, 10, 11, 12, 13, or 14) of any of the peptides described above. Such methods can include the steps of: optionally, providing a cell (or group of cells) comprising a nucleic acid vector containing a nucleic acid sequence encoding one of more of any of the peptides described herein, the nucleic acid sequence being operably linked to an expression control sequence, and culturing the cell under conditions that permit the expression of the peptides. The methods can also include the step of isolating the one or more peptides from the cell, or from the medium in which the cell was cultured.

Suitable methods for constructing nucleic acid sequences and vectors (e.g., expression vectors) for recombinant expression of one or more of the peptides described herein are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989, the disclosure of which is incorporated by reference in its entirety. The nucleic acids and vectors can be used, e.g., to express the peptides in a wide variety of host cells including, e.g., a bacterial, a yeast, or a mammalian cell. The nucleic acids and vectors can also be used in, e.g., in vivo and ex vivo methods as described below.

The peptide-coding sequences can be operably-linked to promoter and/or enhancer elements that direct the expression of the peptides encoded by the nucleic acids. Enhancers provide expression specificity in terms of time, location, and level. Unlike a promoter, an enhancer can function when located at variable distances from the transcription initiation site, provided a promoter is present. An enhancer can also be located downstream of the transcription initiation site or in an exon of the relevant gene. To bring a coding sequence under the control of a promoter, it is necessary to position the translation initiation site of the translational reading frame of the peptide between one and about fifty nucleotides downstream (3') of the promoter. Promoters of interest include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast α mating factors, the adenoviral E1b minimal promoter, or the thymidine kinase minimal promoter.

The peptide-coding sequences, or vectors containing the peptide-coding sequences, can contain a leader sequence that encodes a signal peptide. The leader sequence can be at the 5' end of the sequence encoding one or more of the peptides described herein. The signal peptide can be immediately N-terminal of a given peptides or can be separated from it by one or more (e.g., 2, 3, 4, 6, 8, 10, 15 or 20) amino acids, provided that the leader sequence is in frame with the nucleic acid sequence encoding the peptides. The signal peptide, which is generally cleaved from the peptide prior to secretion (unless of course the signal peptide directs the insertion of a transmembrane protein), directs the peptide to which it is attached into the lumen of the host cell endoplasmic reticulum (ER) during translation and the peptides are then secreted, via secretory vesicles, into the environment of the host cell. Useful signal peptides include, e.g., native leader sequences of cytokines or growth factors, KDEL (SEQ ID NO:23), or any signal sequences described in, e.g., U.S. Pat. No. 5,827,516, the disclosure of which is incorporated herein by reference in its entirety.

In some embodiments, the 5' end of a peptide-coding sequence can include a non-native ATG "start sequence." That is, e.g., an ATG sequence can be added to a nucleic acid encoding a peptide to ensure that the peptide is properly transcribed and translated. Although a leader sequence generally includes an ATG start sequence, in embodiments where it does not, the ATG sequence can be added at the 5' end of a nucleic acid encoding the leader sequence.

Suitable methods for constructing peptide-coding sequences and expression vectors are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated herein by reference in its entirety.

A recombinant vector can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) Proc. Nat. Acad. Sci. USA 75:1929; Ito et al. (1983) J. Bacteriol. 153:163; U.S. Pat. No. 4,879,231; and Sreekrishna et al. (1987) Gene 59:115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., supra).

Expression systems that can be used for small or large scale production of the peptides described herein include, but are not limited to, microorganisms such as bacteria (for example, *E. coli* and *B. subtilis*) transformed with recombinant bacteriophage DNA, plasmid DNA, or cosmid DNA expression vectors; fungus (e.g., yeast (for example, *Saccharomyces* and *Pichia*)) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid); or mammalian cell systems (for example, COS, CHO, BHK, 293, VERO, HeLa, MDCK, W138, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others).

As described above, following the expression of any of the peptides described herein, the peptides can be isolated from the cultured cells, or from the media in which the cells were cultured, using standard techniques (see Sambrook et al., supra). Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller peptides (e.g., peptides having less than 200 (e.g., less than 175, less than 150, less than 125, less than 100, less than 90, less than 80, less than 70, or less than 60) amino acids) can be chemically synthesized by standard chemical means such as FMOC solid-phase synthesis (see Example 1).

The peptides described herein can, but need not, be isolated. The term "isolated," as applied to any of the peptides described herein, refers to a peptide, a fragment thereof, (or for compositions, a macromolecular complex), that has been separated or purified from components (e.g., proteins or other naturally-occurring biological or organic molecules) which naturally accompany it. It is understood that recombinant molecules (e.g., recombinant peptides) will always be "isolated." Typically, a peptide (or fragment or macromolecular complex) is isolated when it constitutes at least 60%, by weight, of the total molecules of the same type in a preparation, e.g., 60% of the total molecules of the same type in a sample. For example, a peptide described herein is considered isolated when it constitutes at least 60%, by weight, of the total protein in a preparation or sample. In some embodiments, a molecule in the preparation consists of at least 75%, at least 90%, or at least 99%, by weight, of the total molecules of the same type in a preparation.

Similarly, the peptide-coding sequences or vectors containing the peptide-coding sequences described herein can also be isolated. The term "isolated," as applied to any of the peptide-coding sequences or vectors described herein, refers to a peptide-coding sequence or vector, a fragment thereof that has been separated or purified from components (e.g., nucleic acids, proteins, or other naturally-occurring biological or organic molecules) which naturally accompany it. It is understood that recombinant molecules (e.g., recombinant vectors or peptide-coding sequences) will always be "isolated." Typically, a peptide-coding sequence or vector (or fragment thereof) is isolated when it constitutes at least 60%, by weight, of the total molecules of the same type in a preparation, e.g., 60% of the total molecules of the same type in a sample. For example, a peptide-coding sequence or vector described herein is considered isolated when it constitutes at least 60%, by weight, of the total nucleic acid in a preparation or sample. In some embodiments, a molecule in the preparation consists of at least 75%, at least 90%, or at least 99%, by weight, of the total molecules of the same type in a preparation.

In some embodiments, the isolated peptides, peptide-coding sequences, or vectors can be frozen, lyophilized, or immobilized and stored under appropriate conditions, which allow the molecules to retain activity (e.g., the ability of a peptide to bind to an MHC molecule such as an MHC class I molecule or the ability of a vector to support expression of a peptide in a cell).

Additional Processing of the Peptides

Following the expression or synthesis of any of the peptides described herein, the peptides can be further processed. The further processing can include chemical or enzymatic modifications to peptides or, in cases where the peptides are modified, the processing can include enzymatic or chemical alterations of existing modifications, or both. The additional processing of the peptides can include the addition (covalent or non-covalent joining) of a heterologous amino acid sequence such as, but not limited to, any of the heterologous amino acid sequences described above. Enzymatic treatment can involve contacting a peptide with, e.g., one or more proteases, phosphatases, or kinases under conditions that allow the peptide to be modified. Enzymatic treatment can involve contacting a peptide with one or more enzymes (e.g., an oligosaccharyltransferase or a mannosidase) capable of glycosylating, or modifying the glycosylation of, the peptide.

The processing can include the addition of, e.g., a detectable label to a peptide. For example, a peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radionuclide (e.g., $^{3}H$, $^{32}P$, $^{33}P$, $^{125}I$, or $^{35}S$).

The processing can also involve the coupling of the peptide to a polymer (e.g., a polyalkylene glycol moiety such as a polyethylene glycol moiety). In some embodiments, the polymer is coupled to the polypeptide at a site on the peptide that is an N terminus. In some embodiments, a peptide can contain one or more internal amino acid insertions that provide an internal polymer conjugation site to which a polymer can be conjugated.

Pharmaceutical Compositions

Any of the peptides and nucleic acids encoding the peptides described herein can be incorporated into pharmaceutical compositions. Such compositions typically include one or more of the peptides (and/or nucleic acids encoding the peptides) and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. One or more peptides can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds (e.g., one or more chemotherapeutic agents) can also be incorporated into the compositions.

A pharmaceutical composition is generally formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the pharmaceutical composition must be sterile and should be fluid to the extent that easy syringability exists. It should be stable under the conditions of manufacture and storage and must be preserved against any contamination by microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating one or more of the peptides (or one or more the nucleic acids encoding the peptides) in the required amount in an appropriate solvent with one or a combination of ingredients enumerated above, as required, followed by filtered sterilization. Generally, dispersions are prepared by incorporating the peptide(s) (or nucleic acid(s) encoding the peptide(s)) into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the one or more peptides can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

The powders and tablets can contain from 1% to 95% (w/w) of an individual peptide or a mixture of two or more peptides. In certain embodiments, the peptide can range from about 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the peptide (or nucleic acid) with encapsulating material as a carrier providing a capsule in which the peptide with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the peptides or nucleic acids can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the peptides or nucleic acids can be formulated into ointments, salves, gels, or creams as generally known in the art.

The peptides or nucleic acids can also be prepared in the form of suppositories (e.g., with conventional suppository bases such as cocoa butter and other glycerides) or retention enemas for rectal delivery.

In one embodiment, the peptides or nucleic acids can be prepared with carriers that will protect the peptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to, e.g., APCs with monoclonal antibodies to APC-specific antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form, as used herein, refers to physically discrete units suited as unitary dosages for the subject to be treated; each unit containing a predetermined quantity of the peptides (or nucleic acids) calculated to produce the desired therapeutic effect in association with the required pharmaceutical carrier. Dosage units can also be accompanied by instructions for use.

The nucleic acid molecules encoding the peptides can be inserted into vectors and used as gene therapy vectors (as described above). Gene therapy vectors can be delivered to a subject by, for example, intravenous injection, local administration (see, e.g., U.S. Pat. No. 5,328,470) or by stereotactic injection (see, e.g., Chen, et al. (1994) Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system (see below under "Ex Vivo Methods").

Additional examples of gene delivery vehicles include, but are not limited to, liposomes, biocompatible polymers, including natural polymers and synthetic polymers; lipoproteins; polypeptides; polysaccharides; lipopolysaccharides; artificial viral envelopes; metal particles; bacteria; viruses such as baculovirus, adenovirus, and retrovirus; bacteriophage; cosmids; plasmids; fungal vectors and other recombination vehicles typically used in the art which have been described for expression in a variety of eukaryotic and prokaryotic hosts, and may be used for gene therapy as well as for simple protein expression.

Examples of viral vectors include retroviral vectors, adenovirus vectors, adeno-associated virus vectors, alphavirus vectors and the like. Liposomes that comprise a targeting moiety such as an antibody or fragment thereof can also be used to prepare pharmaceutical compositions of nucleic acids for delivery to a subject.

Any of the pharmaceutical compositions described herein can be included in a container, pack, or dispenser together with instructions for administration as described below.

MHC Molecule Multimer Compositions and Methods for Using the Compositions

The disclosure also features compositions comprising: (i) one or more of any of the peptides described above and (ii) a major histocompatibility complex (MHC) molecule multimer. The multimer contains two or more (e.g., three, four, five, six, seven, eight, nine, or 10 or more) entire MHC molecules or peptide-binding regions of an MHC molecule. The one or more peptides can be associated with (e.g., covalently or non-covalently bound to) the MHC molecule multimer.

An MHC molecule of the multimer can be an MHC class I molecule (e.g., an HLA-A2 molecule) or an MHC class II molecule. The MHC molecule can be a mammalian (e.g., a rodent, a non-human primate, a human, or any other mammal described herein) MHC molecule.

The two or more MHC molecules (or the peptide-binding regions of the MHC molecules) in the multimer can be from the same MHC molecule or from different MHC molecules. For example, an MHC molecule multimer can contain five MHC molecules, three of which are the same MHC molecules and two of which are different from the first three. In another example, each MHC molecule of the multimer is different. At least one of the MHC molecules can bind to at least one of the peptides.

In some embodiments, the above compositions can contain at least two (e.g., two, three, four, five, six, seven, eight, nine, 10, 11, or 15 or more) of any of the peptides described herein.

The compositions can also be associated with a detectable label. For example, one or more of the MHC molecules of the multimer can be covalently or non-covalently bound to a detectable label. Suitable detectable labels (e.g., enzymes, fluorescent materials, luminescent materials, bioluminescent materials, or radionuclides) as well as methods for joining detectable labels to a peptide or an MHC molecule are described above.

An MHC multimer composition can be generated using a peptide described above as follows: a peptide that binds to an HLA molecule is refolded in the presence of the corresponding HLA heavy chain and $\beta_2$-microglobulin to generate a trimolecular complex. The complex is then biotinylated at the carboxyl terminal end of the heavy chain at a site that was previously engineered into the heavy chain. Multimer formation is then induced by the addition of streptavidin.

As T cell receptors are capable of recognizing a specific peptide-MHC complex on a target cell among a wide variety of other peptide-MHC complexes, the MHC multimer compositions described herein can be used to, e.g., detect antigen-specific T cells in a population of unrelated T cells (see below). For such assays, the multimers will generally be detectably labeled (see above).

For example, a multimeric MHC molecule/peptide complex can be used in an assay to assess peripheral blood mononuclear cells for the presence of antigen-specific CTL following exposure to an immunogen. The MHC multimer complex can be used to directly visualize antigen-specific CTL (see, e.g., Ogg et al., Science 279:2103-2106, 1998; and Altman et al., Science 174:94-96, 1996) and determine the frequency of the antigen-specific CTL population in a sample of peripheral blood mononuclear cells. In one example, a detectably-labeled streptavidin used to multimerize the MHC multimer can be used to label T cells that bind to the MHC molecule/peptide complexes of the multimer. To do this, cells treated with the multimer are exposed, e.g., to a label (e.g., a fluorophore conjugated to biotin). The cells can then be readily isolated or detected, e.g., using flow cytometry.

Applications

The peptides (and pharmaceutical compositions thereof), MHC multimer containing compositions, kits, and articles of manufacture described herein can be used in a variety of methods. For example, the peptides can be used to: (i) induce an immune response in a subject (e.g., a subject with a cancer); (ii) activate a T cell in culture; and/or (iii) treat or event prevent a cancer such as multiple myeloma or Waldenstrom's macroglobulinemia. As described above, the MHC multimer containing compositions can be used to, e.g., detect antigen-specific T cells in a population of unrelated T cells.

While the utility of the peptides (or pharmaceutical compositions thereof), MHC multimer containing compositions, kits, or articles of manufacture is in no way limited to any of the particular embodiments described herein, exemplary methods in which these reagents can be used are provided below.

Methods for Inducing an Immune Response

The disclosure also features a variety of methods for inducing an immune response in a subject. The methods for inducing an immune response in a subject can include the step of administering to a subject one or more of any of peptides (or expression vectors containing nucleic acid sequences encoding the peptides) described herein (or any of the pharmaceutical compositions containing one or more peptides (or vectors) described herein). Any of the peptides described herein can be used to stimulate an immune response by use of a nucleic acid expression system that encodes one or more of the peptides described herein. That is, methods for inducing an immune response in a subject can include the step of administering to a subject an expression vector containing nucleic acid sequences encoding one or more of the peptides described herein (or a pharmaceutical composition containing the expression vector). The immune response can be a CD8$^+$ T cell, a CD4$^+$ T cell, a cytotoxic T lymphocyte (CTL), a $T_H1$ response, a $T_H2$ response, or a combination of both types of responses.

Any of the above methods can also be, e.g., methods for treating or preventing (prophylaxis against) a cancer (e.g., plasma cell disorder such as multiple myeloma, Waldenstrom's macroglobulinemia, or any other cancer expressing XBP1, CD138, or CS1) in a subject. When the terms "prevent," "preventing," or "prevention" are used herein in connection with a given treatment for a given condition, they mean that the treated subject either does not develop a clinically observable level of the condition at all (e.g., the subject does not exhibit one or more symptoms of the condition or, in the case of a cancer, the subject does not develop a detectable level of the cancer), or the condition develops more slowly and/or to a lesser degree (e.g., fewer symptoms or lower numbers of cancer cells in the subject) in the subject than it would have absent the treatment. These terms are not limited solely to a situation in which the subject experiences no aspect of the condition whatsoever. For example, a treatment will be said to have "prevented" the condition if it is given during, e.g., during an early diagnosis of a cancer (e.g., the detection of a few cancer cells in a sample from the subject) that would have been expected to produce a given manifestation of the condition (an advanced cancer), and results in the subject's experiencing fewer and/or milder symptoms of the condition than otherwise expected. A treatment can "prevent" a cancer (e.g., a plasma cell disorder such as multiple myeloma or Waldenstrom's macroglobulinemia) when the subject displays only mild overt symptoms of the cancer. "Prevention" does not imply that there must have been no development of even a single cancer cell by a subject so treated.

Generally, a peptide delivered to the subject will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily (see below).

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted reagent production cells). See, e.g., U.S. Pat. Nos. 4,407,957, 5,798,113 and 5,800,828, each incorporated herein by reference in their entirety.

Conventional and pharmaceutically acceptable routes of administration of a therapeutic nucleic acid include, but are not necessarily limited to, intramuscular, subcutaneous, intradermal, transdermal, intravenous, rectal (e.g., enema, suppository), oral, intragastric, intranasal and other routes of effective inhalation routes, and other parenteral routes of administration. Routes of administration may be combined, if desired, or adjusted depending upon the nucleic acid molecule and/or the desired effect on the immune response. Methods for administering a nucleic acid to a subject can include a variety of well-known techniques such as vector-mediated gene transfer (e.g., viral infection/transfection, or various other protein-based or lipid-based gene delivery complexes) as well as techniques facilitating the delivery of "naked" polynucleotides (such as electroporation, "gene gun" delivery, and various other techniques used for the introduction of polynucleotides to a subject or a cell of a subject).

In general, the dosage of a peptide or a nucleic acid required depends on the choice of the route of administration; the nature of the formulation; the nature or severity of the subject's illness; the immune status of the subject; the subject's size, weight, surface area, age, and sex; other drugs being administered; and the judgment of the attending medical professional.

Suitable dosages of peptide for inducing an immune response are in the range of 0.000001 to 10 mg of the reagent or antigenic/immunogenic composition per kg of the subject. Wide variations in the needed dosage are to be expected in view of the variety of reagents and the differing efficiencies of various routes of administration. For example, nasal or rectal administration may require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). For example, a peptide can be administered as an initial immunization and then administered one or more times subsequently as a booster immunization.

The dose of nucleic acid administered to a subject, in the context of the methods described herein, should be sufficient to effect a beneficial therapeutic response in the subject over time, or to alleviate symptoms. Although the dosage used will vary depending on, e.g., the subject or the clinical goals to be achieved (see below), a suitable dosage range is one which provides up to about 1 µg, to about 1,000 µg, to about 5,000 µg, to about 10,000 µg, to about 25,000 µg or about 50,000 µg of nucleic acid per ml of carrier in a single dosage.

In order to optimize therapeutic efficacy (e.g., the efficacy of the one or more peptides or the nucleic acids encoding the peptides to induce an immune response in a subject), compositions containing the peptides or nucleic acids can be first administered at different dosing regimens. The unit dose and regimen depend on factors that include, e.g., the species of mammal, its immune status, the body weight of the mammal.

The frequency of dosing for a pharmaceutical composition (e.g., a pharmaceutical composition containing one or more peptides or one or more nucleic acid sequences encoding one or more of the peptides described herein) is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status.

In some embodiments, a pharmaceutical composition can be administered to a subject at least two (e.g., three, four, five, six, seven, eight, nine, 10, 11, 12, 15, or 20 or more) times. For example, a pharmaceutical composition can be administered to a subject once a month for three months; once a week for a month; once a year for three years, once a year for five years; once every five years; once every ten years; or once every three years for a lifetime.

In some embodiments, the reagent can be administered with an immune modulator such as a Toll Receptor ligand or an adjuvant (see below).

As defined herein, a "therapeutically effective amount" of a peptide or a nucleic acid encoding a peptide is an amount of the peptide or nucleic acid that is capable of producing an immune response in a treated subject. A therapeutically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A therapeutically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

As defined herein, a "prophylactically effective amount" of a peptide or nucleic acid encoding a peptide is an amount of the peptide or nucleic acid that is capable of producing an immune response against a cancer cell (e.g., a multiple myeloma or Waldenstrom's macroglobulinemia cell) in a treated subject, which immune response is capable of preventing the development of a cancer in a subject or is able to substantially reduce the chance of a subject developing or continue developing a cancer (see above). A prophylactically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A prophylactically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

The subject can be any animal capable of an immune response to an antigen such as, but not limited to, a mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. The subject can be one having, suspected of having, or at risk of developing a cancer such as multiple myeloma, Waldenstrom's macroglobulinemia, or any other type of cancer that expresses XBP1, CD138, or CS1. The subject can be one in remission from multiple myeloma or Waldenstrom's macroglobulinemia.

The methods can also include the step of, prior to administering the one or more peptides (or nucleic acids) to the subject, determining whether one or more cancer cells of the subject's cancer (e.g., a plasma cell disorder such as multiple myeloma or Waldenstrom's macroglobulinemia) express XBP1, CD138, or CS1. Expression of these proteins includes both mRNA and protein expression. Methods for detecting protein and mRNA expression in a cell are known in the art and include, e.g., enzyme-linked immunosorbent assay (ELISA), western and dot-blotting techniques, or immuno-histochemistry techniques for detecting protein and reverse transcription-polymerase chain reaction (RT-PCR) or northern-blotting techniques for detecting mRNA. (See Sambrook et al., supra).

The methods can also include the step of administering to the subject one or more chemotherapeutic agents, one or more forms of ionizing radiation, or one or more immunomodulatory agents. The one or more forms of ionizing radiation can be gamma-irradiation, X-irradiation, or beta-irradiation. The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, thalidomide, lenalidomide, a proteosome inhibitor (e.g., bortezomib), an hsp90 inhibitor (e.g., tenespinmycin), transplatinum, 5-fluorouracil, vincristin, vinblastin, methotrexate, or an analog of any of the aforementioned. Immunomodulatory agents include, e.g., a variety of chemokines and cytokines such as Interleukin 2 (IL-2), granulocyte/macrophage-colony stimulating factor (GM-CSF), and Interleukin 12 (IL-12).

The subject can have, be suspected of having, or be at risk of developing a cancer such as multiple myeloma or Waldenstrom's macroglobulinemia. A subject "suspected of having a cancer" is one having one or more symptoms of a cancer. Symptoms of cancer are well-known to those of skill in the art and generally include, without limitation, pain, weight loss, weakness, excessive fatigue, difficulty eating, loss of appetite, chronic cough, worsening breathlessness, coughing up blood, blood in the urine, blood in stool, nausea, vomiting, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, difficulty swallowing, and the like. Symptoms of multiple myeloma specifically include, e.g., bone pain (e.g., in the back or ribs), high levels of calcium in the blood, excessive thirst or urination, constipation, nausea, loss of appetite, confusion, weakness or numbness in the legs, weight loss, or repeated infections. Symptoms indicative of Waldenstrom's macroglobulinemia include, e.g., weakness, swollen lymph nodes, severe fatigue, nose bleeds, weight loss, neurological problems.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC), has been exposed to conditions, or is presently affected by conditions, that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, 4-aminobiphenyl, aromatic amines, benzene, benz{a}anthracene, benzo{a}pyrene, formaldehyde, hydrazine, Polonium-210 (Radon), urethane, or vinyl chloride). The subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. In addition, a subject can be "at risk of developing a cancer" when the subject suffers from an inflammation (e.g., chronic inflammation). A subject can be at risk of developing multiple myeloma if, e.g., the subject has monoclonal gammopathy of undetermined significance (MGUS).

From the above it will be clear that subjects "suspected of having a cancer" or "at risk of developing a cancer" are not all the subjects within a species of interest.

In some embodiments, the method can also include determining if an immune response occurred in a subject after administering the peptide(s) or nucleic acids to the subject. Suitable methods for determining whether an immune response occurred in a subject include use of immunoassays to detect, e.g., the presence of antibodies specific for a peptide in a biological sample from the subject. For example, after the administration of the peptide to the subject, a biological sample (e.g., a blood sample) can be obtained from the subject and tested for the presence of antibodies specific for the peptide(s). An immune response can also be detected by assaying for the presence or amount of activated T cells in a sample. Such assays include, e.g., proliferation assays, limiting dilution assays, cytotoxicity assays (e.g., lymphokine- or $^{51}$Cr-release assays) (as described above).

In some embodiments, the methods can also include the step of determining whether a subject has a cancer. Suitable methods for such a determination depend on the type of cancer to be detected in the subject, but are known in the art. Such methods can be qualitative or quantitative. For example, a medical practitioner can diagnose a subject as having multiple myeloma when the subject exhibits two or more (e.g., three, four, five, or six or more) symptoms of multiple myeloma such as any of those described herein. A subject can also be determined to have multiple myeloma by measuring the blood calcium level, the white or red blood cell count, or the amount of protein in the urine of a subject.

Ex Vivo Approaches.

An ex vivo strategy for inducing an immune response in a subject can involve contacting suitable APCs (e.g., dendritic cells, monocytes, or macrophages) obtained from the subject with any of the peptides described herein. Alternatively, the cells can be transfected with a nucleic acid (e.g., an expression vector) encoding one or more of the peptides and optionally cultured for a period of time and under conditions that permit the expression of the peptides. The transfection method will depend on the type of cell and nucleic acid being transfected into the cell. (See above under "Nucleic Acids and Methods for Producing the Peptides" and also Sambrook et al., supra). Following the contacting or transfection, the cells are then returned to the subject.

The cells can be any of a wide range of types expressing MHC class I or II molecules. For example, the cells can include bone marrow cells, macrophages, monocytes, dendritic cells, T cells (e.g., T helper cells, CD4$^+$ cells, CD8$^+$ cells, or cytotoxic T cells), or B cells.

Ex vivo methods for stimulating an immune response can include contacting in vitro a T cell (e.g., in a population of lymphocytes obtained from a subject) with an antigen-presenting cell expressing an MHC molecule bound to one of the peptides described herein for an amount of time (and under conditions) that is sufficient to activate the T cell. Following the contacting, the activated T cell(s) are reintroduced into the subject from which the cells were obtained. Methods for generating an APC expressing an MHC molecule bound to one of the peptides described herein are set forth above in this section.

In some embodiments of any of the ex vivo methods, cells can be obtained from a subject of the same species other than the subject (allogeneic) can be contacted with the reagents (or immunogenic/antigenic compositions) and administered to the subject.

Methods for Producing an Antibody in a Subject

Methods of producing an antibody specific for an immunogen (e.g., one or more of any of the peptides described herein) are known in the art and detailed below. For example, antibodies or antibody fragments specific for a peptide described herein can be generated by immunization, e.g., using an animal, or by in vitro methods such as phage display. All or part of a peptide described herein can be used to generate an antibody or antibody fragment.

A peptide can be used to prepare antibodies by immunizing a suitable subject, (e.g., rabbit, goat, mouse, or other mammal such as a human) with the peptide. An appropriate immunogenic preparation can contain, for example, any of the reagents described herein. The preparation can further include an adjuvant, such as Freund's complete or incomplete adjuvant, alum, RIBI, or similar immunostimulatory agent. Adjuvants also include, e.g., cholera toxin (CT), *E. coli* heat labile toxin (LT), mutant CT (MCT) (Yamamoto et al. (1997) J. Exp. Med. 185:1203-1210) and mutant *E. coli* heat labile toxin (MLT) (Di Tommaso et al. (1996) Infect. Immunity 64:974-979). MCT and MLT contain point mutations that substantially diminish toxicity without substantially compromising adjuvant activity relative to that of the parent molecules. Immunization of a suitable subject with an immunogenic peptide preparation (e.g., any of the reagents described herein) induces a polyclonal anti-peptide antibody response.

The term antibody as used herein refers to immunoglobulin molecules and immunologically active portions of immunoglobulin molecules (i.e., molecules that contain an antigen binding site that specifically binds to the peptide (e.g., a peptide described herein)). An antibody that specifically binds to a peptide described herein is an antibody that binds the peptide, but does not substantially bind other molecules in a sample. Examples of immunologically active portions of immunoglobulin molecules include, e.g., F(ab) fragments, F(ab')$_2$ fragments, or any other antibody fragments described herein (see below).

The anti-peptide antibody can be a monoclonal antibody or a preparation of polyclonal antibodies. The term monoclonal antibody, as used herein, refers to a population of antibody molecules that contain only one species of an antigen binding site capable of immunoreacting with the peptide. A monoclonal antibody composition thus typically displays a single binding affinity for a particular peptide with which it immunoreacts.

Polyclonal anti-peptide antibodies can be prepared as described above by immunizing a suitable subject with a peptide immunogen. The anti-peptide antibody titer in the immunized subject can be monitored over time by standard techniques, such as with an enzyme linked immunosorbent assay (ELISA) using immobilized peptide. If desired, the antibody molecules directed against the peptide can be isolated from the mammal (e.g., from the blood) and further purified by techniques such as protein A chromatography to obtain the IgG fraction. At an appropriate time after immunization, e.g., when the anti-peptide antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), or the EBV-hybridoma technique (Cole et al. (1985), Monoclonal Antibodies and Cancer Therapy, Alan R. Liss, Inc., pp. 77-96). Any of the many well known protocols used for fusing lymphocytes and immortalized cell lines can be applied for the purpose of generating an anti-peptide monoclonal antibody (see, e.g., Current Protocols in Immunology, supra; Galfre et al. (1977) Nature 266: 55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402, the disclosures of each of which are incorporated by reference in their entirety).

As an alternative to preparing monoclonal antibody-secreting hybridomas, a monoclonal anti-peptide antibody can be identified and isolated by screening a recombinant combinatorial immunoglobulin library (e.g., an antibody phage display library) with a peptide described herein to isolate immunoglobulin library members that bind the peptide.

An anti-peptide antibody (e.g., a monoclonal antibody) can be used to isolate the peptide by techniques such as affinity chromatography or immunoprecipitation. Moreover, an anti-peptide antibody can be used to detect the peptide in screening assays described herein. An antibody can optionally be coupled to a detectable label such as any of those described herein or a first or second member of a binding pair (e.g., streptavidin/biotin or avidin/biotin), the second member of which can be conjugated to a detectable label.

Non-human antibodies to a target peptide (e.g., a peptide described herein) can also be produced in a non-human host (e.g., a rodent) and then humanized, e.g., as described in U.S. Pat. No. 6,602,503, EP 239 400, U.S. Pat. No. 5,693,761, and U.S. Pat. No. 6,407,213, the disclosures of each of which are incorporated by reference in their entirety.

EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al. (1988) Nature 332, 323-327; Verhoeyen et al. (1988) Science 239, 1534-1536, the disclosures of each of which is incorporated by reference in their entirety. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al. (1991) Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (e.g., at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213, the disclosure of which is incorporated herein by reference in its entirety.

Fully human monoclonal antibodies that bind to a target peptide can be produced, e.g., using in vitro-primed human splenocytes, as described by Boerner et al. (1991) J. Immunol., 147, 86-95. They may be prepared by repertoire cloning as described by Persson et al., 1991, Proc. Nat. Acad. Sci. USA, 88: 2432-2436 or by Huang and Stollar (1991) J. Immunol. Methods 141, 227-236; also U.S. Pat. No. 5,798,230, the disclosures of each of which are incorporated herein by reference in their entirety. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; U.S.

Patent Application Publication No. 2003-0232333, the disclosures of each of which are incorporated by reference in their entirety).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a peptide that includes an immunoglobulin variable domain sequence can associate with another immunoglobulin variable domain sequence to form a target binding structure (or "antigen binding site"), e.g., a structure that interacts with a target peptide.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1 CH2 and CH3 and a hinge region. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment. In some embodiments, to humanize a murine antibody, one or more regions of a mouse Ig loci can be replaced with corresponding human Ig loci (see, e.g., Zou et al. (1996) The FASEB Journal Vol 10, 1227-1232; Popov et al. (1999) J. Exp. Med. 189(10) 1611-1619; and Nicholson et al. (1999) J. Immunol. 6898-6906; the disclosures of each of which are incorporated by reference in their entirety.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762, the disclosures of each of which are incorporated herein by reference in their entirety. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 kDa or 214 amino acids) are encoded by a variable region gene at the NH2-terminus (about 110 amino acids) and a kappa or lambda constant region gene at the COOH-terminus. Full-length immunoglobulin "heavy chains" (about 50 kDa or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to a fragment of a full-length antibody that retain the ability to specifically bind to a target of interest. Examples of binding fragments encompassed within the term "antigen-binding fragment" of a full length antibody include: (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scF$_v$). (See e.g., Bird et al. (1988) Science 242:423-426; and Huston et al. (1988) Proc. Natl. Acad. Sci. USA 85:5879-5883, the disclosures of each of which are incorporated herein by reference in their entirety).

Antibodies

An isolated antibody or antigen-binding fragment thereof produced by the methods described herein can selectively bind to the an epitope within or overlapping the amino acid sequence of any of SEQ ID NOS:1-18. The antibody can also be one that crossblocks the binding of antibody that binds to an epitope within or overlapping the amino acid sequence of any of SEQ ID NOS:1-18. Typically, binding of an antibody to an epitope is considered selective when the antibody binds with a $K_D$ of less than $10^{-6}$M. If necessary, nonspecific binding can be reduced without substantially affecting selective binding by varying the binding conditions. An antibody that "crossblocks" or a "crossblocking antibody" refers to a first antibody that, when bound to a epitope (e.g., one contained within or overlapping any of SEQ ID NOS:1-18), reduces or eliminates the ability of a second antibody to bind to the peptide (relative to binding of the second antibody to the peptide that occurs in the absence of the first antibody).

It is understood that an antibody produced by a method described herein (e.g., an antibody specific for one or more of the peptides described herein) can be used to, e.g., detect a cancer cell expressing XBP1, CD138, or CS1 and thus is useful in many exemplary methods described herein.

Methods for Selecting a Therapy

Methods for selecting a therapy for a subject with a cancer (e.g., a plasma cell disorder such as multiple myeloma and/or Waldenstrom's macroglobulinemia or any cancer in which XBP1, CD138, or CS1 are expressed) include the steps of: optionally, determining whether one or more cells (e.g., plasma cells) of a subject's cancer express XBP1; and if one or more cells express XBP1, selecting as a therapy for the subject a composition containing at least one peptide comprising the amino acid sequence of any one of SEQ ID NOS: 1-10. As described above, the amino acid sequence can be at least 66% identical to, or contain not more than 4 substitutions of, the amino acid sequence of any of SEQ ID NOS:1-10, provided that the amino acid sequence is capable of: (i) inducing in the subject an immune response; (ii) binding to an MHC molecule; and (iii) being recognized, in the context of an MHC molecule, by a T cell receptor on a T cell. The peptide can also be one comprising: a first amino acid sequence consisting essentially, or consisting, of any one of SEQ ID NOS:1-10 as depicted in Table 1; and a second amino acid sequence that is heterologous to the first amino acid sequence.

Methods for selecting a therapy for a subject with a cancer can include the steps of: optionally, determining whether one or more cells (e.g., plasma cells) of a subject's cancer express CD138; and if one or more cells express CD138, selecting as a therapy for the subject a composition containing at least peptide comprising the amino acid sequence of any one of SEQ ID NOS:11-14. As described above, the amino acid sequence can be at least 66% identical to, or contain not more than 4 substitutions of, the amino acid sequence of any of SEQ ID NOS:11-14, provided that the amino acid sequence is capable of: (i) inducing in the subject an immune response; (ii) binding to an MHC molecule; and (iii) being recognized, in the context of an MHC molecule, by a T cell receptor on a T cell. The peptide can also be one comprising: a first amino acid sequence consisting essentially, or consisting, of any one of SEQ ID NOS:11-14 as depicted in Table 1; and a second amino acid sequence that is heterologous to the first amino acid sequence.

Methods for selecting a therapy for a subject with a cancer can include the steps of: optionally, determining whether one or more cells (e.g., plasma cells) of a subject's cancer express CS1; and if one or more cells express CS1, selecting as a therapy for the subject a composition containing at least peptide comprising the amino acid sequence of any one of SEQ ID NOS:15-18. As described above, the amino acid sequence can be at least 66% identical to, or contain not more than 4 substitutions of, the amino acid sequence of any of SEQ ID NOS:15-18, provided that the amino acid sequence is capable of: (i) inducing in the subject an immune response; (ii) binding to an MHC molecule; and (iii) being recognized, in the context of an MHC molecule, by a T cell receptor on a T cell. The peptide can also be one comprising: a first amino acid sequence consisting essentially, or consisting, of any one of SEQ ID NOS:15-18 as depicted in Table 1; and a second amino acid sequence that is heterologous to the first amino acid sequence.

It is understood that where one or more cells (e.g., plasma cells) of a subject's cancer express two or more of XBP1, CD138, and CS1, a combination of suitable peptides can be delivered to the subject. For example, where one or more cells (e.g., plasma cells) of a subject's cancer are determined to express XBP1 and CD138, the methods for selecting a therapy can include selecting as a therapy for the subject: (a) a combination of a composition containing at least one peptide comprising the amino acid sequence of any one of SEQ ID NOS:1-10 and a composition containing at least one peptide comprising the amino acid sequence of any one of SEQ ID NOS:11-14; or (ii) a composition comprising at least one peptide comprising the amino acid sequence of any one of SEQ ID NOS:1-10 and at least one peptide comprising the amino acid sequence of any one of SEQ ID NOS:11-14.

Methods for determining whether one or more cells express XBP1, CD138, or CS1 are known in the art and described above. For example, a biological sample (e.g., a blood sample or lymph node tissue sample) obtained from a subject can be tested using an XBP1-, CD138-, or CS1-specific antibody made by a method described herein to detect the presence or amount of an XBP1, CD138, or CS1 polypeptide expressed by a cell (or cell lysate). (See, e.g., the working Examples and Sambrook et al., supra). Methods for assaying a biological sample for the presence or amount of a polypeptide include, e.g., ELISA, immunohistochemistry, flow cytometry, western-blotting, or dot-blotting assays.

In some embodiments, any of the methods described herein can also include the step of providing a biological sample from a subject and/or obtaining a biological sample from a subject. Suitable biological samples for the methods described herein include any biological fluid, cell, tissue, or fraction thereof, which includes analyte proteins of interest (e.g., XBP1, CD138, or CS1 proteins). A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a cell-containing biological fluid such as urine, blood, plasma, serum, saliva, semen, sputum, cerebral spinal fluid, tears, mucus or an aspirate (e.g., a lung or breast nipple aspirate), or such a sample absorbed onto a paper or polymer substrate. A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of sample types from a subject such as a combination of a tissue and biological fluid.

The biological samples can be obtained from a subject, e.g., a subject having, suspected of having, or at risk of developing, a cancer (e.g., multiple myeloma and/or Waldenstrom's macroglobulinemia). Any suitable methods for obtaining the biological samples can be employed, although exemplary methods include, e.g., phlebotomy, swab (e.g., buccal swab), aspiration, or fine needle aspirate biopsy procedure. Non-limiting examples of tissues susceptible to fine needle aspiration include lymph node, lung, thyroid, breast, and liver. Samples can also be collected, e.g., by microdissection (e.g., laser capture microdissection (LCM) or laser microdissection (LMD)), bladder wash, smear (PAP smear), or ductal lavage.

After detecting a cancer (e.g., multiple myeloma and/or Waldenstrom's macroglobulinemia) in a subject, e.g., using a method described above, a medical practitioner (e.g., a doctor) can select an appropriate therapeutic modality for the subject (e.g., a therapy comprising one or more of the peptides described herein) by, e.g.: (i) writing a prescription for a medicament; (ii) giving (but not necessarily administering) a medicament to a subject (e.g., handing a sample of a prescription medication to a patient while the patient is at the physician's office); (iii) communication (verbal, written (other than a prescription), or electronic (email, an electronic post to a secure site)) to the patient of the suggested or recommended therapeutic modality (e.g., a therapy comprising one or more of the peptides described herein); or (iv) identifying a suitable therapeutic modality for a subject and disseminating the information to other medical personnel, e.g., by way of patient record. The latter (iv) can be useful in a case where, e.g., more than one therapy or therapeutic agent are to be administered to a patient by different medical practitioners.

After detecting the presence or amount of XBP1, CD138, or CS1 in a subject (using any of the methods above); and/or selecting a therapy for the subject, a medical practitioner (e.g., a doctor) can administer the appropriate therapeutic modality to the subject. Methods for administering a therapy comprising one or more of the peptides described herein as detailed above.

In addition, a medical practitioner can also select, prescribe and/or administer one or more additional therapeutic agents to treat a cancer or one or more medicaments to treat side-effects of an anti-cancer agent. Suitable chemotherapeutic agents for treating multiple myeloma and/or Waldenstrom's macroglobulinemia include, e.g., melphalan, cyclophosphamide, vincristine, doxorubicin, prednisone, dexamethasone, proteosome inhibitors (e.g., bortezomib), thalidomide, or lenalidomide.

Side effects of anti-cancer agents include, e.g., anemia, gastrointestinal symptoms (e.g., nausea, vomiting, diarrhea), leukopenia (decreased number of white blood cells, which may cause infection), temporary hair loss, or thrombocytopenia (decreased number of platelets, which may cause bleeding). Thus, a doctor can prescribe or administer to a subject a chemotherapeutic agent such as vincristine along with an anti-anemia medicament such as epoetin alpha (e.g., Procrit® or Epogen®).

Kits and Articles of Manufacture

The disclosure also features a variety of kits. The kits can include, e.g., one or more (e.g., one, two, three, four, five, six, seven, eight, nine, or 10 or more) of any of the peptides (or expression vectors containing nucleic acid sequences encoding one or more peptides) described herein; and instructions for administering the peptide to a subject. The kit can include one or more pharmaceutically acceptable carriers and/or one or more immune stimulating agents. The immune stimulating agents can be, e.g., a T helper epitope, an altered peptide ligand, or an adjuvant.

The kits can also contain one or more therapeutic agents, diagnostic agents, or prophylactic agents. The one or more therapeutic, diagnostic, or prophylactic agents include, but are not limited to: (i) an agent that modulates inflammatory responses (e.g., aspirin, indomethacin, ibuprofen, naproxen, steroids, cromolyn sodium, or theophylline); (ii) an agent that affects renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, or mevalonate); (iii) drugs that affect gastrointestinal function (e.g., omeprazole or sucralfate); (iv) antibiotics (e.g., tetracycline, clindamycin, amphotericin B, quinine, methicillin, vancomycin, penicillin G, amoxicillin, gentamicin, erythromycin, ciprofloxacin, doxycycline, streptomycin, gentamicin, tobramycin, chloramphenicol, isoniazid, fluconazole, or amantadine); (v) anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, or decarbazine); (vi) immunomodulatory agents (e.g., interleukins, interferons (e.g., interferon gamma (IFN-γ), granulocyte macrophage-colony stimulating factor (GM-CSF), tumor necrosis factor alpha (TNFα), tumor necrosis factor beta (TNFβ), cyclosporine, FK506, azathioprine, steroids); (ix) drugs acting on the blood and/or the blood-forming organs (e.g., interleukins, G-CSF, GM-CSF, erythropoietin, heparin, warfarin, or coumarin); or (vii) hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride).

In some embodiments, the kits can contain one or more (e.g., one, two, or three or more) of any of the XBP1, CD138, and/or CS1 antibodies described herein. In some embodiments, the kits can include two antibodies, each specific for a different protein. For example, a kit can contain one XBP1-specific antibody (described herein) and one CS1-specific antibody (described herein). In some embodiments, the kits can include three antibodies, each specific for a different protein. The kits can optionally include instructions for assaying a biological sample for the presence or amount of one or more of XBP1, CD138, and/or CS1 proteins.

Also featured are articles of manufacture that include: a container; and a composition contained within the container, wherein the composition comprises an active ingredient for inducing an immune response in a mammal (e.g., a human), wherein the active ingredient comprises one or more (e.g., two, three, four, five, six, seven, eight, nine, or 10 or more) of any of the peptides described herein, and wherein the container has a label indicating that the composition is for use in inducing an immune response in a mammal (e.g., any of the mammals described herein). The label can further indicate that the composition is to be administered to a mammal having, suspected of having, or at risk of developing, multiple myeloma and/or Waldenstrom's macroglobulinemia. The composition of the article of manufacture can be dried or lyophilized and can include, e.g., one or more solutions (and/or instructions) for solubilizing a dried or lyophilized composition.

The articles of manufacture can also include instructions for administering the composition to the mammal (e.g., as described above).

The following examples are intended to illustrate, not limit, the invention.

EXAMPLES

Example 1

Materials and Methods

Cell Lines.

The human multiple myeloma cell lines: McCAR, MM1 S and U226, were obtained from the American Type Culture Collection (ATCC; Manassas, Va.). The human acute myeloid leukemia (AML) cell line, ML-2, was kindly provided by Dr. Y. Matsuo, Fujisaki Cell Center, Okayama, Japan. The T2 cell line, which is a human B and T cell hybrid expressing HLA-A2.1 molecules (Zweerink et al., (1993) J.

Immunol. 150(5):1763-71), was provided by Dr. J. Molldrem (University of Texas M. D. Anderson Cancer Center, Houston, Tex.) and was used as a source of antigen presenting cells (APCs). All cell lines were cultured in RPMI-1640 medium (Gibco-Life Technologies, Rockville, Md.) supplemented with 10% fetal calf serum (FCS; BioWhittaker, Walkersville, Md.), 100 IU/ml penicillin and 100 µg/ml streptomycin (Gibco-Life Technologies).

Reagents.

Mouse anti-human CD80 or CD83 monoclonal antibodies (mAb) conjugated with phycoerythrin (PE) were purchased from Immunotech (Hialeigha, Fla.). CD3, CD4, CD8, CD14, CD40, CD45RA, CD45RO, CD69, CD80, CD83, CD86, CCR7, HLA-A2 and HLA-DR-specific mAbs conjugated with fluoroscein isothyocyanate (FITC), PE or PerCP were purchased from Becton Dickinson/Pharmingen (San Diego, Calif.).

Synthetic Peptides.

Influenza virus protein matrix peptide$_{58-66}$ (GILGFVFTL; SEQ ID NO:25) and MAGE-3 peptide (FLWGPRALV; SEQ ID NO:26) were used as control HLA-A2-binding peptides. Six native non-spliced XBP1 peptides: XBP1$_{117-125}$ (LLREKTHGL; SEQ ID NO:1); XBP1$_{184-192}$ (NISPWILAV (SEQ ID NO:2)); XBP1$_{189-197}$ (ILAVLTLQI (SEQ ID NO:3)); XBP1$_{192-200}$ (ILAVLTLQI (SEQ ID NO:4)); XBP1$_{110-118}$ (KLLLENQLL (SEQ ID NO:5)); XBP1$_{93-101}$ (RMSELEQQV (SEQ ID NO:27)); three native spliced XBP1 peptides including SP XBP1$_{196-204}$ (GILDNLDPV (SEQ ID NO:7)); SP XBP1$_{193-201}$ (ILLGILDNL (SEQ ID NO:8)); SP XBP1$_{367-375}$ (ELFPQLISV (SEQ ID NO:9)); heteroclitic XBP1 (YISPWILAV (SEQ ID NO:6)); and heteroclitic spliced XBP1 (YILDNLDPV (SEQ ID NO: 27)); and YLFPQLISV (SEQ ID NO:10)) peptides were designed and examined as potential HLA-A2-binding peptides. As used herein, "heteroclitic" (e.g., a heteroclitic peptide) refers to a form of a peptide in which one or more amino acids have been modified from a wild-type or original sequence in order to produce a peptide that is more immunogenic than the corresponding wild-type peptide. For example, in the exemplary heteroclitic peptides described immediately above, the bolded amino acids indicate the amino acids that are modified from the wild-type sequence of XBP1.

Four native CD138 peptides: CD138$_{256-264}$ (VIAGGLVGL (SEQ ID NO:11)); CD138$_{260-268}$ (GLVGLIFAV (SEQ ID NO:12)); CD138$_{5-13}$ (ALWLWLCAL (SEQ ID NO:13)); and CD138$_{7-15}$ (WLWLCALAL (SEQ ID NO:14)) were designed and examined as potential HLA-A2-binding peptides.

Four native CS1 peptides: CS1-P1: CS1$_{236-245}$ (LLLSLFYLGL (SEQ ID NO:15)); CS1-P2: CS1$_{239-247}$ (SLFVLGLFL (SEQ ID NO:16)); CS1-P3: CS1$_{232-240}$ (LLVPLLLSL (SEQ ID NO:17)); and CS1-P4: CS1$_{9-17}$ (TLIYILWQL (SEQ ID NO:18)) were designed (using three different databases RANKPEP, BIMAS and NetMHC) and examined as potential HLA-A2-binding peptides. (See, e.g., Reche et al. (2002) Human Immunology 63:710-709).

XBP-1 and CD138 peptides were synthesized (Biosynthesis, Lewisville, Tex.) by standard FMOC (9-fluorenylmethyl-oxycarbonyl) chemistry, purified to >85% using reverse-phase chromatography and validated by mass-spectrometry for molecular weight. CS1 peptides were synthesized by New England Peptides LLC with greater than 95% purity. Lyophilized peptides were dissolved in dimethyl sulfoxide (DMSO) (Sigma, St. Louis, Mo.), diluted in AIM-V medium (Gibco-Life Technologies) and stored at −140° C.

Peptide Binding Assay.

The XBP1, CD138, or CS1 peptides were evaluated for HLA-A2 binding on T2 cells. In the assay, T2 cells were washed, resuspended in serum-free AIM-V medium to a final concentration of 1×10$^6$ cells/ml, and transferred into a 24-well tissue culture plate. The cells were incubated with 50 µg/ml of respective XBP1, CD138, or CS1 peptides or 30 µg/ml influenza virus protein matrix peptide plus 3 µg human β2 microglobulin (Sigma) and incubated at 37° C., 5% CO$_2$ in humidified air. Following an overnight incubation, the cells were washed, and then contacted with a FITC-conjugated (or in the case of determining the binding of CS1 peptides to HLA-A2, a PE-conjugated) mouse anti-human HLA-A2 monoclonal antibody for 15 minutes at 4° C. The cells were again washed and then analyzed by fluorescence flow cytometry (FFC) using a FACSort™ flow cytometer with CellQuest™ v2.1 software (Becton Dickinson, San Jose, Calif.). The capability of a peptide to bind to HLA-A2 was determined by measuring the up-regulation of HLA-A2 molecules on the surface of T2 cells caused by the binding of the peptides to HLA-A2 and reflected in mean fluorescence intensity (MFI) with FFC analyses.

Peptide Stability Assay.

The stability of XBP1 or CD138 peptides in the binding groove of the HLA-A2 molecule was examined using the human T2 cell line. T2 cells were incubated with the various peptides as described above. After an overnight incubation, the cells were washed to remove unbound peptide and then incubated with 10 µg/ml Brefeldin A (Sigma) at 37° C. for 1 hour to block cell surface expression of newly synthesized HLA-A2.1 molecules. The peptide/HLA-A2 binding stability was measured at 0, 2, 4, 6 and 18 hours post-Brefeldin A treatment. Following the incubation period, the cells were harvested, washed, stained with an FITC-conjugated mouse anti-human HLA-A2 monoclonal antibody and analyzed by FFC using a FACSort™ flow cytometer with CellQuest™ v2.1 software (Becton Dickinson).

Generation of Monocyte-Derived Mature Dendritic Cells.

Peripheral blood mononuclear cells (PBMC) were isolated from leukopaks obtained from normal human donors using standard density gradient centrifugation over Ficoll-Paque™ Plus (Amersham Pharmacia Biotech AB, Uppsala Sweden). Dendritic cells (DC) were generated from monocytes obtained as the adherent cell fraction as follows. To generate immature DC (immDC), the monocytes were cultured for 7 days in the presence of 1,000 U/ml GM-CSF (granulocyte-macrophage-colony stimulating factor) and 1,000 U/ml IL-4 (interleukin-4) in RPMI-1640 medium (Gibco-Life Technologies, Rockville, Md.) supplemented with 10% fetal calf serum (FCS; BioWhittaker, Walkersville, Md.). Fresh medium plus GM-CSF and IL-4 was added to the cultures every other day. Mature DC (mDC) were obtained by culturing the immDCs in 1,000 U/ml IFN-α (interferon alpha) plus 10 ng/ml TNF-α (tumor necrosis factor alpha) along with fresh GM-CSF and IL-4 in 10% FCS-RPMI on day 7 for three days. The immDC and mDC were harvested and examined for their expression phenotypes using CD14-, CD40-, CD80-, CD83-, CD86-, and HLA-DR-specific antibodies and FFC analyses.

Isolation of CD3$^+$ T Cells.

T cells of normal donors were obtained from the non-adherent cell fraction (post-monocytes adherence) of PBMC using the Pan T cell isolation kit from Miltenyi Biotec (Auburn, Calif.). In brief, T cell enrichment was accomplished by depletion of B cells, NK cells, early erythroid cells, platelets and basophils by labeling with a cocktail of hapten-conjugated CD11b, CD16, CD19, CD36 and CD56 antibodies and a column containing MACs microbeads coupled to an anti-hapten monoclonal antibody. The effluent (negative cell fraction) was collected from the column as enriched CD3+ T cells. Purity (mean±standard deviation) of the CD3+ T cells enriched from the initially obtained T cells was examined by flow cytometry and was found to be 94±2%.

Induction of Peptide-Specific CTL.

Peptide-specific CTL (that is, XBP1, CD138, or CS1-peptide-specific CTL) were generated ex vivo by repeated stimulation of CD3+ T lymphocytes obtained from normal HLA-A2+ donors with XBP1, CD138, or CS1-peptide-pulsed antigen-presenting cells (APC), either T2 cells or mDC. In brief, T2 cells were washed and resuspended in serum-free AIM-V medium (Gibco BRL) and pulsed overnight at 37° C. with 50 µg/ml of the appropriate XBP1 or CD138 peptide. Peptide-pulsed APC were washed, counted, irradiated at 10 Gy and used to prime CD3+ T cells at a 1:40 T2/peptide (stimulator)-to-CD3+ T cell (responder) ratio in AIM-V medium supplemented with 10% human AB serum (Bio-Whittaker, Walkersville, Md.). The T cell cultures were restimulated every seven days with irradiated APC/peptide for a total of 4 cycles to generate XBP1 peptide-specific CTL (XBP1-CTL), CD138 peptide-specific CTL (CD138-CTL), or CS1 peptide-specific CTL (CS1-CTL). It is clear from the foregoing that "XBP1-CTL," "CD138-CTL," and "CS1-CTL" referred to herein are not clonal (or homogenous) populations. Rather, the XBP1-CTL, CD138-CTL, and CS1-CTL cells are heterogenous populations of lymphocytes comprising XBP1 peptide-, CD138 peptide-, or CS1 peptide-specific CTL along with non-specific CTL, APCs, and other lymphocytes obtained from the normal donors. 50 U/ml of interleukin-2 (IL-2) was added to the cultures two days after the second stimulation. Control T cell cultures (unstimulated with peptide) were maintained in AIM-V medium supplemented with 10% human AB serum containing 50 U/ml IL-2.

Phenotypic Analysis of the XBP1-CTL, CD138-CTL, or Target Cells.

To determine the phenotype of the XBP1-CTL, CD4, or CD8 expression by the cells was detected using anti-CD4-PE or anti-CD8-FITC mouse anti-human mAbs. In addition, a variety of other expression markers were detected on the cells using combinations of either FITC-conjugated anti-CD69/PE-conjugated-anti-CD45RO or FITC-conjugated anti-CD45RA-FITC/PE-conjugated anti-CCR7 mouse anti-human mAbs. Alternatively, HLA-A2 expression by U266, McCAR, ML-2 and MM1S cells was determined using an FITC-conjugated anti-HLA-A2 anti-human mAb. After contacting the cells with antibodies for 15 minutes at 4° C., the cells were washed and analyzed using a FACSort™ flow cytometer with CellQuest v2.1 software (Becton Dickinson).

Western Blotting.

Approximately 100 µg protein lysate from each cell line (U266, McCAR, ML-2, and MM1S) was suspended in Laemmli's sample buffer (0.1 M Tris-HCl buffer, pH 6.8, containing 1% sodium dodecyl sulfate (SDS), 0.05% β-mercaptoethanol, 10% glycerol and 0.001% bromophenol blue), boiled for two minutes and subjected to 8-16% gradient sodium dodecyl sulfate-polyacrylamide gel electrophoresis (SDS-PAGE) for two hours (Xcell Surelock Mini Cell, Invitrogen, Carlsbad, Calif.) at 80 V. A protein ladder (a mixture of proteins of known molecular weight) was used as a size marker in the gel to determine the molecular weight of the peptides (Invitrogen, Carlsbad, Calif.). Gels were electroblotted onto nitrocellulose membranes (Trans-Blot, 0.2 micron transfer membrane, Bio-Rad Laboratories, CA) at 40 V for two hours in a Tris-glycine buffer. Transfer of the proteins onto the nitrocellulose membrane was confirmed by Ponceau S staining. Incubation of the membrane with mouse anti-human XBP1 antibody or an anti-human CD138 antibody was performed for one hour in phosphate buffered saline and Tween 20 (PBST) containing 1% BSA with constant rocking. The membrane was washed three times with PBST and incubated in anti-mouse IgG-horseradish peroxidase conjugates for one hour in PBST containing 3% non-fat dry milk. After washing, specific proteins were detected using enhanced chemiluminescence, according to the instructions provided in the product manual (Amersham Life Sciences Inc., Arlington Heights, Ill.).

IFN-γ ELISA.

IFN-γ release by XBP1-CTL, CD138-CTL, or CS1-CTL following co-culture with multiple myeloma (MM) cells (McCAR, MM1S), acute myelogenous leukemia (AML) cells (ML-2), or T2 cells (above) was measured using a human IFN-γ ELISA kit from BD Biosciences (San Diego, Calif.). Briefly, dilutions of purified IFN-γ as standards or CTL supernates were transferred into wells of a 96-well plate pre-coated with a monoclonal anti-human IFN-γ capture antibody and incubated for 2 hours at room temperature. After several washes, a buffer containing a detection antibody and avidin-horseradish peroxidase conjugate was added to each well and incubated for one hour at room temperature. The wells were washed and then to each well was added a horseradish peroxidase substrate solution and incubated at room temperature for 30 minutes. Stop solution was added to each well and the absorbance was determined at 450 nm was determined with a PerkinElmer Wallac Victor2 counter (PerkinElmer, Wellesley, Mass.). The amount of cytokine present in the CTL culture supernatant was calculated based on the IFN-γ standard curve.

Cell Proliferation by Carboxy Fluorescein Succinimidyl Ester (CFSE) Tracking.

XBP1-CTL or CD138-CTL were washed twice in PBS (Gibco-BRL) and resuspended in RPMI-1640 culture medium at a concentration of $1 \times 10^6$ cells/ml. CFSE (Molecular Probes, Eugene, Oreg.) in the form of a 5 mM stock solution in DMSO was added to the CTL to give a final concentration of 5 µM and incubated for 10 minutes at 37° C. in a $CO_2$ incubator protected from light. After incubation, a volume of ice-cold PBS (containing 2% FCS) equivalent to five-times the volume of the CTL cells was added to the cells to quench the reaction. Cells were incubated for 5 minutes on ice, centrifuged and resuspended in fresh PBS (containing 2% FCS) after a total of three washings. CFSE-labeled T cells were adjusted to a concentration of $2 \times 10^6$ cells/ml with RPMI culture medium, stimulated with $2 \times 10^5$ cells/ml McCAR cells, ML-2 cells, MM1S cells, or no cells. The stimulated CFSE-labeled cells were examined on by FFC analysis day 4.

Cytotoxicity Assay.

The cytotoxic activities of the XBP1-CTL, CD138-CTL, or CS1-CTL were measured by a calcein release assay as described by, e.g., Roden et al. (1999) J. Immunol. Methods 226:29-41. Briefly, target cells ($3 \times 10^5$ cells) including T2, U266 cells, McCAR cells, ML-2 cells, and MM1S cells were incubated in serum-free culture medium containing 10 mM calcein-AM (Molecular Probes) for 30 minutes at 37° C., washed three times in cold PBS with 5% FCS, and incubated with effector cells ($5 \times 10^3$ cells/well) at various effector:target cell ratios in 96-well U-bottom microtiter plates (triplicate wells/sample). Plates were incubated for 3 hours at 37° C. and 5% $CO_2$. After incubation, the cells were pelleted by centrifugation at 1,000 rpm for 5 minutes and 100 µl of the supernatant was transferred to the wells of 96-well flat-bottomed microtiter plates (Nunc) and the calcein-release was measured as the amount of fluorescence released from the cells (using a VICTOR²-1420 multilabel counter (PerkinElmer, Boston, Mass.)). Maximum calcein release was obtained from detergent-released target cell counts and spontaneous release from target cell counts in the absence of effector cells. Cellular cytotoxicity was calculated as follows: % Specific Lysis=[(experimental release−spontaneous release)÷(maximum release−spontaneous release)]×100.

CD107 Cytotoxicity Assay.

The CD107 cytotoxicity assay was performed as described by Betts et al. (2003) and Mittendorf et al. (2005) with minor modifications as detailed below. T2 or McCAR cells grown in serum-free media and in wells of a tissue culture plate were contacted with CD138 peptide or MAGE peptide at 37° C. for approximately 12 hours. The cells were then washed to remove unbound peptides. CD138-CTL were then co-cultured with the above treated T2 cells or McCAR cells (each of which presenting peptide antigen) at various effector:target ratios. A 10 µl aliquot of each of CD107a and CD107b (both conjugated to the detectable label FITC) was added to each well at the same time of adding the CD138-CTL. The plate containing the cells was centrifuged for 5 minutes at 1000 rpm and incubated at 37° C. for one hour. Following the incubation, 0.02 µg of Brefeldin A was added to each well and the cells were incubated at 37° C. for an additional four hours. The cells were collected and washed with Pharmingen Stain Buffer (Pharmingen-BD Biosciences, San Jose, Calif.) and contacted with a PE-conjugated mouse anti-human CD8 antibody for 30 minutes to detect CD8 expression. The cells were washed and analyzed by flow cytometry.

Example 2

XBP1$_{184\text{-}192}$ (NISPWILAV) and Spliced XBP1$_{367\text{-}145}$ (ELFPQLISV) Peptides Display High Affinity/Stability to HLA-A2 Binding The full length sequences of non-spliced or spliced XBP1 protein (see above) were analyzed using the search software SYFPEITHI (A database of MHC ligands and Peptide Motifs, Institute for Cell Biology, Department of Immunology, Heidlberg) to predict peptides specific to HLA-A2 followed by the BIMAS program to select peptides with extended half-time disassociation rates. A total of six potential HLA-A2-binding native peptides were selected from non-spliced XBP1 protein as follows: XBP1$_{117\text{-}125}$ (LLREKTHGL (SEQ ID NO:1); XBP1 #1 peptide), XBP1$_{184\text{-}192}$ (NISPWILAV (SEQ ID NO:2); XBP1 #2 peptide), XBP1$_{189\text{-}197}$ (ILAVLTLQI (SEQ ID NO:3); XBP1 #3 peptide), XBP1$_{192\text{-}200}$ (ILAVLTLQI (SEQ ID NO:4); XBP1 #4 peptide), XBP1$_{110\text{-}118}$ (KLLLENQLL (SEQ ID NO:5); XBP1 #5 peptide), and XBP1$_{93\text{-}101}$ (RMSELEQQV (SEQ ID NO:27); XBP1 #6 peptide). In addition, three potential HLA-A2-binding native peptides were selected from spliced XBP1 protein for evaluation: SP XBP1$_{196\text{-}204}$ (GILDNLDPV (SEQ ID NO:7); SP XBP1 #1 peptide), SP XBP1$_{193\text{-}201}$ (ILLGILDNL (SEQ ID NO:8); SP XBP1 #2 peptide) and SP XBP1$_{367\text{-}375}$ (ELFPQLISV (SEQ ID NO:9); SP XBP1 #3 peptide). The HLA-A2 affinity of these native XBP1 peptides and influenza virus protein matrix peptide$_{58\text{-}66}$ (GILGFVFTL (SEQ ID NO:24)), which is known to be HLA-A2-binding peptide, was assessed using the T2 peptide-binding assay. The specific affinity of the peptides was evaluated as HLA-A2-mean fluorescence intensity (MFI), which is a function of HLA-A2 up-regulation on T2 cells following peptide binding to HLA-A2. Among the tested peptides derived from non-spliced XBP1 protein, XBP1$_{184\text{-}192}$ (NISPWILAV (SEQ ID NO:2); referred to as XBP1 #2 p) was determined to have the highest affinity for HLA-A2 (MFI=720±140) and possessed an even higher affinity than influenza virus protein matrix peptide$_{58\text{-}66}$ (GILGFVFTL (SEQ ID NO:16)) (MFI=604±10). The remaining peptides, XBP1$_{117\text{-}125}$ (LLREKTHGL (SEQ ID NO:1)), XBP1$_{189\text{-}197}$ (ILAVLTLQI (SEQ ID NO:3)), XBP1$_{192\text{-}200}$ (ILAVLTLQI (SEQ ID NO:4)), XBP1$_{110\text{-}118}$ (KLLLENQLL (SEQ ID NO:5)) and XBP1$_{93\text{-}101}$ (RMSELEQQV (SEQ ID NO:27)) also had significant affinity for HLA-A2 affinity, although less than that of XBP1$_{184\text{-}192}$ (NISPWILAV (SEQ ID NO:2)) peptide (FIG. 1).

Figure 2:
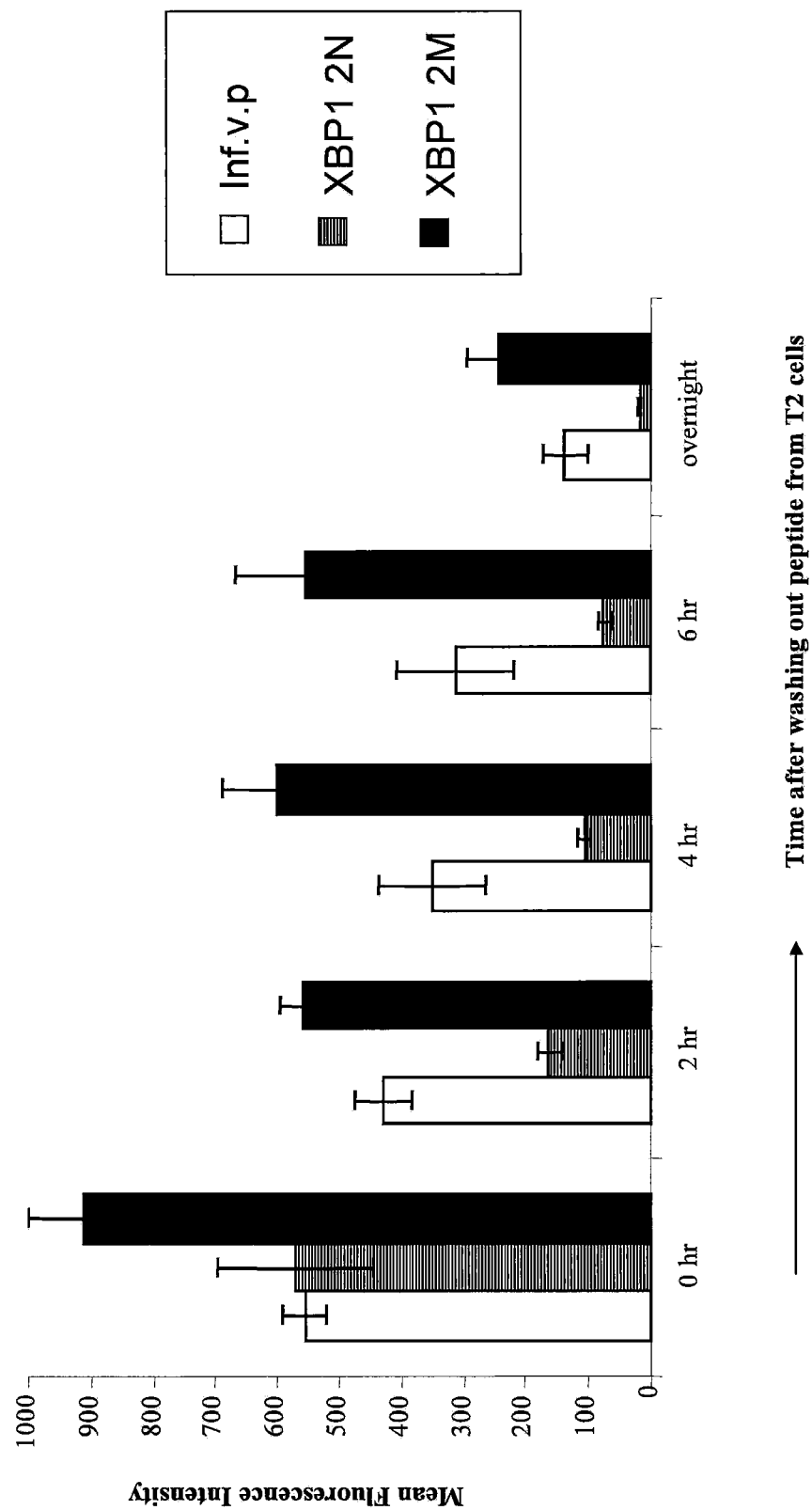
FIG. 2 is a bar graph depicting the stability of fluorophore-labeled XBP 1 peptides ($XBP1_{184\text{-}192}$ (NISPWILAV (XBP1 2N; SEQ ID NO:2)) and YISPWILAV (XBP1 2M; SEQ ID NO:6)) within the cleft of HLA-A2 molecules on the surface of human T2 cells. The influenza virus protein matrix peptide$_{58\text{-}66}$ (GILGFVFTL (SEQ ID NO:24)) was also evaluated as a control. The Y-axis represents the mean fluorescence intensity and the X-axis represents the time intervals at which the stability of the peptides was measured.

The HLA-A2 binding stability of each of the peptides was evaluated at 0, 2, 4, 6 and 18 hours post-Brefeldin A treatment. Preliminary studies demonstrated that the non-spliced XBP1 #2p peptide had a significantly lower level of HLA-A2 binding stability as compared to the influenza virus protein matrix peptide$_{58\text{-}66}$ (GILGFVFTL (SEQ ID NO:24)). In order to improve the stability of the XBP1 #2p within the HLA-A2 cleft, a heteroclitic peptide was designed from the native XBP1$_{184\text{-}102}$ (NISPWILAV (SEQ ID NO:2)), wherein arginine 184 was replaced with tyrosine (heteroclitic YISPWILAV (SEQ ID NO:6) peptide; herein referred to as XBP1 2M; the bolded amino acid indicates the amino acid that was modified from the wild-type sequence). FIG. 2 depicts the results of an experiment to test the HLA-A2 binding stability of XBP1 2M. As shown in FIG. 2, a significantly longer period of HLA-A2 up-regulation on T2 cells (as a function of the binding stability of the peptide) was observed for the heteroclitic peptide as compared to the native peptide counterpart. These results demonstrated that modification of the peptide resulted in a higher HLA-A2 binding stability.

Figure 3:
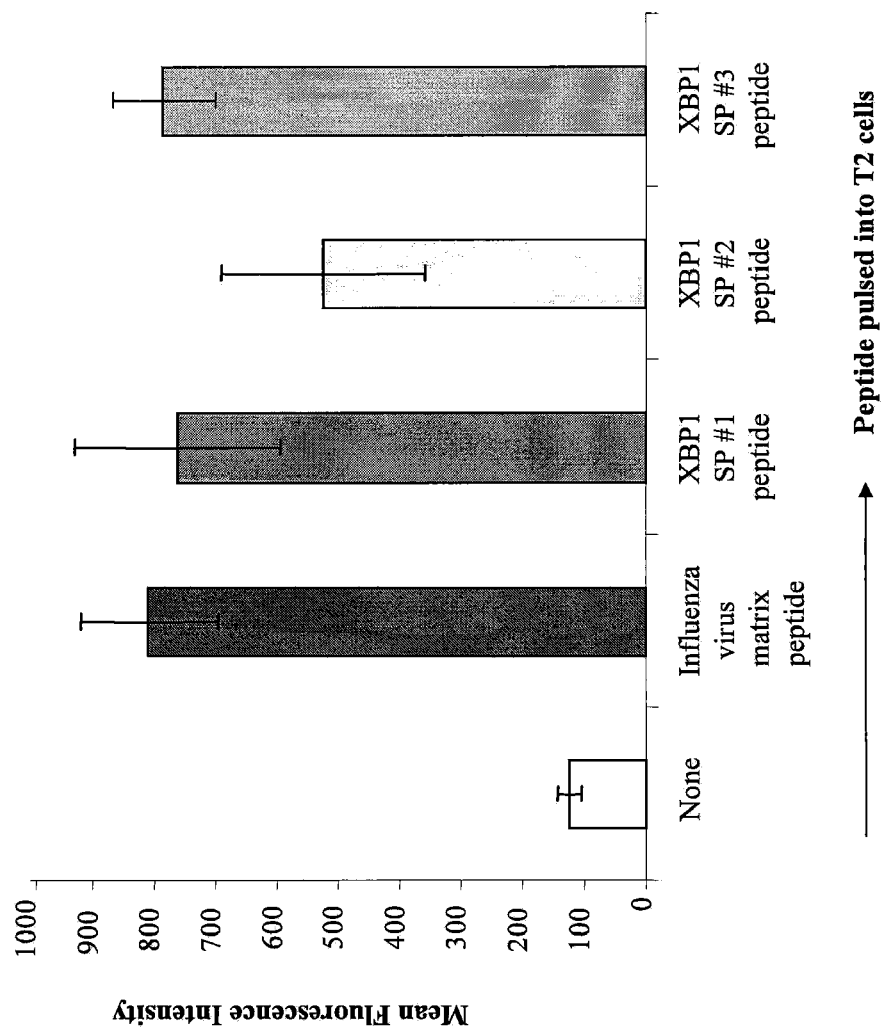
FIG. 3 is a bar graph depicting the affinity of fluorophore-labeled XBP1 peptides for HLA-A2 molecules on the surface of human T2 cells. The Y-axis represents the mean fluorescence intensity and the X-axis depicts the various peptides screened in the assay: native $XBP1_{196\text{-}204}$ (GILDNLDPV (SEQ ID NO:7); XBP1 SP #1p) and $XBP1_{367\text{-}375}$ (ELFPQLISV (SEQ ID NO:9); XBP1 SP #3p). The influenza virus protein matrix peptide$_{58\text{-}66}$ (GILGFVFTL (SEQ ID NO:24); "Inf. v.p.")) was also evaluated as a control.
Figure 4:
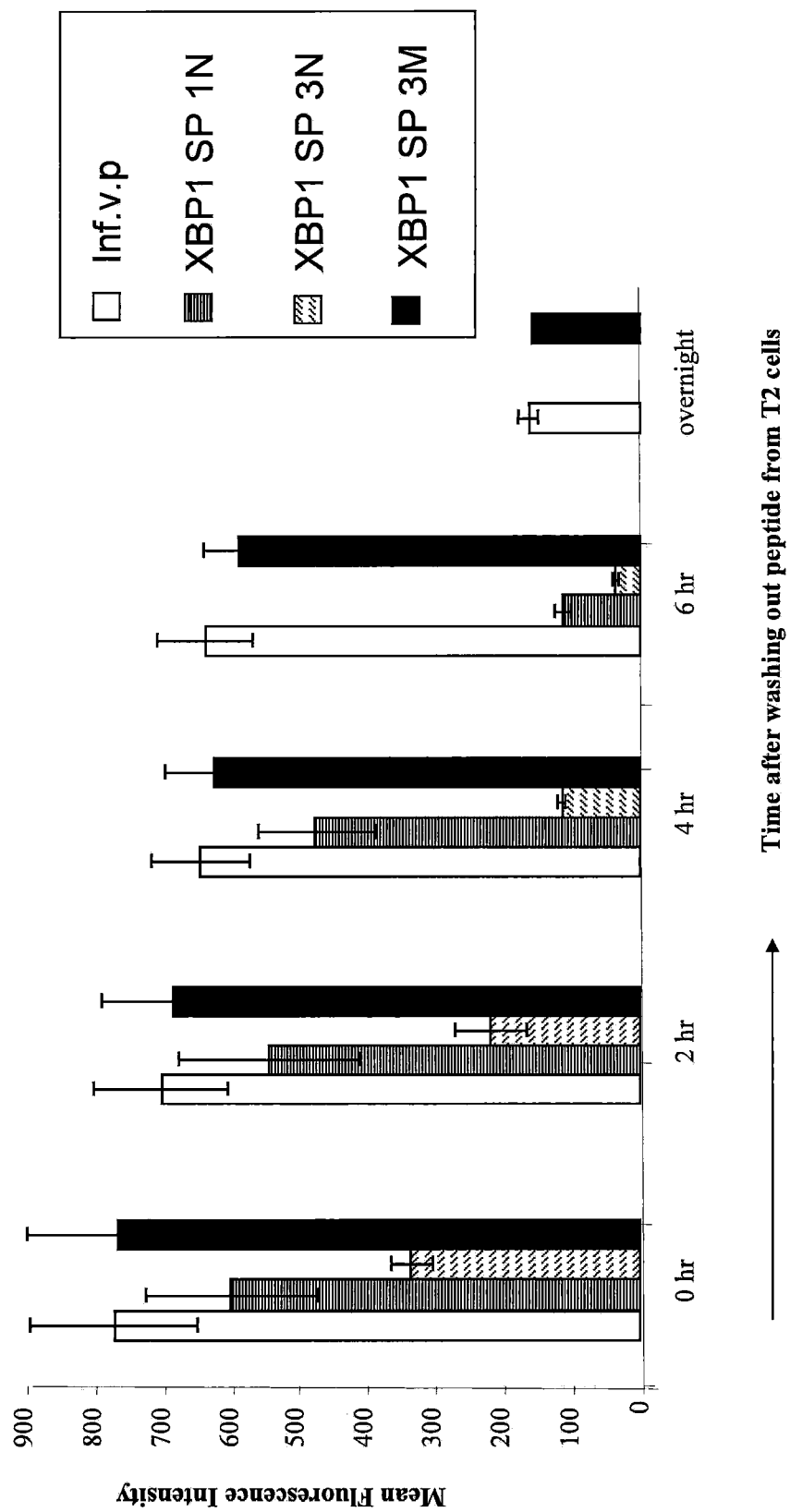
FIG. 4 is a bar graph depicting the stability of fluorophore-labeled XBP1 peptides (XBP1 SP 1N (GILDNLDPV; SEQ ID NO:7); XPB1 SP 3N (ELFPQLISV; SEQ ID NO:9) and XBP1 SP 3M (YLFPQLISV SEQ ID NO: 10)) within the cleft of HLA-A2 molecules on the surface of human T2 cells. The Y-axis represents the mean fluorescence intensity and the X-axis represents the time intervals after which the stability of the peptides was measured.

Among the spliced XBP1 peptides tested, native SP XBP1$_{196\text{-}204}$ (GILDNLDPV (SEQ ID NO:7); SP XBP1 #1p) and SP XBP1$_{367\text{-}375}$ (ELFPQLISV (SEQ ID NO:9); SP XBP1 #3p) each possessed high affinity for HLA-A2 as reflected in MFI scores of 762±167 and 785±84, respectively. This affinity was comparable to that of influenza virus protein matrix peptide$_{58\text{-}66}$ (GILGFVFTL (SEQ ID NO:24)) having an MFI=807±113 (FIG. 3). The peptide sequences SP XBP1 #1p and SP XBP1 #3p were modified as above to enhance their HLA-A2 binding stability. That is, the first amino acid of each peptide was replaced with tyrosine. FIG. 4 depicts the increase in HLA-A2 up-regulation on T2 cells induced by the heteroclitic peptide YLFPQLISV (SEQ ID NO: 10; referred to as SP XBP1 #3M) as compared to its native counterpart. This higher level of HLA-A2 up-regulation was maintained by culturing the heteroclitic peptide for 6 hours in Brefeldin A, after removing excess, unbound peptides from the cell-containing wells. In contrast to the efficacy of XBP1 #3M, the heteroclitic peptide YILDNLDPV (SEQ ID NO:28), which was derived from the native peptide XBP1 #1p, did not exhibit a significant increase in HLA-A2 stability over its native counterpart.

Thus, the heteroclitic peptides YLFPQLISV (SEQ ID NO:10) and YISPWILAV (SEQ ID NO:6) were selected for further evaluation of their ability to activate XBP1-antigen-specific cytotoxic T lymphocytes (XBP1-CTL).

Example 3

The XBP1-CTL Display a Distinct Phenotype from Unstimulated T Cells

Cytotoxic T lymphocytes (CTL) are defined phenotypically by the expression of distinct cell surface antigens (e.g., CD8). Cell surface antigens can also be used to further define CTL as naïve or activated memory cells. For example, naïve human CTL can be identified by the presence of CD45RA$^+$/

Figure 5:
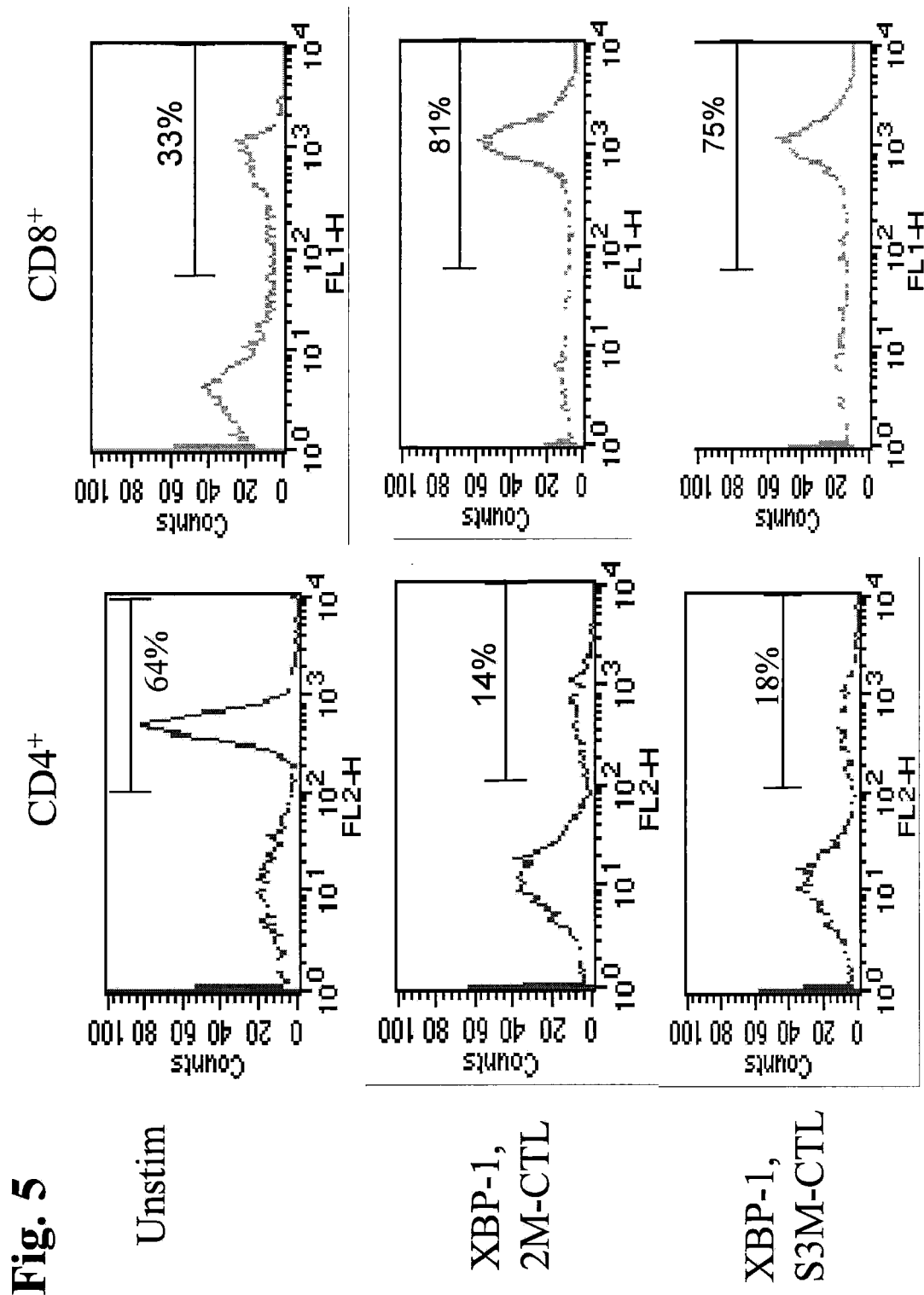
FIG. 5 is a series of one-dimensional fluorescence flow cytometry (FFC) histograms depicting the percentage of $CD4^+$ and $CD8^+$ T lymphocytes in a mixed population of human lymphocytes. Cytotoxic T lymphocytes (CTL) populations were either unstimulated (unstim), or stimulated with one of XBP1 2M (XBP1 2M-CTL) or XBP-1 S3M (above). The influenza virus protein matrix peptide$_{58\text{-}66}$ (GILGFVFTL (SEQ ID NO:24); "Inf. v.p.") was also evaluated as a control. The Y-axis of each histogram indicates the number of cells and the X-axis represents the fluorescence intensity of fluorescently-labeled specific antibodies bound to CD4 antigens (left column) or CD8 antigens (right column) on the cells. The indicated percentages of the cells within the gates are indicated.

CCR7+, whereas activated human memory cells can be identified as CD69+/CD45RO+. Flow cytometry was performed on populations of human T cells stimulated with the heteroclitic peptides to determine the percentage of CTL that were naïve or activated memory cells. FIG. 5 shows that CTL stimulated with XBP1 heteroclitic peptides induce a significantly higher percentage of CD8+ T cells (non-spliced peptide stimulation: 81%; spliced peptide stimulation: 75%) as compared to unstimulated T cell cultures (33%), and a lower percentage of CD4+ T cells (non-spliced peptide stimulation: 14%; spliced peptide stimulation: 18%) as compared to unstimulated T cell cultures (64%). The unstimulated control T cells or CD138-CTL were further examined for naïve (CD45RA+/CCR7+) or activated memory (CD69+/CD45RO+) cell status. Where control T cell cultures contained 24% of CD45RA+CCR7+ naïve cells, only 1% or 2% of the XBP1-CTL exhibited this phenotype. In addition, the cell population expressing CD69+/CD45RO+ (activated memory) phenotype was significantly higher in the XBP1-CTL (non-spliced peptide stimulation: 62%; spliced peptide stimulation: 64%) compared to the control T cells (4%) (FIG. 6). These results demonstrate that XBP1 heteroclitic peptides change the phenotype of T cells to activated CTL.

Example 4

McCAR and U266 Express HLA-A2 and XBP1 Antigens

The expression of HLA-A2 and XBP1 antigens in several multiple myeloma cell lines was determined using flow cytometry and western blotting. Each of U266, McCAR, ML-2, and MM1S cells were contacted with a detectably labeled anti-HLA-A2 antibody and subjected to flow cytometry analysis. High HLA-A2 surface expression was detected on U266, McCAR and ML-2 cell lines but not on the MM1S cell line. Intracellular expression of XBP1 in each of the various cell lines was determined by Western blot. Cell lysates were prepared from each of the cell lines and subjected to SDS-PAGE. These analyses showed that spliced XBP1 protein was expressed in U266, McCAR and MM1S, but not ML-2 cell line. In contrast, unspliced XBP1 was observed in all cell lines tested.

Example 5

Antigen-Specific and HLA-A2-Restricted IFN-γ Secretion by the XBP1-CTL

Figure 7:
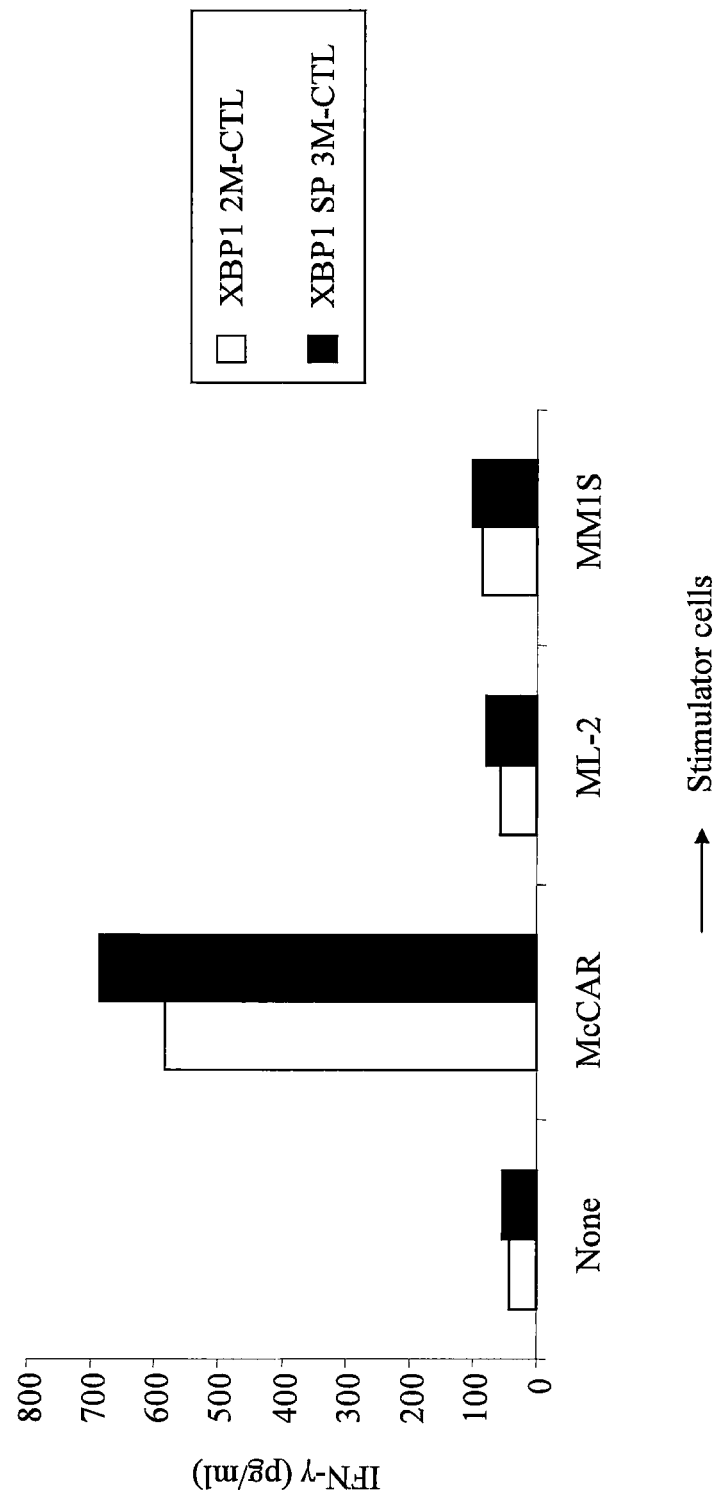
FIG. 7 is a bar graph depicting the release of IFN-γ (interferon-γ) XBP1-CTL (XBP1 2M-CTL and XBP1 SP 3M-CTL) co-cultured with multiple myeloma (MM) McCAR cells and MM1 S cells and the acute myelogenous leukemia (AML) ML-2 cells. The Y-axis represents the amount of IFN-γ released from the CTL-containing cells in units of pg/mL.

Antigen-specificity and HLA-A2.1-restriction of the above-generated XBP1-CTL was determined by measuring the induction of IFN-γ secretion following stimulation with the above-referenced multiple-myeloma cell lines. The XBP1-CTL exhibited a significant increase (*p<0.05) in IFN-γ secretion when cultured with McCAR cells. In contrast, very little IFN-γ secretion from the XBP1-CTL was observed when cultured with ML-2 or MM1S cells (FIG. 7). Only McCAR cells were found to express both HLA-A2 and XBP1. These results suggest that XBP1-CTL are capable of an antigen-specific and HLA-A2-restricted response to XBP1 peptides presented on multiple myeloma cells.

Example 6

Antigen-Specific and HLA-A2-Restricted Cell Proliferation by the XBP1-CTL

XBP1-CTL were exposed to carboxyfluoroscein succinimidyl ester (CFSE) as described above. Proliferation of the XBP1-CTL in response to stimulation with various tumor lines was determined by measuring the amount of CFSE in the cells. CFSE is a membrane permeable dye, which is taken up by cells. Upon cell division, one half of the CFSE is distributed to each daughter cell. In turn, when each of the daughter cells divide, a total of one quarter of the original CFSE concentration is distributed to the third generation cells. Thus, the number of cell divisions can be determined as the inverse of the concentration of dye in each cell of a population.

Figure 8:
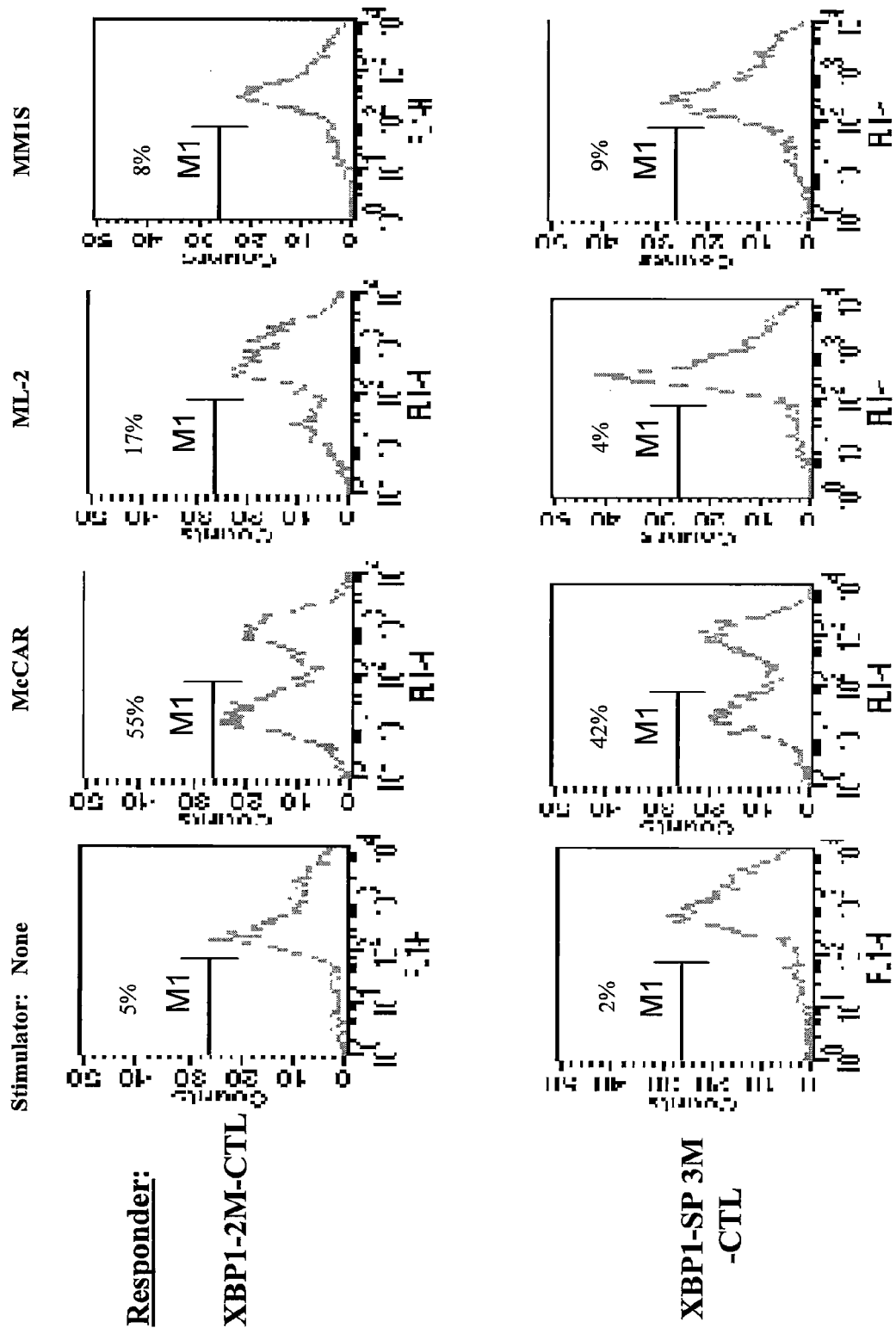
FIG. 8 is a series of two-dimensional FFC histograms depicting the proliferation of XBP1-CTL (XBP1 2M-CTL and XBP1-SP 3M CTL) following co-culture with MM or AML cells. The Y-axis represents the number of each cell in the population and the x-axis represents the amount of carboxyfluoroscein succinimidyl ester (CFSE) in the cells.

XBP1-CTL were incubated with the membrane permeable dye CFSE for 10 minutes, washed, and then contacted with the above-mentioned multiple myeloma cells. The amount of CFSE was determined using flow cytometry. No significant CTL proliferation was observed when the cells were incubated with 50 U/ml IL-2. However, significantly higher CTL proliferation was observed when the XBP1-CTL cells were cultured with McCAR cells (M1 gated; XBP1-2M: 55%, XBP1 SP-3M: 42%) (FIG. 8). These results demonstrate that proliferation of CTL cells was XBP1-specific and HLA-A2-restricted and are consistent with the IFN-γ secretion data.

Example 7

Antigen-Specific and HLA-A2-Restricted Cytotoxic Activity of XBP1-CTL

Figure 9:
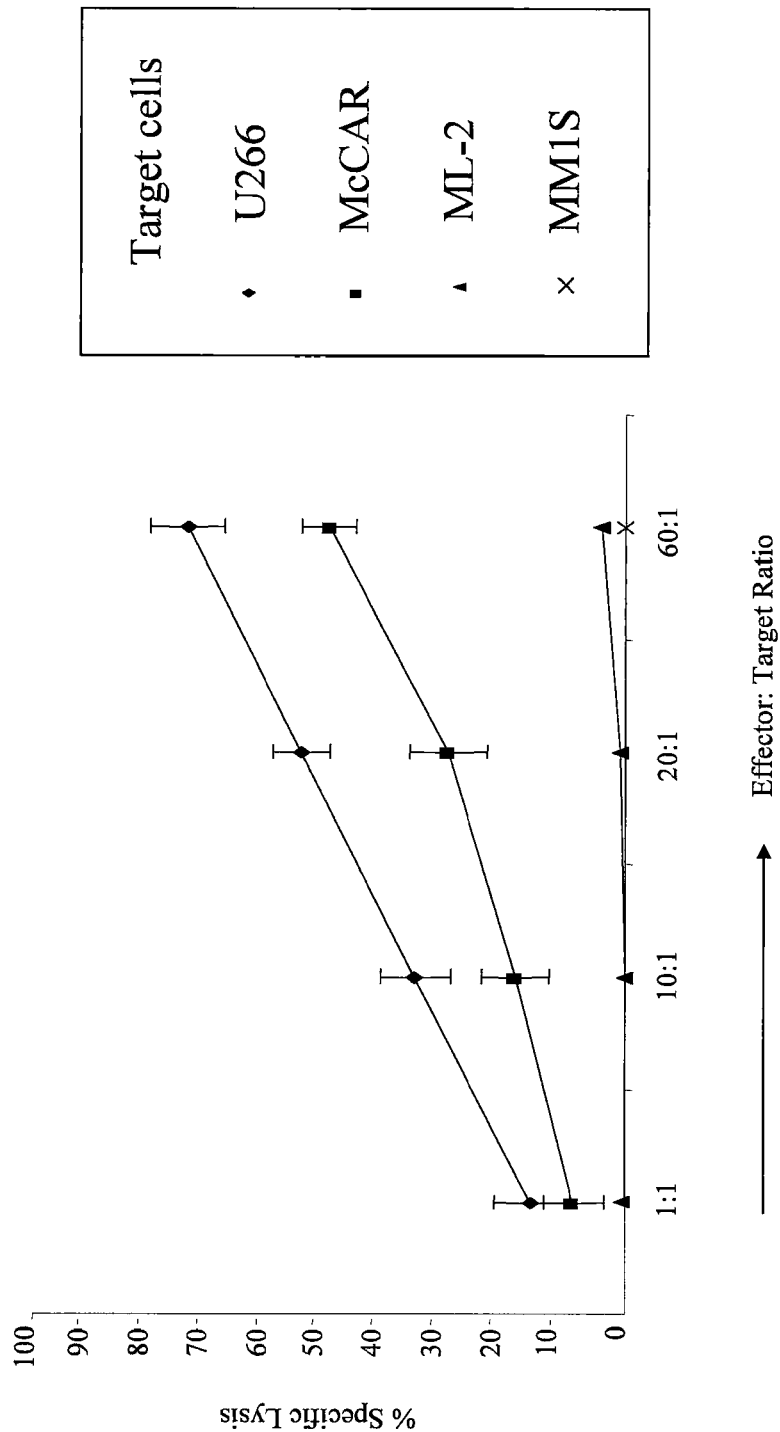
FIGS. 9 and 10 are a pair of line graphs depicting the XBP1-CTL-dependent lysis of cancer cells as determined by calcein-release assay. XBP1-2M-specific CTL (FIG. 9) or XBP1-SP-3M-CTL (FIG. 10) were co-cultured with each of U266 cancer cells, McCaAR cancer cells, ML-2 cancer cells, or MM1S cancer cells and the amount of cancer cell lysis by the CTL was calculated as a function of the amount of calcein released from the cancer cells. The Y-axis represents the percent specific lysis of target cells and the X-axis represents the ratio of CTL to cancer cells (effector to target cell ratio) (1:1, 10:1, 20:1, or 60:1).
Figure 10:
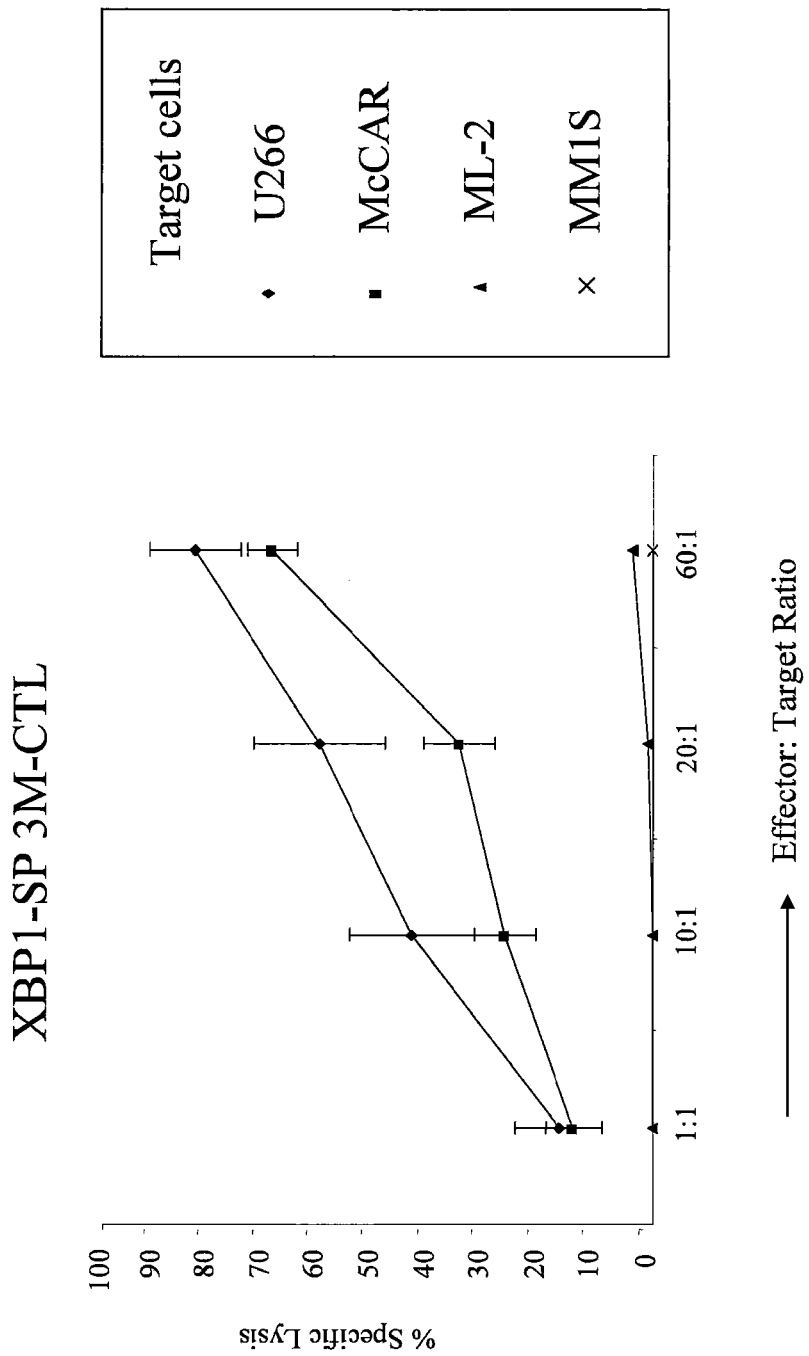

The ability of the heteroclitic XBP1 peptide-specific CTL to specifically target and lyse multiple myeloma cells was determined. The XBP1-CTL induced with either YISPWILAV (SEQ ID NO: 6; XBP1 SP 2M) or YLFPQLISV (SEQ ID NO:10; XBP1 SP 3M) peptide were examined for their ability to lyse multiple myeloma cells as determined by calcein release cytotoxicity assays. Each of the CTL populations were co-cultured with the MM or AML cells and the amount of lysis was determined by measuring the amount of calcein released from the lysed cells. As shown in FIGS. 9 and 10, the XBP1 2M-specific CTL (FIG. 9) as well as XBP1 SP 3M-specific CTL (FIG. 10) were capable of lysing HLA-A2+/XBP1+ malignant MM cells, McCAR (9-50% lysis by XBP1 2M-CTL and 15-69% lysis by XBP1 SP 3M-CTL) and U266 (16-74% lysis by XBP1 2M-CTL and 18-83% lysis by XBP1 SP 3M-CTL). However, the CTL did not significantly induce lysis of the HLA-A2+ AML cells (ML-2) or HLA-A2−MM cells (MM1S), demonstrating this cellular cytotoxicity is antigen-specific and HLA-A2-restricted. In addition, the CTL did not kill the natural killer (NK)-sensitive cell line K562, confirming that the observed cytotoxicity against the multiple myeloma cells was not due to contaminating NK cells in the XBP1-CTL.

Example 8

Affinity of CD138 Peptides for HLA-A2 Binding

The full length sequences of CD138 (see above) were analyzed using the search software SYFPEITHI (A database of MHC ligands and Peptide Motifs, Institute for Cell Biology, Department of Immunology, Heidlberg) to predict peptides specific for HLA-A2, followed by the BIMAS program to select peptides with extended half-time disassociation rates. A total of four potential HLA-A2-binding native peptides were selected: $CD138_{256-264}$ (VIAGGLVGL; CD138 #1p (SEQ ID NO:11)); $CD138_{260-268}$ (GLVGLIFAV; CD138 #2p (SEQ ID NO:12)); $CD138_{5-13}$ (ALWLWLCAL; CD138 #3p (SEQ ID NO:13)); and $CD138_{7-15}$ (WLWLCALAL; CD138 #4p (SEQ ID NO:14)). The HLA-A2 binding affinity of these native CD138 peptides and influenza virus protein matrix peptide$_{58-66}$ (GILGFVFTL (SEQ ID NO:24)) was assessed using the T2 peptide-binding assay. The affinity of the peptides was evaluated as HLA-A2-mean fluorescence intensity (MFI), HLA-A2 being up-regulated on T2 cells through the HLA-A2-specific binding.

Figure 11:
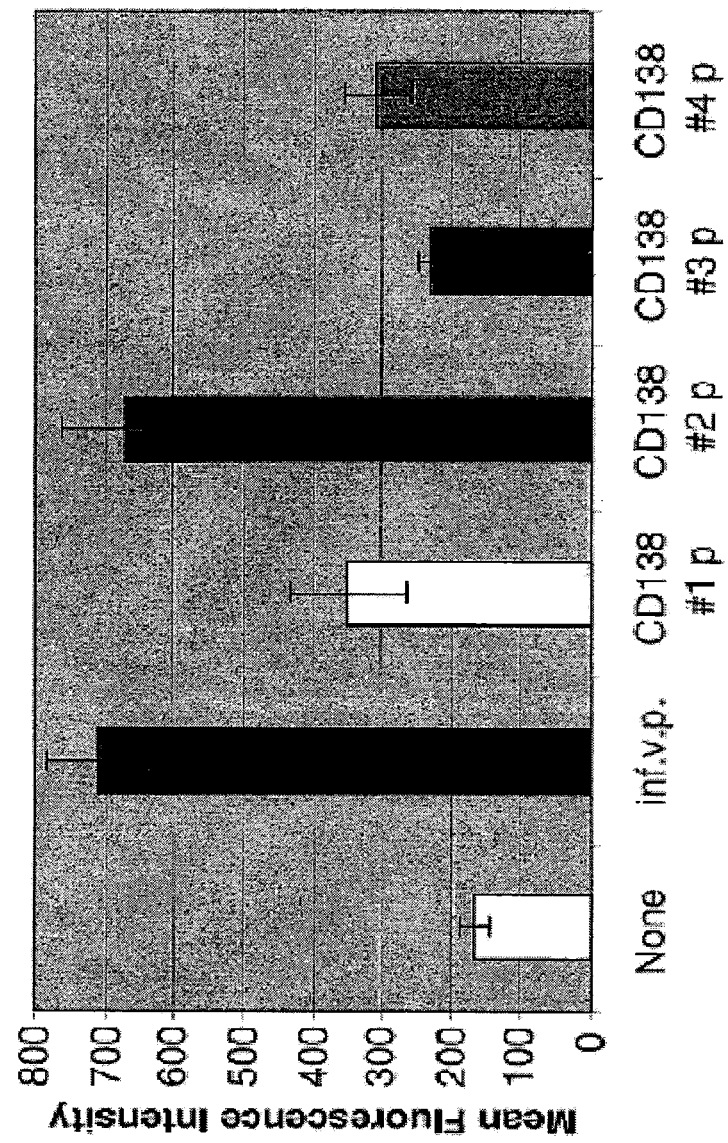
FIG. 11 is a bar graph depicting the affinity of fluorophore-labeled CD138 peptides for HLA-A2 molecules on the surface of human T2 cells. The Y-axis represents the mean fluorescence intensity and the X-axis indicates the various peptides screened in the assay: CD138$_{256-264}$ (VIAGGLVGL; CD138 #1p (SEQ ID NO:11)); CD138$_{260-268}$ (GLVGLIFAV; CD138 #2p (SEQ ID NO:12)); CD138$_{5-13}$ (ALWLWLCAL; CD138 #3p (SEQ ID NO:13)); and CD138$_{7-15}$ (WLWLCALAL; CD138 #3p (SEQ ID NO:14)). The influenza virus protein matrix peptide$_{58-66}$ (GILGFVFTL (SEQ ID NO:24); "Inf. v.p.") was also evaluated as a control.

Among the tested peptides derived from CD138, CD138 #2p was determined to have the most specific HLA-A2 binding (MFI=690±65), which was close to the affinity of the HLA-A2-specific control influenza virus protein matrix peptide58-66 (MFI=705±80). The remaining peptides, CD138 #1p, CD138 #3p, and CD138 #4p exhibited significantly lower HLA-A2 binding affinity than the CD138 #2p peptide (FIG. 11).

Figure 12:
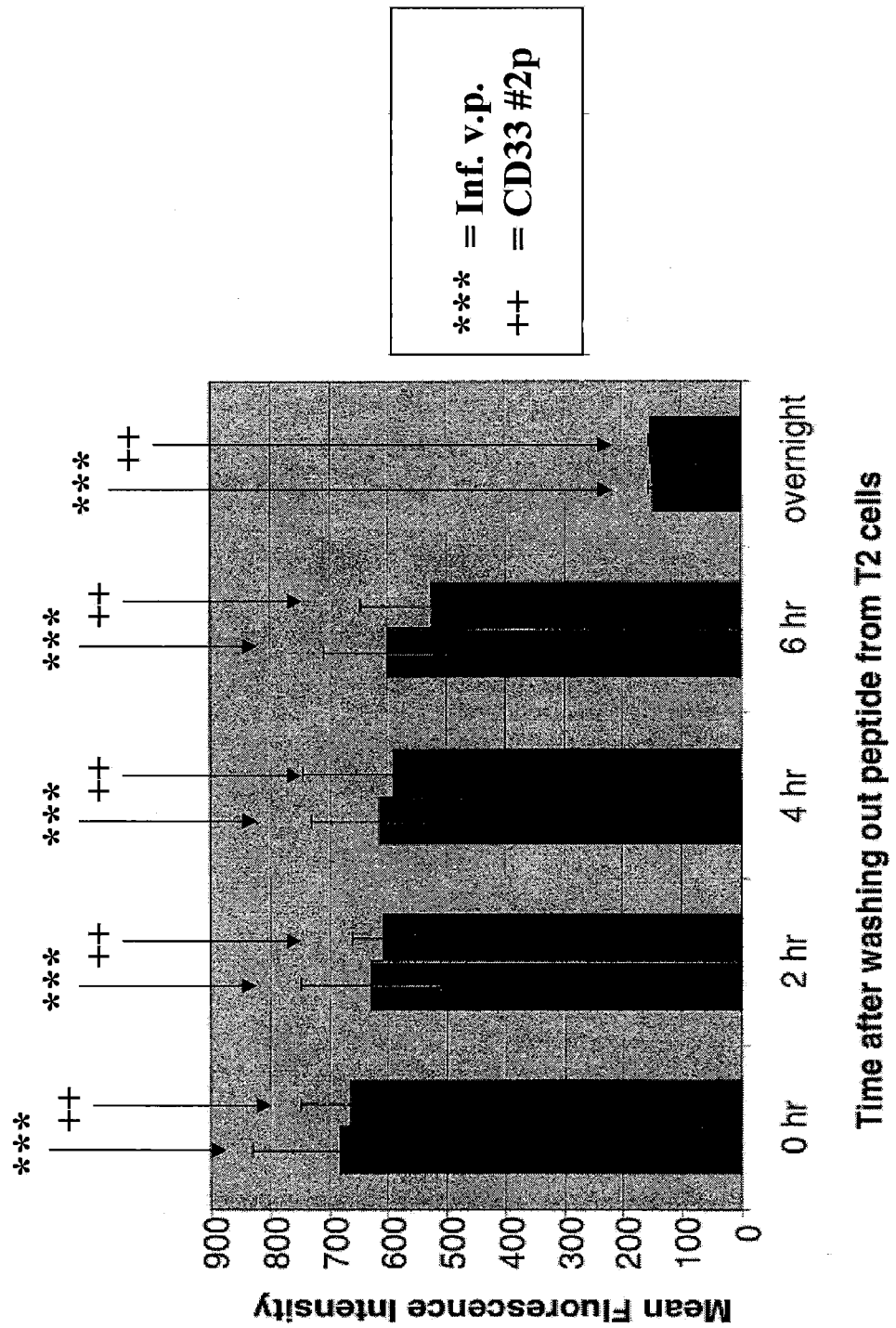
FIG. 12 is a bar graph depicting the stability of fluorophore-labeled CD138 #2 peptide within the cleft of HLA-A2 molecules on the surface of human T2 cells (as compared to influenza virus protein matrix peptide$_{58-66}$ (GILGFVFTL (SEQ ID NO:24); "Inf. v.p.")). The Y-axis represents the mean fluorescence intensity and the X-axis represents the time intervals in which the stability of the peptides was measured.

The HLA-A2 binding stability of CD138 #2p was also evaluated at 0, 2, 4, 6 and 18 hours post-Brefeldin A treatment. FIG. 12 depicts the results of an experiment to test the HLA-A2 binding stability of CD138 #2p. As shown in FIG. 12, the CD138 #2p was nearly equivalent to influenza virus protein matrix peptide$_{58-66}$ (GILGFVFTL (SEQ ID NO:24)) in its ability to induce HLA-A2 up-regulation on T2 over time (0 hr, 2 hr, 4 hr, 6 hr, or overnight after peptide pulsing). This demonstrated the high level of stability of the CD138 #2p binding to HLA-A2 molecules.

Thus, the CD138 #2p was selected for further evaluation of its ability to activate CD138-antigen-specific cytotoxic T lymphocytes (CD138-CTL).

Example 9

The CD138-CTL Display a Distinct Phenotype from Unstimulated T Cells

Figure 13:
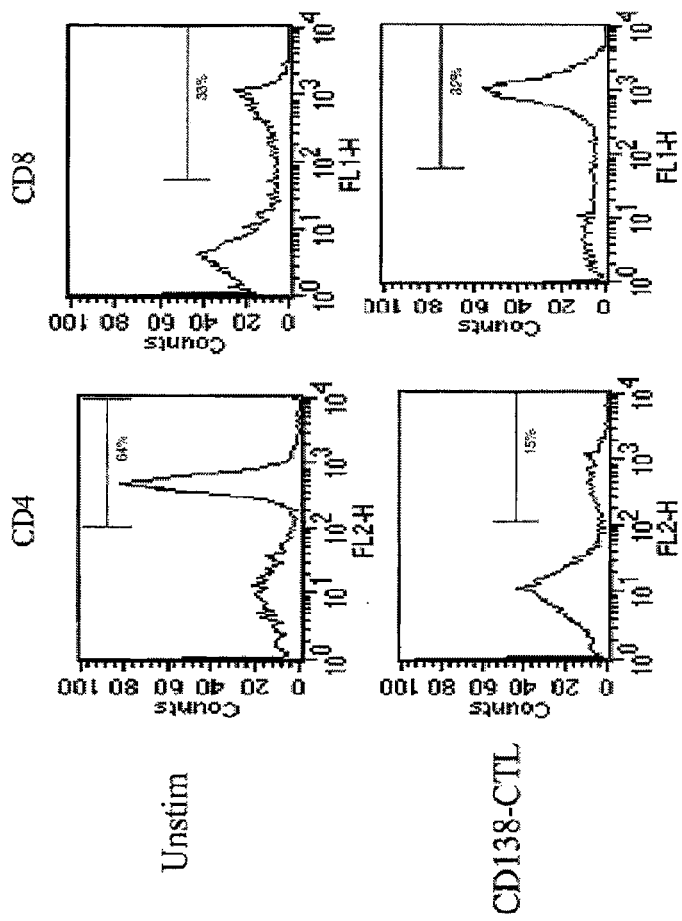
FIG. 13 is a series of one-dimensional FFC histograms depicting the percentage of CD4$^+$ and CD8$^+$ T lymphocytes in a population. CTL populations were either unstimulated (unstim), or stimulated with CD138 #2 peptide (CD138-CTL). The Y-axis of each histogram represents the number of cells and the X-axis represents the fluorescence intensity of fluorescently-labeled specific antibodies bound to CD4 antigen (left column) or CD8 antigens (right column) on the cells.
Figure 14:
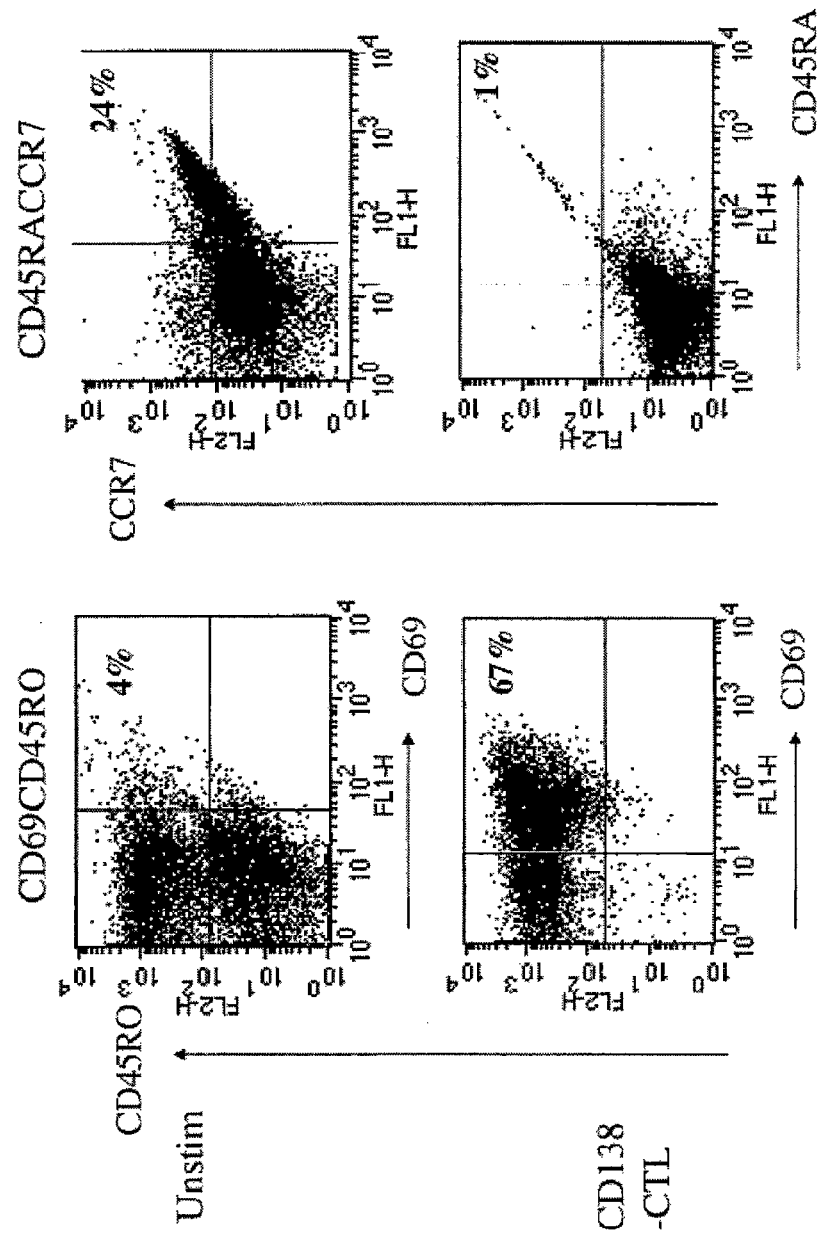
FIG. 14 is a series of two-dimensional FFC histograms depicting the percentage of cells in a population of lymphocytes that are CD69$^+$/CD45RO$^+$ or CD45RA$^+$/CCR7$^+$ following stimulation with CD138 #2 peptide. CTL populations were either unstimulated (unstim), or stimulated with CD138 #2 peptide (CD138-CTL). The X-axis (FL-1) of each dot plot represents the fluorescence intensity of fluorescently-labeled specific antibodies bound to CD69 antigen (left column) or CD45RA antigens (right column) on the cells and the Y-axis (FL-2) of each dot plot depicts the fluorescence intensity of fluorescently-labeled specific antibodies bound to CD45RO antigen (left column) or CCR7 antigens (right column) on the cells. The indicated percentages of the cells in the upper right hand quadrants of the dot plots are indicated.
Figure 15:
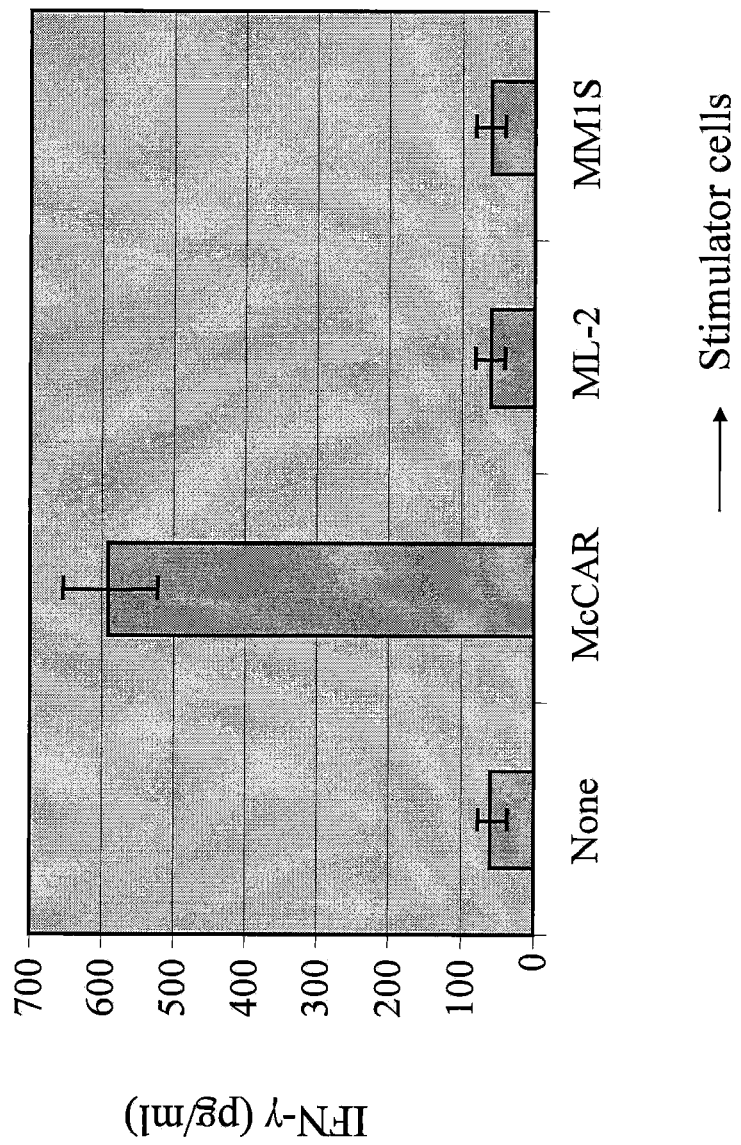
FIG. 15 is a bar graph depicting the release of IFN-γ from CD138-CTL co-cultured with multiple myeloma (MM) McCAR cells (CD138$^+$/HLA-A2$^+$), MM1S cells (CD138$^+$/HLA-A2$^-$), or the acute myelogenous leukemia (AML) ML-2 cells (CD138$^-$/HLA-A2$^-$). The Y-axis represents the amount of IFN-γ released from the CTL in units of pg/mL and the X-axis indicates the cancer cells used as stimulator cells. Antigen-specificity and HLA-A2-restriction of the CD138-CTL was determined by measuring the induction of IFN-γ secretion following overnight stimulation with the tumor cell lines.

FFC was performed on populations of T cells stimulated with the heteroclitic peptides to determine the percentage of CTL that were naïve or activated memory cells. FIG. 13 shows that CTL stimulated with CD138 #2p peptide demonstrated a significantly higher percentage of CD8$^+$ T cells (peptide stimulation: 82%) as compared to unstimulated T cell cultures (33%), and a lower percentage of CD4$^+$ T cells (peptide stimulation: 15%) as compared to unstimulated T cell cultures (64%). The unstimulated control T cells or CD138-CTL were further examined for naïve (CD45RA$^+$/CCR7$^+$) or activated memory (CD69$^+$/CD45RO$^+$) cell status. Where control T cell cultures contained 24% of CD45RA$^+$ CCR7$^+$ naïve cells, only 1% of the CD138-CTL exhibited this phenotype. In addition, the proportion of cells expressing the CD69$^+$/CD45RO$^+$ (activated memory) phenotype was significantly higher in the CD138-CTL (67%) as compared to the control T cells (4%) (FIG. 14). These results demonstrate that CD138 #2p peptide changed the phenotype of the T cells to that of the activated CTL.

Example 10

McCAR and U266 Express HLA-A2 and CD138 Antigens

The expression of HLA-A2 and CD138 antigens in several multiple myeloma cell lines was determined using FFC. High HLA-A2 surface expression was detected on U266, McCAR and ML-2 cell lines but not on the MM1S cell line. Intracellular expression of CD138 was observed in U266, McCAR and MM1S cell lines, but not the ML-2 cell line.

Example 11

Antigen-Specific and HLA-A2-Restricted IFN-γ secretion by the CD138-CTL

Further confirmation of the antigen-specificity and HLA-A2-restriction of the CD138-CTLs was provided by the induction of IFN-γ secretion following overnight stimulation with the various tumor cell lines. The CD138-CTL showed a significant increase (*p<0.05) in IFN-γ secretion following stimulation with McCAR cells (CD138$^+$/HLA-A2$^+$), as compared to stimulation with multiple myeloma MM1S cells (CD138$^+$/HLA-A2$^-$), or the acute myelogenous leukemia ML-2 cells (CD138$^-$/HLA-A2$^-$). These results provide further evidence of an antigen-specific and HLA-A2-restricted response by the CD138-CTL.

Example 12

Antigen-Specific and HLA-A2-Restricted Cell Proliferation by the CD138-CTL

Figure 16:
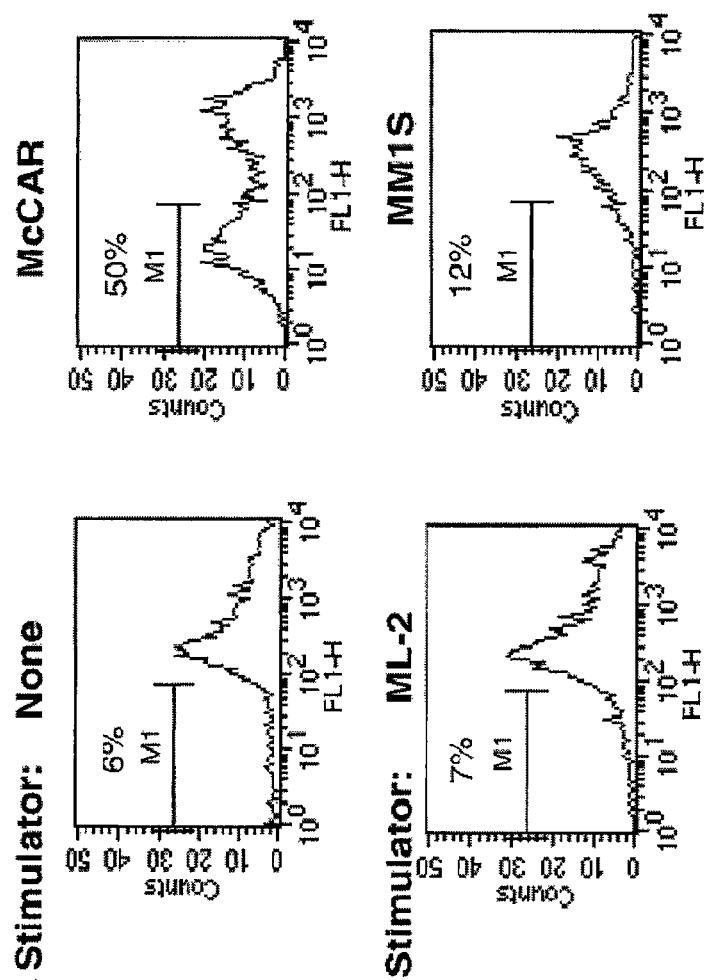
FIG. 16 is a series of one-dimensional FFC histograms depicting the proliferation of CD138-CTL (CD138 #2p-CTL) following co-culture with McCAR, ML-2, or MM1S cancer cells. The Y-axis represents the number of each cell in the population and the x-axis represents the amount of carboxyfluoroscein succinimidyl ester (CFSE) in the cells. The indicated percentages of the cells in the upper right hand quadrants of the dot plots are indicated.

Proliferation of CD138-CTL in response to stimulation with various tumor lines was determined by measuring the amount of CFSE in the cells. CD138-CTL were incubated with the membrane permeable dye CFSE for 10 minutes, washed, and then contacted with the above-mentioned multiple myeloma cells. The amount of CFSE was determined using FFC. No significant cell proliferation was observed when the cells were incubated with 50 U/ml IL-2. However, significantly higher CTL proliferation was observed when the CD138-CTL cells were cultured with McCAR cells (M1 gated; 50%) (FIG. 16). These results demonstrate that proliferation of CTL cells was CD138-specific and HLA-A2-restricted and are consistent with the IFN-γ secretion data.

Example 13

CD138-CTL in a Calcien-Cytotoxicity Assay

Figure 17:
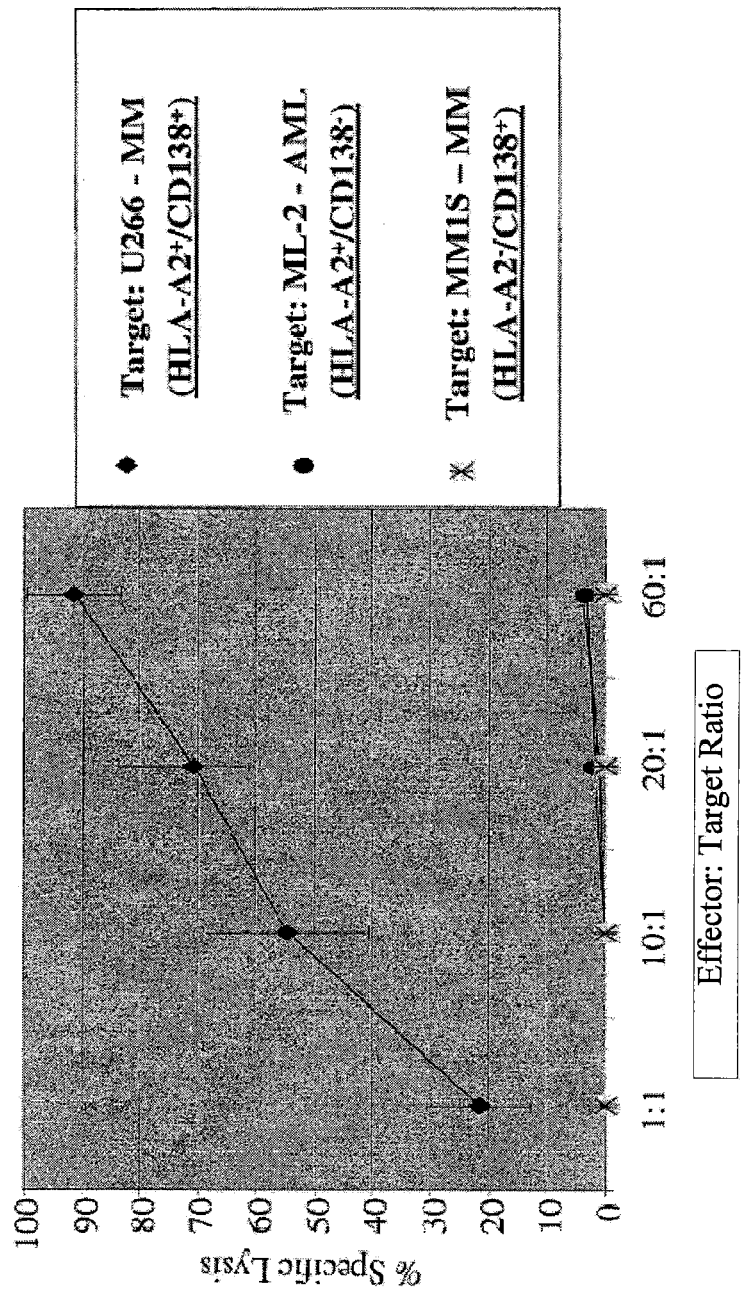
FIG. 17 is a line graph depicting the CD138-CTL-dependent lysis of cancer cells as determined by calcein-release assay. CD138 #2p-specific CTL (were co-cultured with each of cancer cells U266, ML-2, or MM1S cells and the amount of cancer cell lysis by the CTL was calculated as a function amount of calcein released from the cancer cells. The Y-axis represents the percent specific lysis of target cells and the X-axis represents the ratio of CTL to cancer cells (effector: target ratio) (1:1, 10:1, 20:1, or 60:1).

The ability of the CD138-CTL to specifically target and lyse multiple myeloma cells was determined. The CD138-CTL induced with either CD138 #2p peptide were examined for their ability to lyse multiple myeloma cells as determined by calcein release cytotoxicity assays. As shown in FIG. 17, the CD138-CTL were able to lyse of HLA-A2$^+$/CD138-1$^+$ malignant multiple myeloma cells, U266. However, the CTL did not significantly lyse the HLA-A2$^+$ AML cells (ML-2) or HLA-A2$^-$ MM cells (MM1S), demonstrating that this cellular cytotoxicity is antigen-specific and HLA-A2-restricted. In addition, the CTL did not kill the natural killer (NK)-sensitive cell line K562, confirming that the cytotoxicity observed against the multiple myeloma cells was not due to contaminating NK cells in the CD138-CTL.

Example 14

CD138-CTL in a CD107 Cytotoxicity Assay

Figure 18A:
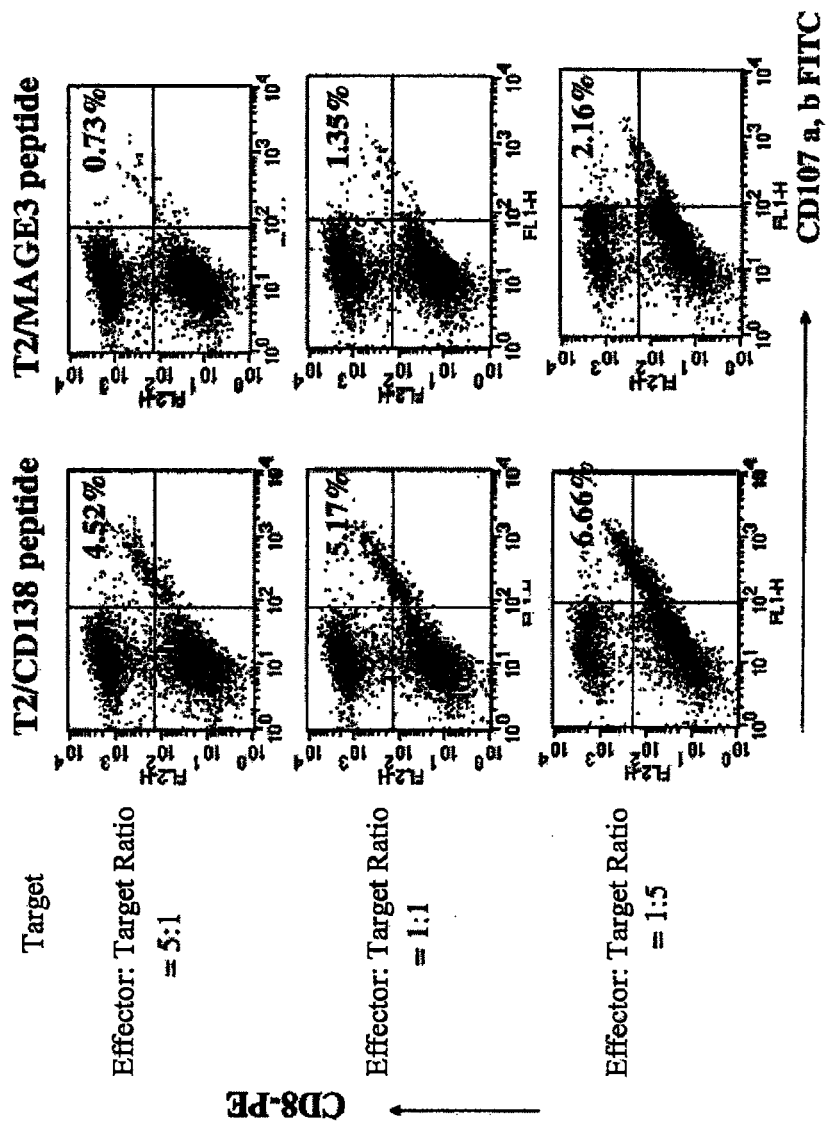

The CD107 assay allows for phenotypic and functional characterization of responding CD8$^+$ T cells using a marker that is only expressed during degranulation, the initial event that takes place during target cell lysis. Using this assay, the cytoxicity level of CD138-CTL was measured by analyzing the level of up-regulation of CD107a and CD107b on the cell surfaces of CD138-CTL by flow cytometry analyses. The results demonstrated that CD138-CTL undergo physiologic changes to induce the lysis of corresponding CD138-peptide presenting T2 cells, but not to irrelevant MAGE3 peptide pulsed T2 cells at different effector to target ratios (5:1, 1:1, or 1:5) (FIG. 18A). In addition, the CD138-CTL-induced lysis of corresponding CD138 peptide-presenting McCAR cells (CD138+/HLA-A2+) cells, but not to irrelevant MAGE3 peptide-presenting cells (at the ratio of CTL:stimulator (1:1)) (FIG. 18 B).

Example 15

Expression of CS1 Polypeptide by Multiple Myeloma cell lines and Primary Multiple Myeloma Cancer Cells The expression of HLA-A2 and CS1 antigens in several multiple myeloma cell lines was determined using FFC microarray analysis. Each of U266, McCAR, ML-2, and MM1S cells were contacted with a detectably-labeled anti-HLA-A2 antibody and a detectably-labeled anti-CS1 antibody and subjected to flow cytometry analysis. Similarly, primary MM cells from each of six patients with MM were obtained and contacted with a detectably labeled anti-HLA-A2 antibody and a detectably-labeled anti-CS1 antibody and subjected to flow cytometry analysis. Elevated levels of HLA-A2 and CS1 protein surface expression were detected on the surface of U266, McCAR, and ML-2 cell lines, but not on the MM1S cell line.

Figure 19:
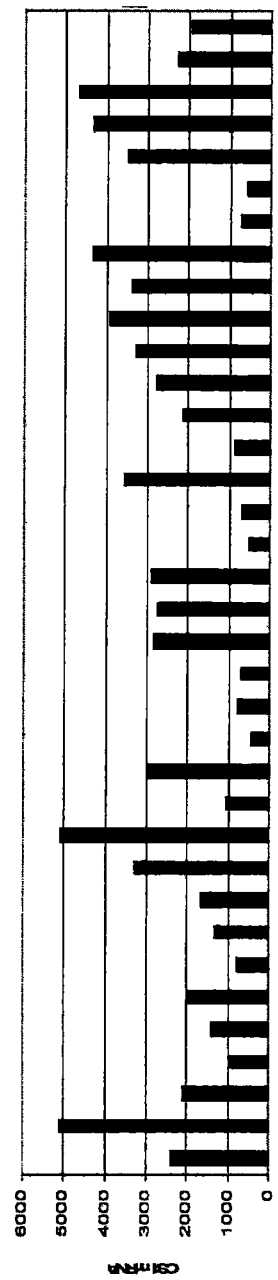
FIG. 19 is a bar graph depicting the relative expression (Y-axis) of CS1 mRNA by each of a number of multiple myeloma cancer cell samples. Each of the samples were obtained from a different human patient with multiple myeloma.

In order to test whether CS1 is expressed in primary MM cells obtained from human patients, a microarray analysis was performed on primary MM samples obtained from multiple patients. Total RNA was isolated from CD138-purified tumor cells of each MM patient and subjected to microarray analysis using an Affymetrix U133 Plus 2.0 array (Affymetrix, California). An elevated CS1 mRNA expression in the MM cells, as compared to the expression in cells from patients without MM, was observed in the majority of the MM cells (FIG. 19).

In total, these results demonstrate that CS1 protein is expressed in both primary and cultured MM cells.

Example 16

Affinity of CS1 Peptides for HLA-A2 Binding

The full length sequences of CS1 protein (see above) were analyzed using the search software RANKPEP, BIMAS, and NetMHC, to predict peptides specific for HLA-A2. A total of four potential HLA-A2-binding native peptides were selected: CS1-P1: $CS1_{236\text{-}245}$ (LLLSLFVLGL (SEQ ID NO:15)); CS1-P2: $CS1_{239\text{-}247}$ (SLFVLGLFL (SEQ ID NO:16)); CS1-P3: $CS1_{232\text{-}240}$ (LLVPLLLSL (SEQ ID NO:17)); and CS1-P4: $CS1_{9\text{-}17}$ (TLIYILWQL (SEQ ID NO:18)). The HLA-A2 binding affinity of these native CS1 peptides and influenza virus protein matrix peptide$_{58\text{-}66}$ (GILGFVFTL (SEQ ID NO:24)) was assessed using the T2 peptide-binding assay. The affinity of the peptides was evaluated as HLA-A2-mean fluorescence intensity (MFI), HLA-A2 being up-regulated on T2 cells through the HLA-A2-specific binding. Peptides binding to HLA-A*0201 molecules were measured using the T2 cell line. T2 cells ($1\times10^6$ cells/mL) were incubated with 3 μg human $\beta_2$-microglobulin and/or 50 μg/mL of CS1 peptides. Influenza virus protein matrix peptide was used as positive control. Following overnight incubation, the cells were washed, stained with PE-labeled mouse anti-human HLA-A2 mAb and analyzed by flow cytometry. The Fluorescence Index (FI=mean channel fluorescence of T2 cells pulsed with the peptide plus $\beta_2$ microglobulin/mean channel fluorescence of T2 cells pulsed with $\beta_2$ microglobulin only) was calculated to determine the up-regulation of HLA-A2.1 molecules on T2 cells caused by HLA-A2.1-specific peptide binding.

Figure 20:
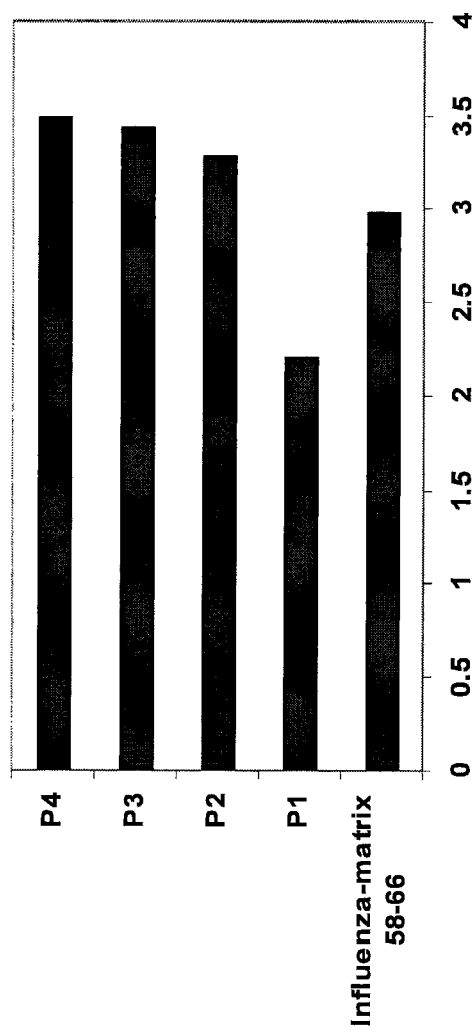
FIG. 20 is a bar graph depicting the affinity of fluorophore-labeled CS1 peptides for HLA-A2 molecules on the surface of human T2 cells. The X-axis represents the mean fluorescence intensity and the Y-axis indicates the various peptides screened in the assay: CS1-P1:CS1$_{236-245}$ (LLLSLFVLGL (SEQ ID NO:15)); CS1-P2: CS1$_{239-247}$ (SLFVLGLFL (SEQ ID NO:16)); CS1-P3: CS 1$_{232-240}$ (LLVPLLLSL (SEQ ID NO:17)); and CS1-P4: CS1$_{9-17}$ (TLIYILWQL (SEQ ID NO:18)). The influenza virus protein matrix peptide$_{58-66}$ (GILGFVFTL (SEQ ID NO:24); "Influenza matrix 58-66") was also evaluated as a control.

Among the tested peptides derived from CS1, three (P2, P3, and P4) had a higher affinity for HLA-A2 than the Influenza matrix peptide. The remaining peptide, P1 ($CS1_{236\text{-}245}$ (LLLSLFVLGL (SEQ ID NO:15))) exhibited only slightly lower HLA-A2 binding affinity than the Influenza matrix peptide (FIG. 20).

Example 17

Expansion of P2 Peptide-Specific CS1-CTL

CD8+ T cells were isolated from human peripheral blood mononuclear cells (PBMC) and cultured with P2 ($CS1_{239\text{-}247}$ (SLFVLGLFL (SEQ ID NO:16))) peptide-presenting autologous dendritic cells. The CD8+ cells were re-stimulated by the addition of peptide-presenting dendritic cells every 7 days. After the fourth re-stimulation, the percentage of CTL in the culture that were specific for $CS1_{239\text{-}247}$ were evaluated by flow analysis stained with PE-conjugated HLA-A*0201 P2-tetramer detection moiety and FITC-conjugated anti-CD8 monoclonal antibody. Approximately 4.1% of the cells in the population were bound by both the HLA-A*0201 P2-tetramer and the anti-CD8 antibody, indicating that approximately 4.1% of the cells were CS1-CTL.

Example 18

CS1 P2 peptide-specific cell activation of CS1-CTL

Figure 21:
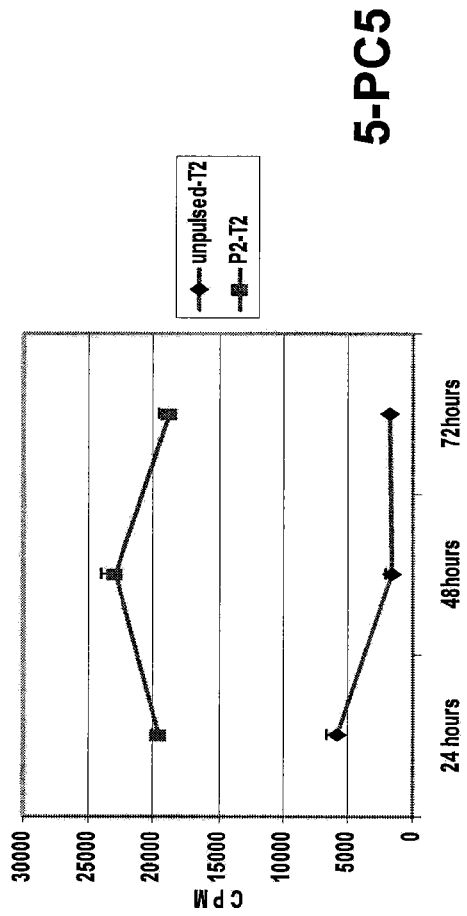
FIG. 21 is a line graph depicting the proliferation of CS1-P2-CTL contacted with human T2 cells presenting CS1-P2 peptide ("P2-T2") as determined by a thymidine incorporation assay. The Y-axis represents the counts per minute (CPM) of $^3$H-thymidine incorporated into the dividing cells and the X-axis represents the number of hours the CTL-containing cells were cultured with the T2 cells.

The proliferative activity of CS1-CTL was evaluated by tritiated thymidine ($^3$H-thymidine) incorporation assay. CS1-CTL ($5\times10^4$/well) were cultured with irradiated T2 cells ($5\times10^3$/well) presenting (or not presenting) CS1 P2 peptide at 24, 48, and 72 hours, respectively. $^3$H-thymidine (0.5 μCi) was added to the wells 12 hours before harvesting the cells. CS1-CTL cultured with CS1 P2-presenting T2 cells exhibited a marked increase in proliferation as compared to CS1-CTLs that were contacted with T2 cells not presenting CS1 P2 peptide (FIG. 21). The activation of CS1-CTLs was determined at 48 hours of incubation by measuring the upregulation of surface PC5 expression by flow cytometry using a monoclonal anti-CD25-PC5 antibody. The finding that the proliferating CS1-CTL exhibited an increase in PC5 expression upon culture with CS1 P2-presenting T2 cells suggested that the CS1-CTL were also activated.

Example 19

Antigen-Specific and HLA-A2-Restricted IFN-γ Secretion by the CS1-CTL

Figure 22:
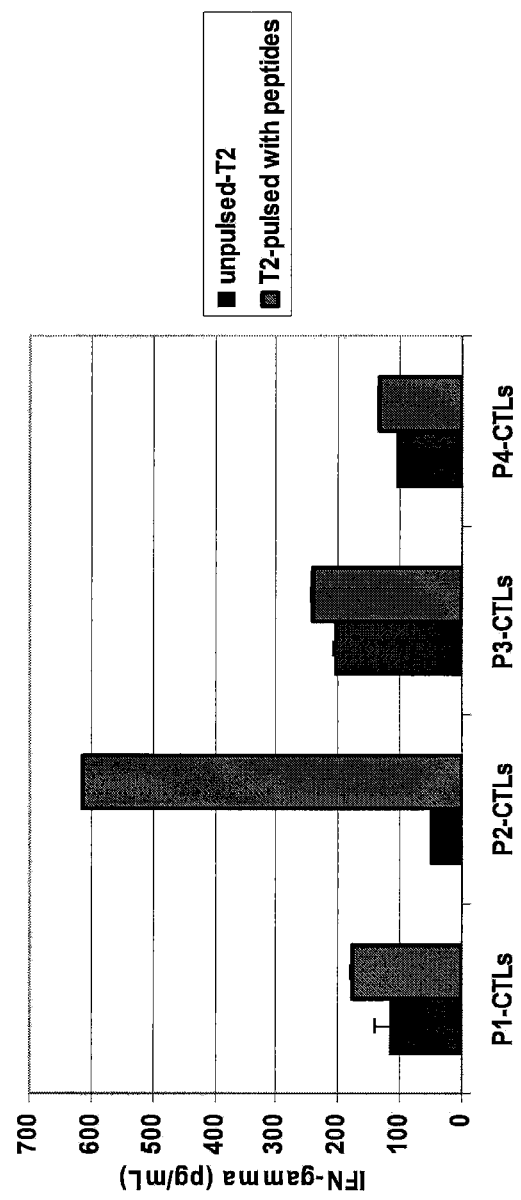
FIG. 22 is a bar graph depicting the release of IFN-γ from CS1-CTL (P1-, P2-, P3-, and P4-CTLs) co-cultured with T2 cells presenting CS1-P1, CS1-P2, CS1-P3, or CS1-P4 peptides, respectively. The Y-axis represents the amount of IFN-γ released from the CTL in units of pg/mL.

Further confirmation of the antigen-specificity and HLA-A2-restriction of the CS1-CTL was provided by the induction of IFN-γ secretion following overnight stimulation of each of the four different CS1-CTL populations (CS1-P1-CTL, CS1-P2-CTL, CS1-P3-CTL, and CS1-P4-CTL) with T2 cells presenting the respective CS1 peptides in the context of surface HLA-A2. While each of the CS1-CTL populations exhibited some increase in IFN-γ secretion, the CS1-P2-CTL exhibited the largest degree of IFN-γ secretion following contact with P2-peptide presenting T2 cells (FIG. 22). These results provide further evidence of an antigen-specific and HLA-A2-restricted response by the CS1-CTL populations.

Example 20

CS1-CTL in a Calcien-Cytotoxicity Assay

Figure 23:
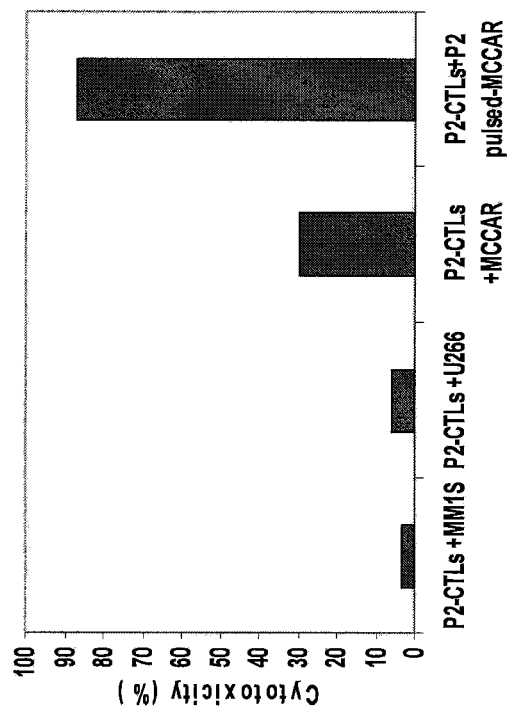
FIG. 23 is a bar graph depicting the CS1-CTL-dependent lysis of cancer cells as determined by calcein-release assay. P2-CTL were co-cultured with each of cancer cells U266, McCAR, ML-2, or MM1S cells and the amount of cancer cell lysis induced by the CS1-CTL was calculated as a function amount of calcein released from the cancer cells. The Y-axis represents the percent cytotoxicity.

The ability of the CS1-CTL to specifically target and lyse multiple myeloma cells was determined. The CS1-CTL were activated twice with CS1-P2 peptide (on day 1 and day 7) and were examined for their ability to lyse multiple myeloma cells as determined by calcein release cytotoxicity assays. MM cell lines (MM.1S, U266 and MCCAR) were labeled by calcein-AM (5 µg/ml) and used as target cells at 5,000 cells/well. The ratio of effector cells to target cells was 20:1. As shown in FIG. 23, CS1-P2-CTLs were effective at killing (30% cytotoxicity) of the target MM cell line MCCAR (HLA-A2$^+$/CS1$^+$), whereas no significant cytotoxicity was observed with MM.1S (HLA-A2$^-$/CS1$^+$) and U266 (HLA-A2$^+$/CS1$^-$) target cells. Moreover, CS1-CTLs displayed high cytotoxicity to MCCAR cells that had been contacted with P2 peptide, thereby confirming the peptide-specific and HLA-A2-restricted cytotoxic effect.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inducing an immune response in a subject having multiple myeloma, the method comprising administering to the subject a composition comprising:
   (a) a CS-1 peptide consisting of the amino acid sequence of SEQ ID NO:16,
   (b) an XBP-1 peptide consisting of the amino acid sequence of SEQ ID NO:6,
   (c) an XBP-1 peptide consisting of the amino acid sequence of SEQ ID NO:10, and
   (d) a CD138 peptide consisting of the amino acid sequence of SEQ ID NO:12.

2. The method of claim 1, wherein the composition further comprises a pharmaceutically acceptable carrier.

3. The method of claim 2, wherein the pharmaceutically acceptable carrier is one or more of a sterile diluent, an antibacterial agent, an antioxidant, a chelating agent, a buffer and an agent for the adjustment of tonicity.

4. The method of claim 3, wherein the sterile diluent comprises one or more of water for injection, saline solution, fixed oils, polyethylene glycol, glycerine, propylene glycol and other synthetic solvents.

5. The method of claim 1, wherein the composition further comprises one or more agents selected from therapeutic agents, diagnostic agents, prophylactic agents and immunostimulatory agents.

6. The method of claim 5, wherein the composition comprises one or more immunostimulatory agents.

7. The method of claim 6, wherein the one or more immunostimulatory agents comprises an adjuvant.

8. The method of claim 7, wherein the adjuvant is one or more of Freund's incomplete adjuvant, alum, a ligand for a Toll receptor, QS21, RIBI, mutant cholera toxin (MCT), and mutant *E. coli* heat labile toxin (MLT).

9. The method of claim 8, wherein the adjuvant comprises Freund's incomplete adjuvant.

10. The method of claim 8, wherein the adjuvant comprises a ligand for a Toll receptor.

11. The method of claim 1, wherein the subject is a human.

* * * * *